(12) United States Patent
Fang

(10) Patent No.: US 8,304,758 B2
(45) Date of Patent: Nov. 6, 2012

(54) PROCESS OF CONSTRUCTING OXIDATION-REDUCTION NANOMEDICINE QUANTUM DOTS ROOM TEMPERATURE QUANTUM BIT NETWORKS

(75) Inventor: Yan Fang, Shanghai (CN)

(73) Assignee: Zhongshan Hospital, Fudan University, Shanghai (CN)

( * ) Notice: Subject to any disclaimer, the term of this patent is extended or adjusted under 35 U.S.C. 154(b) by 1295 days.

(21) Appl. No.: 12/002,888

(22) Filed: Dec. 19, 2007

(65) Prior Publication Data

US 2012/0149581 A1 Jun. 14, 2012

(30) Foreign Application Priority Data

Dec. 20, 2006 (CN) .......................... 2006 1 0147584

(51) Int. Cl.
 *H01L 31/00* (2006.01)
(52) U.S. Cl. .... 257/14; 977/906; 505/150; 257/E29.072
(58) Field of Classification Search .................. None
 See application file for complete search history.

(56) References Cited

U.S. PATENT DOCUMENTS

| | | | |
|---|---|---|---|
| 5,589,692 | A | 12/1996 | Reed |
| 6,060,327 | A | 5/2000 | Keen |
| 2006/0292081 | A1 | 12/2006 | Morton et al. |

FOREIGN PATENT DOCUMENTS

| | | |
|---|---|---|
| CN | 1049115 C | 2/2000 |
| CN | 2004/00099386.2 | 12/2004 |

(Continued)

OTHER PUBLICATIONS

Gao et al. Superconductivity up to 164 K in HgBa2Cam-1CumO2m+2+δ (m=1, 2, and 3) under quasihydrostatic pressures, Phys. Rev. B 50, 4260-4263 (1994).* http://en.wikipedia.org/wiki/High-temperature_superconductor.*
Merriam-Webster Dictionary.*

(Continued)

*Primary Examiner* — Benjamin Sandvik
*Assistant Examiner* — Scott R Wilson
(74) *Attorney, Agent, or Firm* — Hamre, Schumann, Mueller & Larson, P.C.

(57) ABSTRACT

Preparation of oxidation-reduction (redox) nano-medicine quantum dot room temperature superconductor quantum bit (qubit) networks includes processes of making unitary, binary, ternary, an d/or quaternary liquid pharmaceutical ingredients of an antioxidase antioxidant, a β-adrenergic receptor agonist, a $P_2$-purinergic receptor agonist, and/or a phenylalkylamine calcium channel blocker in combination with either 1:20 xanthine oxidase (XO):xanthine (X) or X alone in a liquid phase by using the $L_{16}(2)^{15}$ and $L_9(3)^4$ orthogonal optimization design protocols and modulating spatial distance constraint from about 0.1 Å to about 200 Å as well as a 10 class clean bottom-up self-assembly approach. Redox nano-drug quantum dot superconductor qubit network can be identified at room temperature by Planck constant ($\hbar$)-related qubit metrology of electron spins and polaritons (the quantum state of photon-exciton hybrid or photoelectron coupling/co-tunneling) through conducting atomic force microscopy (C-AFM) and/or laser micro-photoluminescence (PL) spectrum standard measurement method, wherein $\hbar$-related quantum continuous variables (QCVs) are derived from faster Fourier transformation (FFT) of average current-voltage (I-V) curves and PL spectra, their first derivatives of relative phases in frequency and time domains ($dr/df=\Delta E/\hbar$ and $dr/dt=\Delta E/\hbar$) and their FFTs to acquire $\Sigma(2'')$, $\Sigma(2''\cdot 2'')$, $\Sigma(2^{n+1})$, $\Sigma(2^{n}\cdot 2^{n})$, $\Sigma(2^{2n+1}\cdot 2^{2n+1})$ and/or $\Sigma(2^{2n+1})$ binary superconductor qubit matrix networks. Uses of this invention cover room temperature superconductor (resistance loss, insulator with conductor or ∞ conductance) quantum devices and quantum biology metrology, implanted nano-drug quantum dot diagnostic and therapeutic nanodevices and/or nano-bio-electrochemistry sensors with target-recognized functions.

6 Claims, 30 Drawing Sheets
(28 of 30 Drawing Sheet(s) Filed in Color)

FOREIGN PATENT DOCUMENTS

DE 198 52 543 A1 5/2000
JP 2003-76036 A 3/2003

OTHER PUBLICATIONS

Marouchkine, Room-Temperature Superconductivity, 2004, Cambridge International Science Publishing, Introduction.*

Fang et al. Mode-actions of the Na(+)-Ca2+ exchanger: from genes to mechanisms to a new strategy in brain disorders. Biomed Pharmacother 52(4), 1998, p. 145-156.

Substitute Specification and Preliminary Amendment filed with Co-Pending U.S. Appl. No. 11/813,265 on Jul. 2, 2007.

Substitute Specification filed with Co-Pending U.S. Appl. No. 11/886,490 on Sep. 17, 2007.

Co-Pending U.S. Appl. No. 12/008,904, filed Jan. 15, 2008.

Fang et al. "The mechanisms of synergy of four drugs in protecting cortico-cerebral function from anoxic damage." Zhongguo Yingyong ShenglixueZazhi, 12(3), 1996, p. 223-226. (Abstract provided).

Yu et al. "Self-Assembly Techniques for Fabrications of Nanocomposite Thin Films." Wuhan Ligong Daxue Xuebao • Xinxi Yu Guangligongcheng Ban, 24(4), 2002, p. 137-141. (Abstract provided).

* cited by examiner

Figure 4a-d
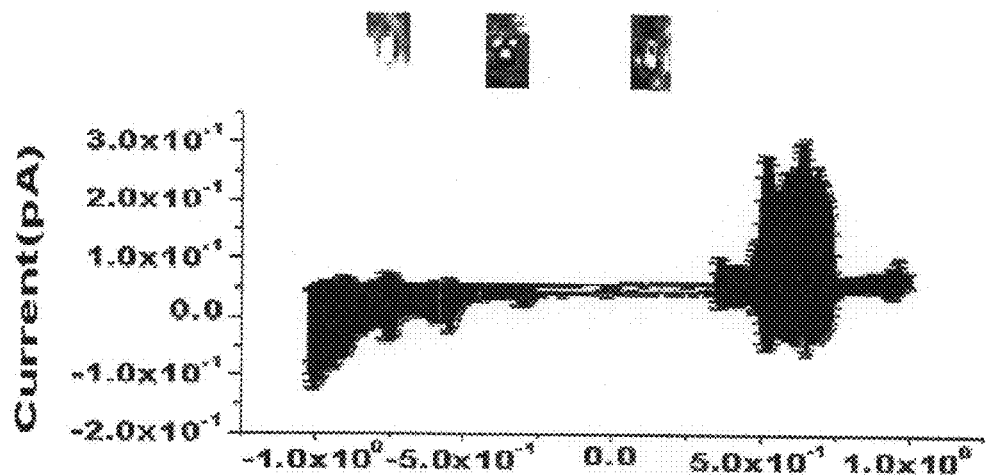
Figure 4e-f
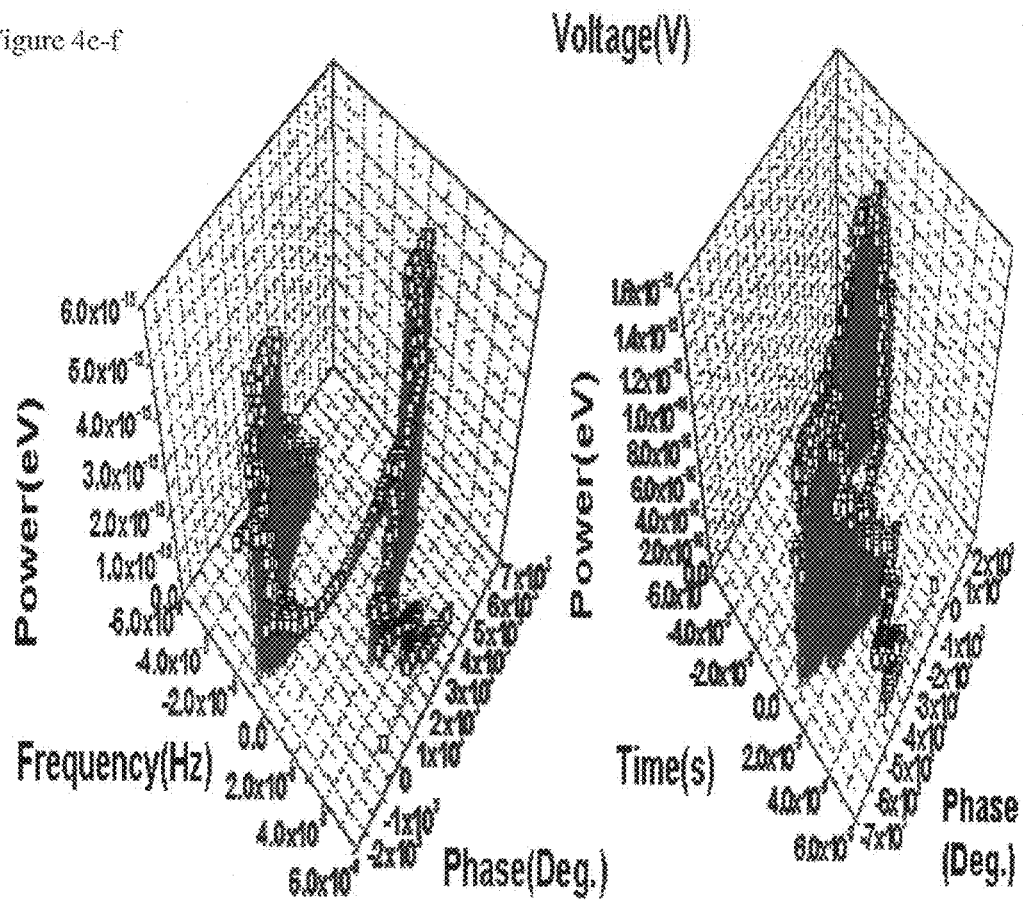

Figure 6III
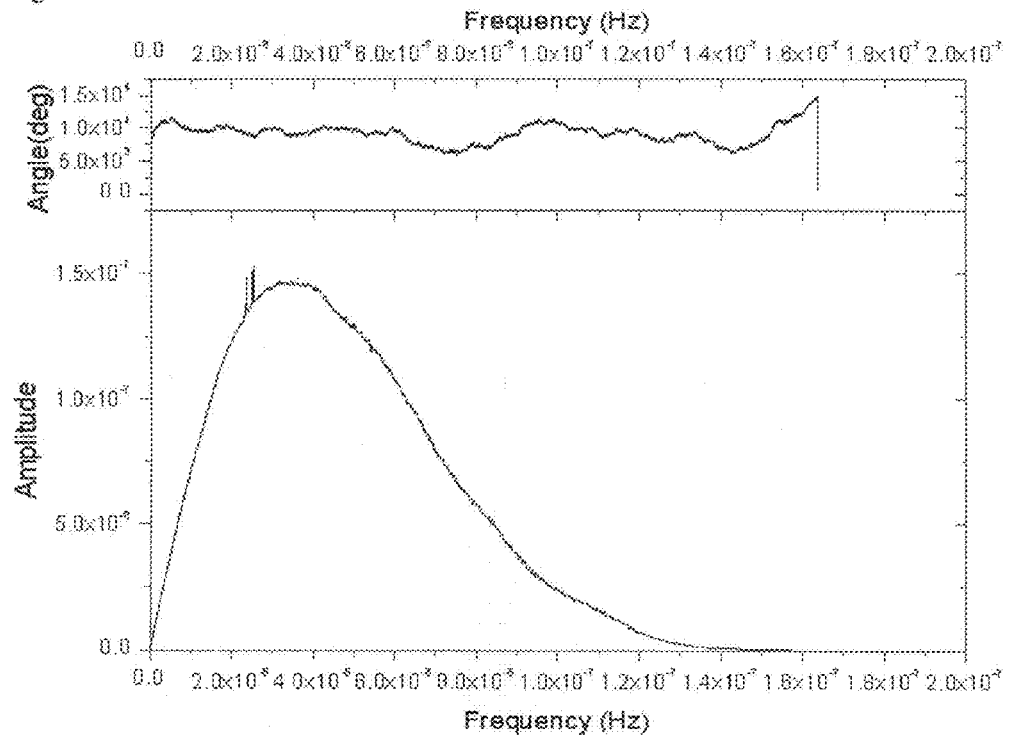
Figure 6IV
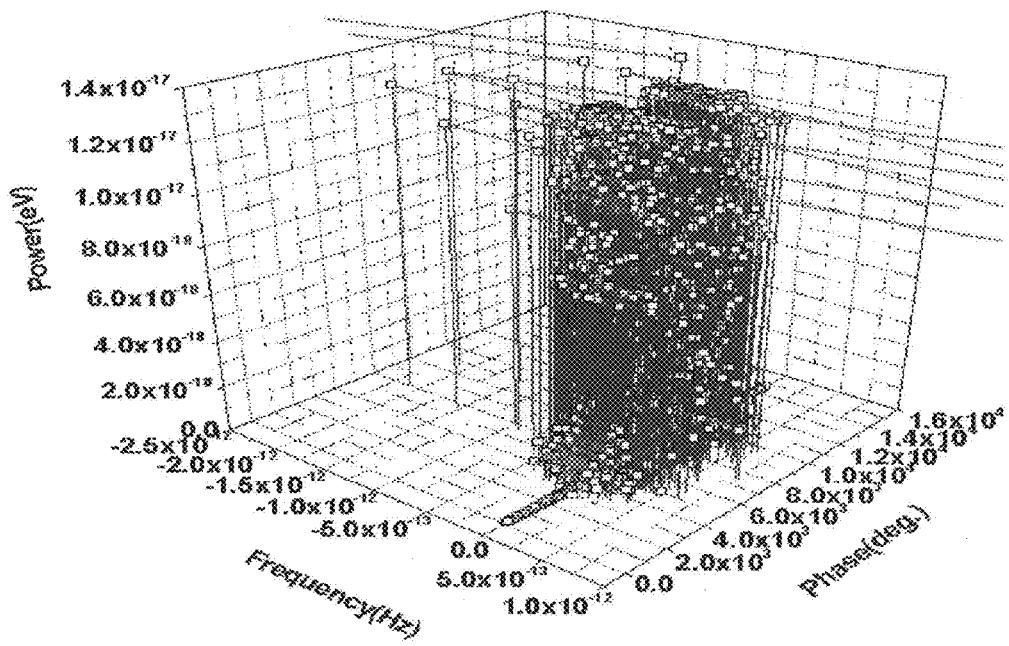

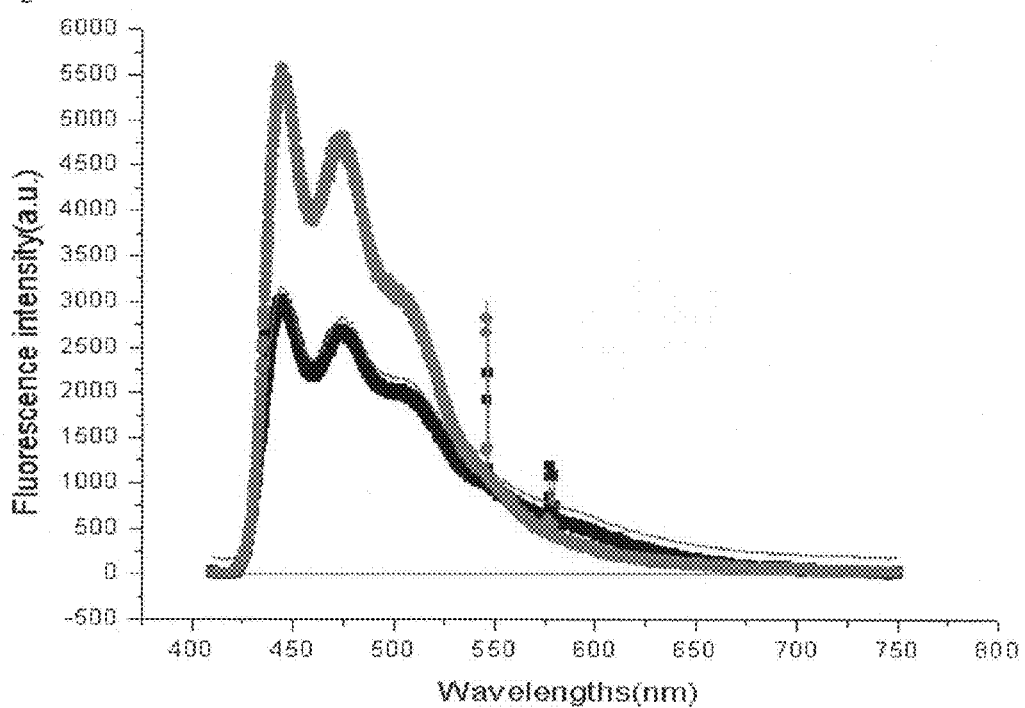
Figure 6VII
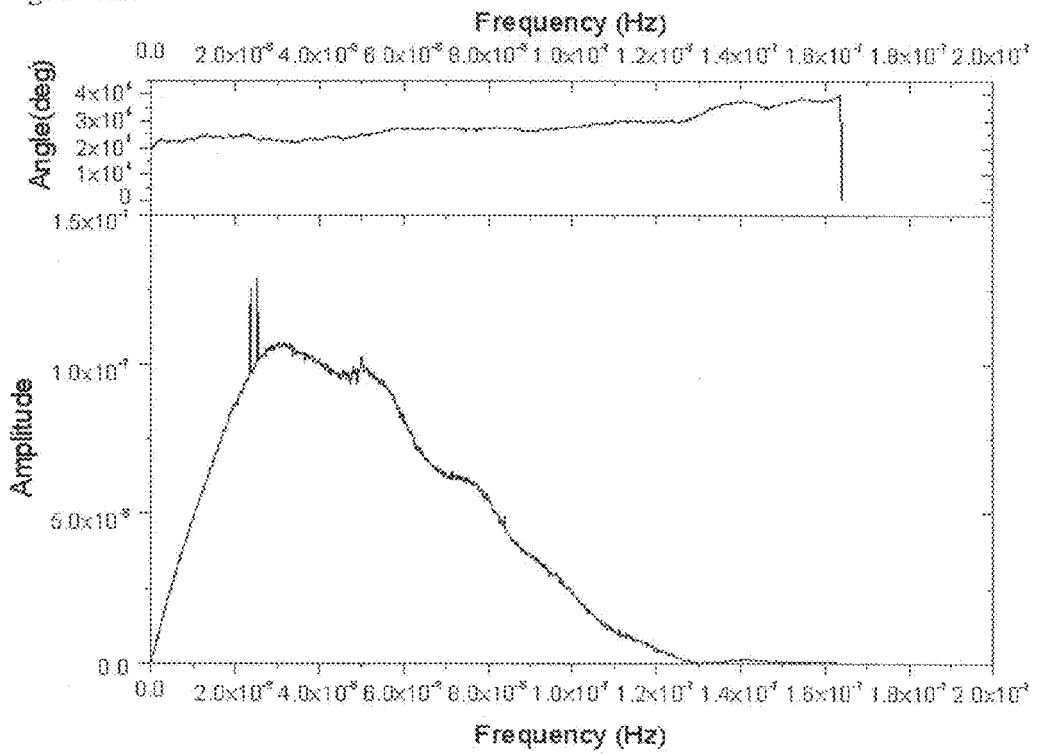
Figure 6VIII

US 8,304,758 B2

PROCESS OF CONSTRUCTING OXIDATION-REDUCTION NANOMEDICINE QUANTUM DOTS ROOM TEMPERATURE QUANTUM BIT NETWORKS

RELATED APPLICATIONS

This application is the non-provisional patent application and claims the benefit of foreign priority of Chinese Patent Application No. 200610147584, filed Dec. 20, 2006, and supported by governmental grants of the National Science Foundation of China (NSFC30470409) & Shanghai Science and Technology Committee (STC03JC14020 & 0452 nm085) that should be acknowledged.

TECHNICAL FIELD

This invention relates to preparation processes of turning a hybrid system of liquid pharmaceutical ingredients and a bio-redox single electron tunneling into a redox nano-medicine quantum dot room temperature superconductor qubit network and promising broad uses in high density and high performance qubit memory devices, nano-drug quantum dot diagnostic and therapeutic new tools and qubit metrology as well as advanced nano-fabrication.

BACKGROUND

Redox nano-drug quantum dot room temperature superconductor qubit networks are the key component for developing high performance quantum calculation and implanted ultra-fast or ultra-sensitive diagnostic nano-devices and nano-biosensors. It becomes the hot point of biochemistry, informatics, nano-technology and advanced functional semiconductor nano-particle materials as well as extreme fabrication fields. Single bio-electron tunneling at room temperature is a peculiar property of redox nanomedicine quantum dots under the external field effects, for example, employing a serial of electrical pluses, laser and/or photo-electro-magnetic fields. External fields-induced $\pm \frac{1}{2}\pi N$ single electron spin-up and spin-down states at the surface of redox nanomedicine quantum dots generates one-level and two-level qubit operators either $|0>$ and $|1>$ or $|00>$ and $|11>$, which are fundamental factors to perform qubit memory, ultra-fast and ultra-sensitive diagnostic techniques and nano-bio-photo-electron sensors. Verapamil, isoproterenal, superoxide dismutase and adenosine triphosphate are promising to act as building blocks with peculiar bio-photoelectron spins for qubit operators under external fields providing that room temperature single electron and single photon co-tunneling interactions and single electron spins occur in the nanometer spatial structures. Owning to the merit of room temperature single bio-electron and single photon co-tunneling interactions and spins is unique, the room temperature superconductor qubit network of redox nano-drug quantum dots may be achieved by a bottom-up self-assembly approach and superconductor qubit networks may be identified by $\hbar$-related qubit metrology for electron spins through C-AFM I-V and/or laser micro-PL spectrum measurement method standard, wherein $\hbar$-related quantum continuous variables (QCVs) can be acquired from faster Fourier transformation (FFT) of average I-V curves and PL spectra, their first derivatives of relative phases in frequency and time domains ($dr/df=\Delta E/\hbar$ and $dr/dt=\Delta E/\hbar$) and their FFTs providing that qubit operators satisfy the superconductor binary code matrix of either $\Sigma(2^n)n$, $\Sigma(2^n \cdot 2^n)n$, $\Sigma(2^{n+1})n$, $\Sigma(2^{2n} \cdot 2^{2n})n$, $\Sigma(2^{2n+1} \cdot 2^{2n+1})n$ or $\Sigma(2^{2n+1})n$.

SUMMARY

In one aspect of the invention, a feature of constructing redox nanomedicine quantum dot room temperature qubit networks contains a process of a droplet-quantum crystal lattice epitaxy bottom-up self-assembly approach to prepare basic building blocks of redox nanomedicine quantum dot room temperature superconductor qubit networks by turning aromatic structures-, single electrons-, single photons-based redox pharmaceuticals into molecular mono-layered room temperature superconductor qubit network structures in a liquid phase, including co-crystallized semiconductor nano-particles (quantum dots), controlled NOT (CNOT) and Majority quantum cellular automates (QCAs), three-particle single electron transistors and qubit central processor units (QCPU).

The preparation process of the invention may include the following features.

i) In a 10 class clean environment, a liquid required for a redox nanomedicine quantum dot room temperature superconductor qubit network may be respectively prepared according to the $L_{16}(2)^{15}$ and $L_9(3)^4$ orthogonal optimum protocols and pharmaceutical standards, which may refer to the safe food drug agency (SFDA) issued by the Ministry of Health in China.

ii) A 3-dimensional (3D) size-controlled redox nano-medicine quantum dot room temperature superconductor qubit network may be respectively prepared according to the $L_{16}(2)^{15}$ and $L_9(3)^4$ orthogonal optimum protocols in a liquid phase by a bottom-up self-assembly approach of controlling the intermolecular spatial distance from about 0.1 Å to about 200 Å.

iii) Droplets for a required redox nanodrug quantum dot room temperature superconductor qubit network may be respectively put onto substrate surfaces, for example, either a freshly separated clean highly ordered graphite surface, a 0.01-0.05 Ω·cm n-doped silicon surface with hydrogen bonding or a 8-12 Ω·cm p-doped silicon surface with hydrogen bonding, according to the $L_{16}(2)^{15}$ and the $L_9(3)^4$ orthogonal optimum protocols and national pharmaceutical manufacture standards. Alternatively, a 0.01-0.05 Ω·cm n-doped silicon surface with hydrogen bonding or a 8-12 Ω·cm p-doped silicon surface with hydrogen bonding may be respectively immersed in the desired redox pharmaceutical hydrochloride and physiological buffer solutions according to the $L_{16}(2)^{15}$ and the $L_9(3)^4$ orthogonal optimum protocols. Liquid redox pharmaceutical samples may be kept at room temperature (4-18° C.) onto the graphite substrate for 30-60 minutes, liquid redox pharmaceutical samples may be coated onto the silicon substrates at either ~4-20° C. critical self-assembly temperature for a period of either 8-12 or 96 hours, up to forming either redox nanomedicine quantum dot networks with electron spins (qubits) in a $\Sigma(2^n)$ and/or a $\Sigma(2^{n+1})$ binary code matrix (superconductor) manner iv) A droplet of hetero-molecular core-shell quantum dot lattice epitaxy may be respectively made onto the substrate in the $L_{16}(2)^{15}$ and the $L_9(3)^4$ orthogonal optimum protocols by a hybrid redox nanomedicine droplet to form a hetero-molecular core-shell quantum dot lattice, a three-quantum dot transistor, and a qubit central processor unit.

v) A hybrid redox nanomedicine droplet to form the redox nanomedicine quantum dot room temperature qubit network embodiment of a hetero-molecular core-shell quantum dot lattice, a three-quantum dot transistor, and a qubit central processor unit as well as a quantum cellular automate (QCA) may be a uni-, bi-, tri-, tetra-, quin- and/or hexa-hybrid droplet of agonists of the β-adrenergic receptor and the $P_2$-purinergic receptor (isoproterenol hydrochloride and adenosine triphosphate buffer solutions), antagonists of the $Ca^{2+}$ channel and the super-oxide anion (verapamil hydrochloride and superoxide dismutase buffer solutions), and XO:X or X buffer solutions.

vi) A redox nanomedicine quantum dot room temperature qubit network, including a hetero-molecular core-shell quantum dot lattice, a three-quantum dot transistor, a qubit central processor unit and/or a QCA, may be made by about single molecules to about trillion billions of uni-, bi-, tri-, tetra-, quin- and/or hexa-hybrid molecules selected from 24 groups of molecular mixture ratios of verapamil hydrochloride:isoproterenol hydrochloride:superoxide dismutase buffer:adenosine triphosphate buffer with either 1:20 XO:X or X as follows: (i) 1:0:0:0; (ii) 0:1:0:0; (iii) 0:0:1:0; (iv) 0:0:0:1; (v) 1:1:0:0; (vi) 1:0:1:0; (vii) 1:0:0:1; (viii) 0:1:1:0; (ix) 0:1:0:1; (x) 0:0:1:1; (xi) 1:1:1:0; (xii) 1:0:1:1; (xiii) 1:1:0:1; (xiv) 0:1:1:1; (xv) 1:1:1:1; (xvi) 1:2:2:2; (xvii) 1:3:3:3; (xviii) 2:1:2:3; (xix) 2:2:3:1; (xx) 2:3:1:2; (xxi) 3:1:3:2; (xxii) 3:2:1:3; (xxiii) 3:3:2:1, and combinations thereof, in an $L_{16}(2)^{15}$ and an $L_9(3)^4$ orthogonal design protocols, wherein (xv) may be same a tetra-hybrid droplet in an $L_{16}(2)^{15}$ and an $L_9(3)^4$ orthogonal design protocols.

vii) Washing substrate surfaces three times with clean deionized water after 96 hours must be done to secure a self-assembled monolayer of redox nanomedicine quantum dot network lattice onto the substrates for some embodiments of single molecular scale redox nanomedicine room temperature superconductor qubit networks.

The invention of redox nano-drug quantum dot room temperature superconductor qubit networks may include the following features. A single bioelectronics system is coupled with pharmaceutical ingredients of an agonist of the β-adrenergic receptor, an agonist of the $P_2$-purinergic receptor, an antioxidase antioxidant, and an antagonist of the $Ca^{2+}$ channel in a uni-, a bi-, a tri-, a tetra-, a quinque- or a hexa-complex manner. The β-adrenergic agonist may include isoprenaline. The molecular number of a desired isoprenaline hydrochloride solution may be in a range of about single molecule to about $10^{15}$-$10^{14}$. The $P_2$-purinergic agonist may include adenosine triphosphate. The molecular number of a desired adenosine triphosphate physiological buffer solution may be in a range of about single molecule to about $10^{11}$-$10^{19}$. The phenylalkyl-amine calcium channel blocker may include verapamil. The molecular number of a desired verapamil hydrochloride solution may be in a range of about single molecule to about $10^{12}$-$10^{14}$. The antioxidase antioxidant may include superoxide dismutase. The molecular number of superoxide dismutase may be in a range of about single molecule to about $10^{11}$-$10^{13}$. The single bioelectronics system may be either xanthine oxidase (XO) and xanthine (X) or X. The molecular mixture ratio of XO:X may be 1:20. The molecular number of XO may be in a range about single molecule to about much more molecules. The molecular number of X may be in a range of about 1-20 single molecules to about $3\times10^{16}$-$3\times10^{19}$.

For the coupled embodiments of single molecular level pharmaceutical-xanthine droplet hybrids, unitary complexes of a redox nano-medicine quantum dot room temperature superconductor qubit network composition may comprise a single molecular mixture ratio of (verapamil:isoprenaline:superoxide dismutase:adenosine triphosphate) selected from the group consisting (i) 1:0:0:0; (ii) 0:1:0:0; (iii) 0:0:1:0; (iv) 0:0:0:1, and combinations thereof, in an $L_{16}(2)^{15}$ orthogonal design protocol. Binary complexes of a redox nano-medicine quantum dot room temperature superconductor qubit network composition may comprise a single molecular mixture ratio of (verapamil:isoprenaline:superoxide dismutase:adenosine triphosphate) selected from the group consisting of (i) 1:1:0:0; (ii) 1:0:1:0; (iii) 1:0:0:1; (iv) 0:1:1:0; (v) 0:1:0:1; (vi) 0:0:1:1, and combinations thereof, in an $L_{16}(2)^{15}$ orthogonal design protocol. Ternary complexes of a redox nano-medicine quantum dot room temperature superconductor qubit network composition may comprise a single molecular mixture ratio of (verapamil:isoprenaline:superoxide dismutase:adenosine triphosphate) selected from the group consisting of (i) 1:1:1:0; (ii) 1:0:1:1; (iii) 1:1:0:1; (iv) 0:1:1:1, and combinations thereof in an $L_{16}(2)^{15}$ orthogonal design protocol. Quaternary complexes of a redox nano-medicine quantum dot room temperature superconductor qubit network composition may comprise a single molecular mixture ratio of (verapamil:isoprenaline:superoxide dismutase:adenosine triphosphate) selected from the group consisting of (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; (ix) 3:3:2:1, and combinations thereof, in an $L_9(3)^4$ orthogonal design protocol, wherein (i) may be overlapped in an $L_{16}(2)^{15}$ orthogonal design protocol. All of them are mixed with xanthine at the single molecular level.

The feature of a redox nano-medicine quantum dot room temperature superconductor qubit network composition may be identified by either C-AFM topographic structure images and I-V curve measurements, laser micro-PL spectra or both at room temperature and in air, wherein $\hbar$-related QCVs may be acquired from faster Fourier transformation (FFT) of average I-V curves and/or PL spectra, their first derivatives of relative phases in frequency and time domains ($dr/df=\Delta E/\hbar$ and $dr/dt=\Delta E/\hbar$) and their FFTs for characterizing qubit operator permutations, angular frequency of electron spins, phase transitions for qubits, velocities and amplitudes of quantum waves and electron-photon coupling effects in frequency and time domains.

The feature of a redox nano-medicine quantum dot room temperature superconductor qubit network composition may be modulated under different external fields, for example, altering laser sources, photon energy levels, electron or photon pulses and/or employing spinning magnetic fields, for instance, toned tuned spinning magnetic fields of 70D, 70D150t, 98D, 101D, 104D, 109D, 113D, 117D, RTD10, RTD50t, RTD110t, according to the $L_{16}(2)^{15}$ and $L_9(3)^4$ orthogonal optimum protocols, thereby, symmetry spin-up and spin-down qubits and non-symmetry spin-up and spin-down qubits may be converted either at about $\pm 10^{-19}$ Hz/s to about $\pm 10^{-7}$ Hz/s in frequency and time domains or at about $\pm 10$V bias potentials. The electron-photon coupling-driven single-level and two-level Hadamard and XOR quantum gated room temperature superconductor qubit networks may be acquired within $\pm 5000$ nm wavelengths, wherein qubit networks may include qubit operators in a range of about unitary qubit operators (|10> and |1>) to about several millions of single-level and two-level qubit operator networks and qubit operator permutations. Energy flips of qubit networks in frequency and time domains may be in a range of about 5.441E-36 eV to about 109339.95665 eV. Angular momentum of phase transitions in frequency and time domains may be in a range of about $10^{-19}$ Hz to about $10^5$ Hz. Phase transitions may undergo $\pm\frac{1}{2}\pi N$ Pauli Z magnetic momentum.

The feature of redox nano-drug quantum dot room temperature superconductor qubit networks may satisfy the trillion level binary code matrix Hamiltonians of superconductor qubit networks as follows. $\Sigma\{(2^n), n=1, 2, 3, 4, 5, 6, 7, 8, 9, 10, 11, 12 \ldots\}; \Sigma\{(2^n \cdot 2^n), n=1, 2, 3, 4, 5, 6 \ldots\}; \Sigma\{(2^{n+1}), n=1,$ 2, 3, 4, 5, 6, 7, 8, 9, 10, 11 ... }; $\Sigma\{(2^{2n} \cdot 2^{2n}), n=1, 2, 3 ... \}$; $\Sigma\{(2^{2n+1} \cdot 2^{2n+1}), n=1, 2, ...\}$; $\Sigma(2^{2n+1}), n=1, 2, 3, 4, 5, ...\}$.

The feature of redox nano-drug quantum dot room temperature superconductor qubit networks may be single electron spins- and/or single photoelectron co-tunneling-driven quantum circuit-gated room temperature superconductor qubit networks, wherein single bio-electron spins may confer a feature of $\pm\frac{1}{2}\pi N$ phase transitions for one-level and two-level qubit operator networks and their permutations at room temperature.

The bi-stable spin-down and spin-up quantum resonance transport feature of redox nano-drug quantum dot room temperature superconductor qubit networks may conclude the weak spin-orbital and hyperfine hybrid of molecular scale quantum and/or magnetic tunnel junctions (QTJs and/or MTJs) to be acted as promising ultra-thin and/or ultra-small spintronic devices.

The embodiment feature of redox nano-drug quantum dot room temperature superconductor qubit networks may be atomic scale CNOT- and Majority-gated QCA architectures that may be identified by C-AFM images and laser-micro-PL spectra as well as $\hbar$-related QCVs, especially the forward and backward FFTs of $dr/df=\Delta E/\hbar$ and $dr/dt=\Delta E/\hbar$.

The double-peaked PL spectra of redox nano-drug quantum dot room temperature superconductor qubit networks may directly confer the band-gap structure feature of bonding and anti-bonding energy states between two coupled redox nano-drug quantum dots and/or electrostatic quantum dot networks.

The double-oriented electron-hysteresis-like peaks within an average difference conductance spectrum may confer the superconductor band-gap structure feature of bonding and anti-bonding energy states between two coupled redox nano-drug quantum dots and/or electrostatic quantum dot networks The band-gap structure dynamic feature of redox nano-drug quantum dot room temperature superconductor qubit networks may be identified by qubit metrology ($\hbar$-related measurement method standard of qubits), which may comprise QCVs, namely, double-peaked average I-V curves, double-peaked average differential conductance spectra and double-peaked average laser micro-PL spectra, their FFTs, the 1st derivative of relative phases in frequency and time domains (dr/df & dr/dt), and dr/df & dr/dt FFTs, wherein either dr/df or dr/dt equal to $\Delta E/\hbar$.

The $\hbar$-related measurement method standard of qubits may comprise the prior calibration of C-AFM tip and/or laser-micro-PL spectrum system tool, as well as standard samples as the background signal to acquire QCVs of redox nano-drug quantum dot room temperature superconductor qubit networks in comparison with the background signal for final statistical significance (P value) tests.

Strategic utility of embodiments in the invention covers national defense, and international information security, as well as nanotechnology and nanoscience.

Industry utility of embodiments in the invention covers bio-photoelectron sensors, advanced information materials, single bioelectronics transistors, implanting nano-bio-photoelectron sensors, newly medical diagnostic tools like room temperature superconductivity nuclear magnetic imaging, cardio-cerebral magnetic probing, high performance single bioelectronics and single bio-photon co-tunneling-driven room temperature superconductivity qubit informatics and nanometer photoelectron biosensors, and key technology employed in communication, traffic and national defense advanced tools like quantum computers, superconductivity magnetic body and energy storage systems.

Standard utility of embodiments in the invention covers standard reference samples and nano-metrology of qubits and QCAs as well as qubit circuits.

The details of one or more embodiments of the invention are set forth in the accompanying drawings and the description below. Other features, objects, and advantages of the invention will be apparent from the description and drawings, and from the claims.

DESCRIPTION OF DRAWINGS

The patent or application file contains at least one drawing executed in color. Copies of this patent or patent application publication with color drawings will be provided by the Office upon request and payment of the necessary fee.

FIG. 1$a$-$d$ extended FIG. 2 in the PCT/CN/2005/002368 application. The preparation process of a sample in FIG. 1$a$-$d$ follows up the desired 0:1:0:0 molar ratio in the $L_{16}(2)^{15}$ orthogonal design protocol.

FIG. 4. A, B and C, Single molecular level Redox nano-medicine core-shell quantum dots are respectively C-AFM images for topographic structures of size-controllable core-shell quantum dot structure at a diameter of 2.6 nm, the 2.6 nm three quantum dot particle transistor, and the 2.6 nm room temperature superconductivity qubit central processor unit (CPU) architecture onto the 0.01-0.05 Ω·cm n-doped silicon chip, according to the molecular mixture ratio of 1:3:3:3 in the $L_9(3)^4$ orthogonal design model. D, The C-AFM probes an average I-V curve of 6 measurements with s.d. of FIG. 4a, wherein around 0.05 pA single electron spin-up and spin-down current transports in an electron spin-up and spin-down tunneling transport hysteresis loop are clearly visible within ±0.25V bias potentials for memory of qubits. E and F, The $\hbar$-related symmetry spin-up and spin-down QCVs associate with dynamics of power, frequency, time and phase in one- and two-level qubit couplings, wherein the qubit operator networks of ±34200 phase transition degrees satisfy the room temperature superconductor qubit operator network Hamiltonian as follows. $\{H=\Sigma\{(2^n), n=1, \ldots 4, 5, 6, \ldots 8\}$ for 23 two-level symmetry spin-down and spin-up XOR-gated qubit operator networks with a unitary qubit operator $|1\rangle$ in a sum of ±34200 phase transition degrees with $\pm\frac{1}{2}\pi N$ symmetry spin-down and spin-up qubit operator networks.

DETAILED DESCRIPTION

Figure 1A:
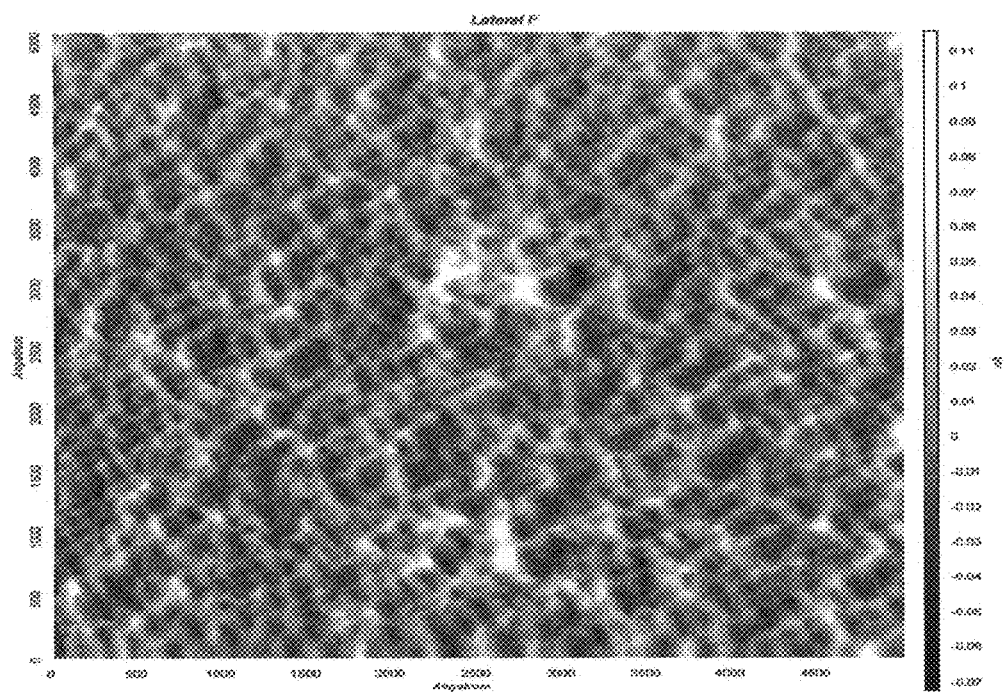
FIG. 1. A, C-AFM characterizes quantum tunneling current spectrum of redox nanomedicine quantum dot room temperature qubit networks onto the 0.01-0.05 $\Omega\cdot$cm n-doped silicon chip, wherein the quantum resonance switching-on is about at 0.01 nA and the quantum resonance switching-off is about at −0.07 nA toward quantum standard and the area of quantum tunneling current spectrum is 5000 Å×5000 Å. B, C-AFM characterizes the bi-stable quantum tunneling current at the maximum value about 45 pA and the minimum value about −45 pA and single electron spin hysteresis I-V curve of FIG. 1$a$ within ±6V bias potentials for symmetry spin-up and spin-down qubit operator processing. C, The 1st derivative of 1$b$ corresponds to bi-stable spin-up and spin-down transports as well as quantum resonance tunneling peaks at ±2V bias potential for qubit memory in the dI/dV conductance spectrum, revealing the weak spin-orbital and hyperfine hybrid of molecular scale quantum and/or magnetic tunnel junctions (QTJs and/or MTJs) to be used as promising ultra thin/small spintronic devices. D, The double-peaked laser micro-PL spectrum of symmetry photoelectron coupling and 70D magnetic field-toned redox nanomedicine quantum dot room temperature superconductor qubit networks in energy-frequency-phase and energy-time-phase spectra, wherein data are profiled as an average PL spectra of 23 measurements with s.d. onto the n-doped silicon chip, and $\hbar$-related photoelectron coupling- and/or co-tunneling-driven ±2364 qubit networks meet the binary code matrix of room temperature superconductor qubit network Hamiltonians as follow. H=$\Sigma\{(2^n), n=...3, 4...\}$ (1) for 2 one-level symmetry spin-down and spin-up $\pm\frac{1}{2}\pi N$ Hadamard and/or Pauli Z-gated qubit operator networks and one two-level symmetry spin-down and spin-up XOR-gated qubit operators with an initially unitary qubit operator |1>, 16 operator carries for 1 two-level qubit permutations and 8 operator carries for 2 one-level qubit operator network permutations in a sum of ±2 and double (±8, ±16) operators in a sum of ±2364 spin-down and spin-up phase transition degrees with $\pm\frac{1}{2}\pi N$ angular momentum.
Figure 1B:
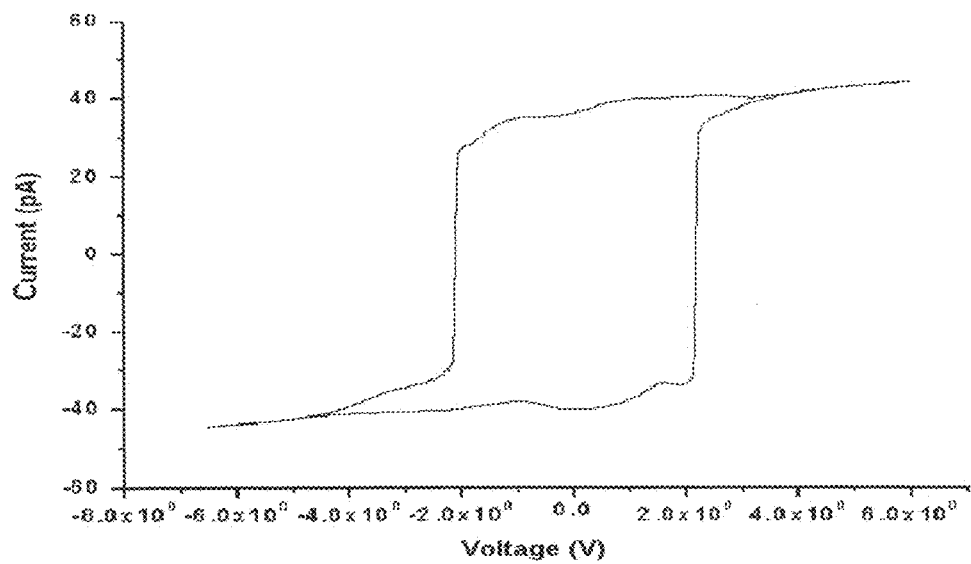
Figure 1C:
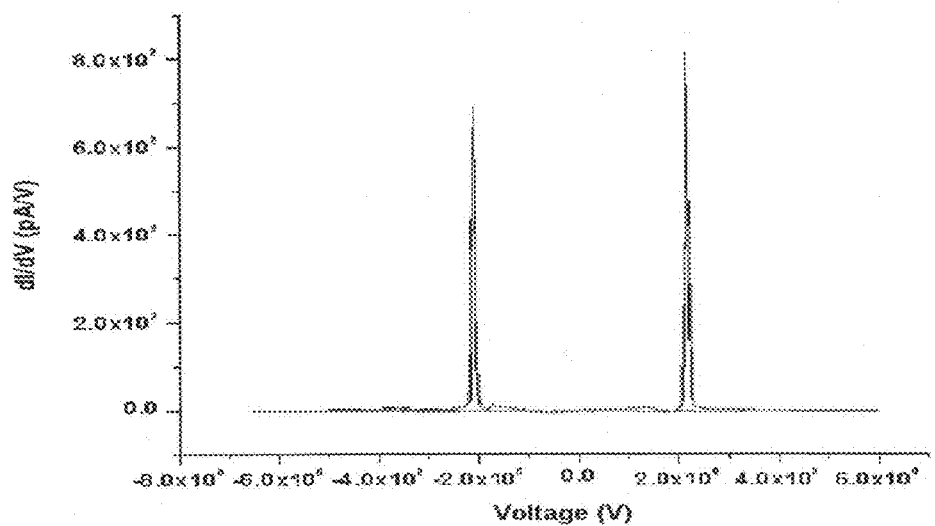

Turning self-assembled pharmaceuticals and a bio-redox single electron system into redox nanomedicine quantum dot room temperature superconductor qubit networks onto graphite and silicon substrates under a 10 class clean environment and a spatial distance constraint of 0.1 Å-200 Å including unitary, binary, ternary, quaternary quinary and hexahedral complexes described herein demonstrate electrostatic stacked coordinate of an antioxidase antioxidant, agonists of β-adrenergic and $P_2$ purinergic receptors, a phenylalkylamine (benzalkonium) calcium channel blocker and/or a bio-redox single electron system of either XO:X or X from a liquid phase state to a co-crystallized soft condensate state according to the $L_{16}(2)^{15}$ and $L_9(3)^4$ orthogonal methods in the paragraph [0004].

Advantageous compositions of turning self-assembled pharmaceuticals and a bio-redox single electron system into molecular scale size-controllable redox nanomedicine quantum dot room temperature superconductor qubit networks with cross-bar, hexahedral stacked, electrostatic hybrid geometrical nanometer architectures include isoprenaline molecular numbers in a range of about single molecule to about $10^{15}$, adenosine triphosphate in a range of about single molecule to about $10^{19}$, verapamil in a range of about single molecule to about $10^{14}$, and/or superoxide dismutase in a range of about single molecule to about $10^{13}$, each pharmaceutical ingredient and its binary, ternary and/or quaternary complexes is combined with either bio-redox single electron system of XO:X in a molecular mixture ratio of 1:20, wherein the molecular number of X may be in a range of about 1-20 single molecules to about $3\times10^{16}$-$3\times10^{19}$ in a liquid phase. This liquid pharmaceutical composition targets hypoxia-mediated key loops in cardiopulmonary and cerebral functional disorders and/or carcinoma metastasis, including the decline in β-adrenergic and $P_2$-purinergic receptor signal transduction, superoxide anion induced endothelial injuries, and an elevated intracellular calcium influx.

This preparation process employs molecular scale coordinates to self-assemble unitary, binary, ternary, quaternary, quinary and/or hexahedral redox nanomedicine quantum dot room temperature superconductor qubit networks in the cross-bar electrostatic and hexahedral-stacked quantum and/or magnetic tunnel junctions (QTJs and/or MTJs) patterns through either droplets onto the substrates or immersing substrates in the unitary, binary, ternary, and/or quaternary pharmaceutical standard solutions of isoprenaline, verapamil, superoxide dismutase, and/or adenosine triphosphate in combination with a bio-redox single electron system of XO:X or X alone according to the $L_{16}(2)^{15}$ and the $L_9(3)^4$ orthogonal design protocols. The electrostatic cross-bar stacked and hexahedral 3D geometrical architectures and their preparation process are advantageous for nano-drug discovery and high density and high performance quantum bit informatics devices as well as photoelectron sensing materials.

The molecular scale electrostatic stacked quantum and/or magnetic tunnel junction (QTJ and/or MTJ) and (QCA) property of the redox nano-medicine quantum dot room temperature superconductor qubit networks is presented by the bio-redox single electron spin-up and spin-down tunneling transports resulting from tunneling of electron spin-up into the upper layer electrostatic stacked quantum dots and tunneling of electron spin-down into the lower layer electrostatic stacked quantum dots state in I-V curves, their first derivatives, laser micro-PL spectra, their FFTs and their first derivatives of relative phases and FFTs in frequency and time domains that are $\hbar$-related QCVs, including angular momentum of single electron spins, amplitude of quantum waves, phase transition dynamics of qubit operator networks within a range of about nHz to about pico-seconds with about sub-$10^{-19}$ eV energy fluctuations.

The feature of the redox nano-medicine quantum dot room temperature superconductor qubit networks is identified by $\hbar$-related $\pm\frac{1}{2}\pi N$ symmetry or non-symmetry spin-down and spin-up phase transition degrees that satisfy $\pm\frac{1}{2}\pi N$ Hadamard and/or Pauli Z-gated qubit operator networks and two-level symmetry spin-down and spin-up XOR-gated qubit operator networks with carries, spin echo and unitary qubit operators. All symmetry or non-symmetry spin-down and spin-up phase transition degrees satisfy $\hbar$-related binary code matrix of Hamiltonians in a superconductor qubit operator network manner of either $\Sigma 2^n$, $\Sigma 2^2 \cdot 2^n$, $\Sigma 2^{n+1}$, $\Sigma 2^{2n} \cdot 2^{2n}$, $\Sigma 2^{2n+1} \cdot 2^{2n+1}$ or $\Sigma 2^{2n+1}$.

The $\hbar$-related qubit metrology in the invention is a measurement method standard of C-AFM and laser micro-PL spectrum in combination with the $L_{16}(2)^{15}$ and $L_9(3)^4$ orthogonal optimization methods, and ORIGIN mathematical analyses (available from OriginLab Co., Northampton, Mass.), comprising calibration of C-AFM tip and laser micro-PL spectrum system as well as standard samples under clean and dry environments, no vibrations and no noise interference, as well as non-contact tip modes to secure reproducible and traceable as well as convincible with err bars and statistical significance P value tests.

A key composition of this invention is the optimum self-assembly of uni-, bi-, tri-, tetra-, quin- and/or hexa-elements of isoprenaline (a β-adrenergic receptor agonist), adenosine triphosphate (a $P_2$-purinergic receptor agonist), verapamil (a phenylalkylamine calcium channel blocker), superoxide dismutase (an antioxidase antioxidant) and/or a bio-redox single electron system of XO and X respectively at a desire molecular mixture ratio through controlling the spatial distance constraint of 0.1 Å-200 Å in the liquid phase for a desired period under a 10 class clean environment to secure single molecular scale electrostatic stacked 3D nanometer co-crystallized quantum dot room temperature superconductor qubit network architectures onto the substrates in the $L_{16}(2)^{15}$ and $L_9(3)^4$ orthogonal design protocols.

Unitary redox nanomedicine quantum dot room temperature superconductor qubit networks are respectively self-assembled onto substrates of either the 8-12 Ω·cm p-doped silicon surface with hydrogen bonds, the 0.01-0.05 Ω·cm n-doped silicon surface with the hydrogen bonds or the clean graphite surface, under a 10 class clean environment for a desired time period of either about 30-60 minutes onto the graphite substrate at room temperature or about 8-12 hours onto the silicon substrates at from −4° C. to −20° C., according to (i) 1:0:0:0; (ii) 0:1:0:0; (iii) 0:0:1:0; and/or (iv) 0:0:0:1 complex molecular mixture preparation processes of a bio-redox single electron-pharmaceutical hybrid system, wherein redox pharmaceutical ingredients comprise verapamil, isoproterenol, superoxide dismutase, adenosine triphosphate in combination with either XO:X in a 1:20 molecular mixture ratio or X through 0.1 Å-200 Å spatial distance constraint in the liquid phase for 3D stacked molecular architectures.

Binary redox nanomedicine quantum dot room temperature superconductor qubit networks are respectively fabricated onto the p-doped (8-12 Ω·cm) or the n-doped (0.01-0.05 Ω·cm) silicon substrate are respectively fabricated onto substrates of either the 8-12 Ω·cm p-doped silicon surface with hydrogen bonds, the 0.01-0.05 Ω·cm n-doped silicon surface with the hydrogen bonds or the clean graphite surface, under a 10 class clean environment for a desired time period of either about 30-60 minutes onto the graphite substrate at room temperature or about 8-12 hours onto the silicon substrates at from −4° C. to −20° C., according to (i) 1:1:0:0; (ii) 1:0:1:0; (iii) 1:0:0:1; (iv) 0:1:1:0; (v) 0:1:0:1 and/or (vi) 0:0:1:1 complex molecular mixture preparation processes of a bio-redox single electron-pharmaceutical hybrid system, wherein redox pharmaceutical ingredients comprise verapamil, isoproterenol, superoxide dismutase, adenosine triphosphate in combination with either XO:X in a 1:20 molecular mixture ratio or X through 0.1 Å-200 Å spatial distance constraint in the liquid phase for 3D stacked molecular architectures.

Ternary redox nanomedicine quantum dot room temperature superconductor qubit networks are respectively manufactured onto substrates of either the 8-12Ω·cm p-doped silicon surface with hydrogen bonds, the 0.01-0.05 Ω·cm n-doped silicon surface with the hydrogen bonds or the clean graphite surface, under a 10 class clean environment for a desired time period of either about 30-60 minutes onto the graphite substrate at room temperature or about 8-12 hours onto the silicon substrates at −4° C.--20° C., according to (i) 1:1:1:0; (ii) 1:0:1:1; (iii) 1:1:0:1; and/or (iv) 0:1:1:1 complex molecular mixture preparation processes of a bio-redox single electron-pharmaceutical hybrid system, wherein redox pharmaceutical ingredients comprise verapamil, isoproterenol, superoxide dismutase, adenosine triphosphate in combination with either XO:X in a 1:20 molecular mixture ratio or X through 0.1 Å-200 Å spatial distance constraint in the liquid phase for 3D stacked molecular architectures.

Quaternary redox nanomedicine quantum dot room temperature superconductor qubit networks are respectively synthesized onto substrates of either the 8-12 Ω·cm p-doped silicon surface with hydrogen bonds, the 0.01-0.05 Ω·cm n-doped silicon surface with the hydrogen bonds or the clean graphite surface, under a 10 class clean environment for a desired time period of either about 30-60 minutes onto the graphite substrate at room temperature or about 8-12 hours onto the silicon substrates at −4° C.--20° C., according to (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; and/or (ix) 3:3:2:1 complex molecular mixture preparation processes of a bio-redox single electron-pharmaceutical hybrid system, wherein redox pharmaceutical ingredients comprise verapamil, isoproterenol, superoxide dismutase, adenosine triphosphate in combination with either XO:X in a 1:20 molecular mixture ratio or X through 0.1 Å-200 Å spatial distance constraint in the liquid phase for 3D stacked molecular architectures.

The I-V curves, the laser micro-PL spectra, their FFTs, their first derivatives of relative phases in frequency and time domains (dr/df=E/ℏ and dr/dt=E/ℏ for ℏ-related QCVs) and their FFTs of self-assembled unitary, binary, ternary, quaternary, quinary and hexahedral complexes of this invention can generate 24 arrays of composition data and 24 size-controlled molecular scale stacked patterns at a nanometer and/or an atomic level. The 3D topographic structures of redox nanomedicine quantum dot room temperature superconductor qubit networks may be identified by C-AFM images, as shown in FIGS. 1-6. The spatial stacked sizes of redox nanomedicine quantum dot room temperature superconductor qubit networks may be in a range of about one angstrom to about a few hundred angstroms. The finest redox nanomedicine quantum dot room temperature superconductor qubit networks may be about 26 angstroms. The smallest spatial size of a size-controlled molecular scale stacked redox nanomedicine quantum dot room temperature superconductor qubit network topographic structure may be sub-angstroms about 0.8 Å.

The self-assembled redox nanomedicine quantum dot room temperature qubit networks possess hexahedral stacked molecular networks and 3D cross-bar shape, as well as controllable ultra-fine QTJs and/or MTJs with ℏ-related single electron spin tunneling and/or photon-electron coupling/co-tunneling into the 3D electro-statically coupled quantum dot networks, as shown by their topographic structure images, current spectra, I-V curves and double-peaked PL spectra as well as their QCVs in FIG. 1a-d, FIG. 2a-d, FIG. 3a-d, FIG. 4a-f and FIG. 5a-i. This invention is advantageous in molecular scale electronics and quantum bit memory devices as well as new nanometer scale bio-photoelectron sensors.

The preparation process is to lay out redox nanomedicine quantum dot matrix of single molecular scale π-π stacked enzyme-pharmaceutical-nuclear acid hybrid mono-layer networks onto a substrate through a spatial distance constraint, bonding and anti-bonding states, π orbits of $CH_2=CH—CH=CH_2$ and $—N=N—$, and non-bonding n orbits of $—OH$, $—NH_2$ and/or $—Cl$, as well as single photon donors-receptors of $N—$ and $NH_2—$ contained aromatic structures within redox nanomedicine molecules in a clean environment. Droplets of Pharmaceuticals are prepared according to pharmaceutical standards, which may refer to the SFDA issued by the Ministry of Health in China. Droplets of nanomedicine are made by the uni-, bi-, tri-, tetra-, quin- and/or hexa-hybrid of verapamil hydrochloride, isoprenaline hydrochloride, superoxide dismutase, and adenosine triphosphate in combination with a bio-redox single electron system of either XO:X or X at a desire molecular mixture ratio. Layouts of redox nanomedicine quantum dot room temperature superconductor qubit networks onto substrates are according to $L_{16}(2)^{15}$ and $L_9(3)^4$ orthogonal design protocols in a liquid phase for a desired period by modulating spatial distance constraints in a range of about 0.1 Å to about 200 Å under a clean environment about 10 class, wherein the uni-, bi-, tri-, tetra-, quin- and/or hexa-hybrid of verapamil hydrochloride, isoprenaline hydrochloride, superoxide dismutase, and adenosine triphosphate in combination with a bio-redox single electron system of either XO:X or X are secured to be stacked in an electrostatic contact manner. A unitary, binary, ternary, quaternary, quinary and/or hexahedral redox nanomedicine quantum dot room temperature superconductor qubit network may be formed onto a substrate of either a graphite, a 8-12 Ω·cm p-doped silicon chip with H-bonds or a 0.01-0.05 Ω·cm n-doped silicon chip with H-bonds for either 30-60 minutes at room temperature, 8-12 hours or 96 hours around −4° C.--20° C. by a droplet hetero-molecular core-shell quantum dot lattice epitaxy in a desired molecular scale mixture ratio under a 10-class clean environment.

Figure 1D:
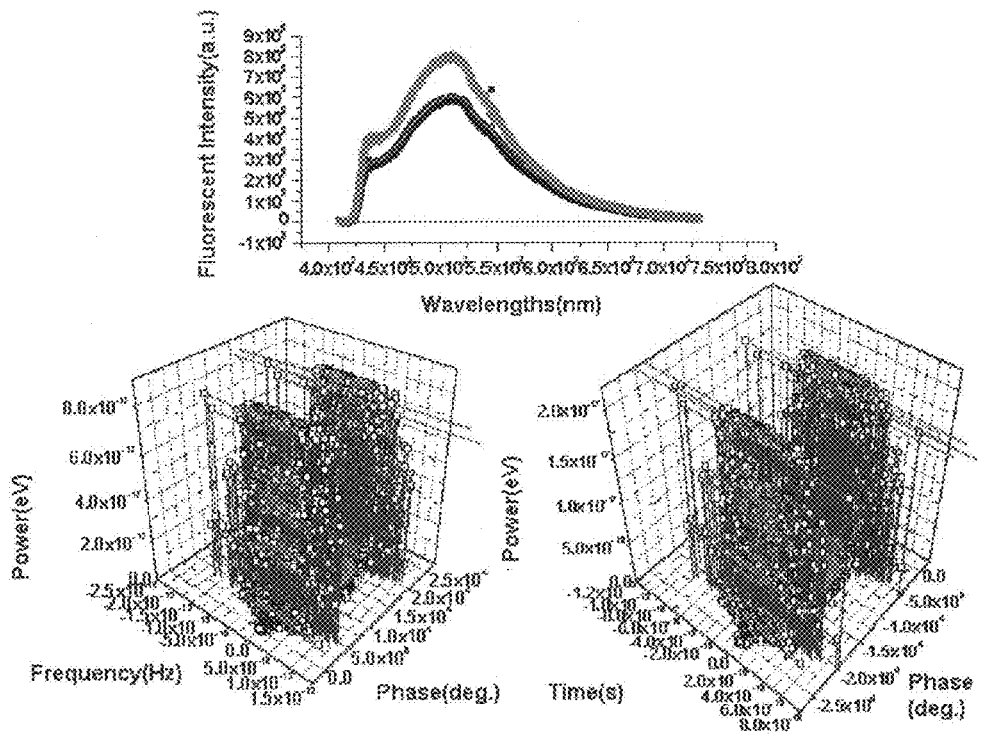

A unitary, binary, ternary, quaternary, quinary and/or hexahedral droplet hetero-molecular core-shell quantum dot lattice epitaxy may comprise verapamil hydrochloride, isoprenaline hydrochloride, superoxide dismutase, and adenosine triphosphate in combination with a bio-redox single electron system of either XO:X or X in a desired molecular mixture ratio according to $L_{16}(2)^{15}$ and $L_9(3)^4$ orthogonal design protocols through hetero-molecular-crystal lattice epitaxy spatial distance constraints in a range of about 0.1 Å to about 200 Å.

A unitary desired molecular number of a hybrid redox nanomedicine droplets for hetero-molecular core-shell quantum dot lattice epitaxy may be according to (i) 1:0:0:0; (ii) 0:1:0:0; (iii) 0:0:1:0; (iv) 0:0:0:1; and combinations thereof, in an $L_{16}(2)^{15}$ orthogonal design protocol, wherein verapamil hydrochloride droplet may be in a range of about single molecules to about $10^{14}$; a unitary desired molecular number of a isoprenaline hydrochloride droplet may be in a range of about single molecules to about $10^{15}$; a unitary desired molecular number of a superoxide dismutase buffer droplet may be in a range of about single molecules to about $10^{13}$; a unitary desired molecular number of an adenosine triphosphate buffer droplet may be in a range of about single molecules to about $10^{19}$; a desired molecular number of XO:X may be 1:20; and a desired molecular number of X may be in a range of about 1-20 single molecules to about $10^{16}$-$3\times10^{19}$.

A binary desired molecular number of a hybrid redox nanomedicine droplets for hetero-molecular core-shell quantum dot lattice epitaxy may be according to (i) 1:1:0:0; (ii) 1:0:1:0; (iii) 1:0:0:1; (iv) 0:1:1:0; (v) 0:1:0:1; (vi) 0:0:1:1, and combinations thereof, in an $L_{16}(2)^{15}$ orthogonal design protocol to mix a verapamil hydrochloride droplet in a molecular number about single molecules to about $10^{14}$, an isoprenaline hydrochloride droplet in a molecular number about single molecules to about $10^{15}$, a superoxide dismutase buffer droplet in a molecular number about single molecules to about $10^{13}$, an adenosine triphosphate buffer droplet in a molecular number about single molecules to about $10^{19}$ plus either 1:20 XO:X or X in a molecular number about 1-20 single molecules to about $3\times10^{16}$-$3\times10^{19}$.

A ternary desired molecular number of a hybrid redox nanomedicine droplets for hetero-molecular core-shell quantum dot lattice epitaxy may be according to (i) 1:1:1:0; (ii) 1:0:1:1; (iii) 1:1:0:1; and/or (iv) 0:1:1:1 and combinations thereof, in an $L_{16}(2)^{15}$ orthogonal design protocol to mix a verapamil hydrochloride droplet in a molecular number about single molecules to about $10^{14}$, an isoprenaline hydrochloride droplet in a molecular number about single molecules to about $10^{15}$, a superoxide dismutase buffer droplet in a molecular number about single molecules to about $10^{13}$, an adenosine triphosphate buffer droplet in a molecular number about single molecules to about $10^{19}$ plus either 1:20 XO:X or X in a molecular number about 1-20 single molecules to about $3\times10^{16}$-$3\times10^{19}$.

A quaternary desired molecular number of a hybrid redox nanomedicine droplets for hetero-molecular core-shell quantum dot lattice epitaxy may be according to (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; and/or (ix) 3:3:2:1 and combinations thereof, in an $L_9(3)^4$ orthogonal design protocol to mix a verapamil hydrochloride droplet in a molecular number about single molecules to about $10^{14}$, an isoprenaline hydrochloride droplet in a molecular number about single molecules to about $10^{15}$, a superoxide dismutase buffer droplet in a molecular number about single molecules to about $10^{13}$, an adenosine triphosphate buffer droplet in a molecular number about single molecules to about $10^{19}$ plus either 1:20 XO:X or X in a molecular number about 1-20 single molecules to about $3\times10^{16}$-$3\times10^{19}$.

In the $L_{16}(2)^{15}$ orthogonal design protocol, there are 4 different unitary hybrid redox nanomedicine hetero-molecular core-shell quantum dot lattice epitaxy droplets, 6 different binary hybrid redox nanomedicine hetero-molecular core-shell quantum dot lattice epitaxy droplets, 4 different ternary hybrid redox nanomedicine hetero-molecular core-shell quantum dot lattice epitaxy droplets, 1 quaternary hybrid redox nanomedicine hetero-molecular core-shell quantum dot lattice epitaxy droplets, and a blank control group. In the $L_9(3)^4$ orthogonal design protocol, there are 9 different quaternary hybrid redox nanomedicine hetero-molecular core-shell quantum dot lattice epitaxy droplets at three molecular mixture ratios. Hybrid redox nanomedicine hetero-molecular core-shell quantum dot lattice epitaxy droplets are the unitary, binary, ternary and quaternary nanomedicine in combination with 1:20 XO:X or X.

The uni-, bi-, tri-, tetra-, quin- and/or hexa-hybrid redox nanomedicine hetero-molecular quantum dot lattice epitaxy droplets may assembly as redox nanomedicine quantum dot room temperature superconductor qubit networks, wherein a redox nanomedicine hetero-molecular core-shell quantum dot lattice, a three-quantum particle transistor and a qubit central processor unit may be included.

Example 1

Pharmaceutical liquids are prepared according to the pharmaceutical standards, which may refer to the SFDA issued by the Ministry of Health in China. FIG. 1*a-d* is drawings of a C-AFM current spectrum, a I-V curve, a dI-dV conductance spectrum, and an average laser micro-PL spectra as well as ℏ-related power-frequency-phase and power-time-phase spectra derived from the $1^{St}$ derivatives of relative phase FFTs obtained from the 0:1:0:0 product of Example 1 according to the $L_{16}(2)^{15}$ orthogonal design protocol under a 10 class clean environment.

i. An isoprenaline hydrochloride pharmaceutical liquid is prepared at a concentration of 2 mg/100 mL.
ii. An isoprenaline hydrochloride pharmaceutical droplet may comprise the molecular number of about $10^{14}$ isoprenaline hydrochloride molecules to about $10^{15}$ isoprenaline hydrochloride molecules.
iii. A bio-redox single electron system is made in physiological buffer solution of xanthine oxidase (XO) and xanthine (X) according to a 1:20 molecular mixture ratio, and the desired molecular xanthine number may be in a range of about $3\times10^{16}$ X molecules to about $3\times10^{19}$ X molecules.
iv. A droplet of XO-X-isoproterenol hydrochloride hybrid is prepared onto a 0.01-0.05 Ω·cm n-doped silicon substrate surface according to a desired molecular mixture ratio of 0:1:0:0 in the $L_{16}(2)^{15}$ by controlling the spatial distance of 0.1 Å-200 Å at −20° C. for 8-12 hours, up to forming to a redox nano-drug quantum dot network lattice through a droplet crystal lattice hetero-epitaxy bottom-up self-assembly approach.
v. At a room temperature and in air, C-AFM is used for imaging the topographic structure and current spectrum of a self-assembled redox nano-drug quantum dot network lattice, probing its I-V curve and the $1^{st}$ derivative of I-V curve (dI/dV), as shown in FIG. 1*a-c*.

vi. At a room temperature and in air, a laser micro-PL spectrum system tool characterizes an average PL spectrum with standard deviation (s.d.), and $\hbar$-related symmetry spin-down and spin-up qubit network and its operator permutations in $\hbar$-related power-frequency-phase and power-time-phase spectra, as indicated in FIG. 1d.

Example 2

Figure 2A:
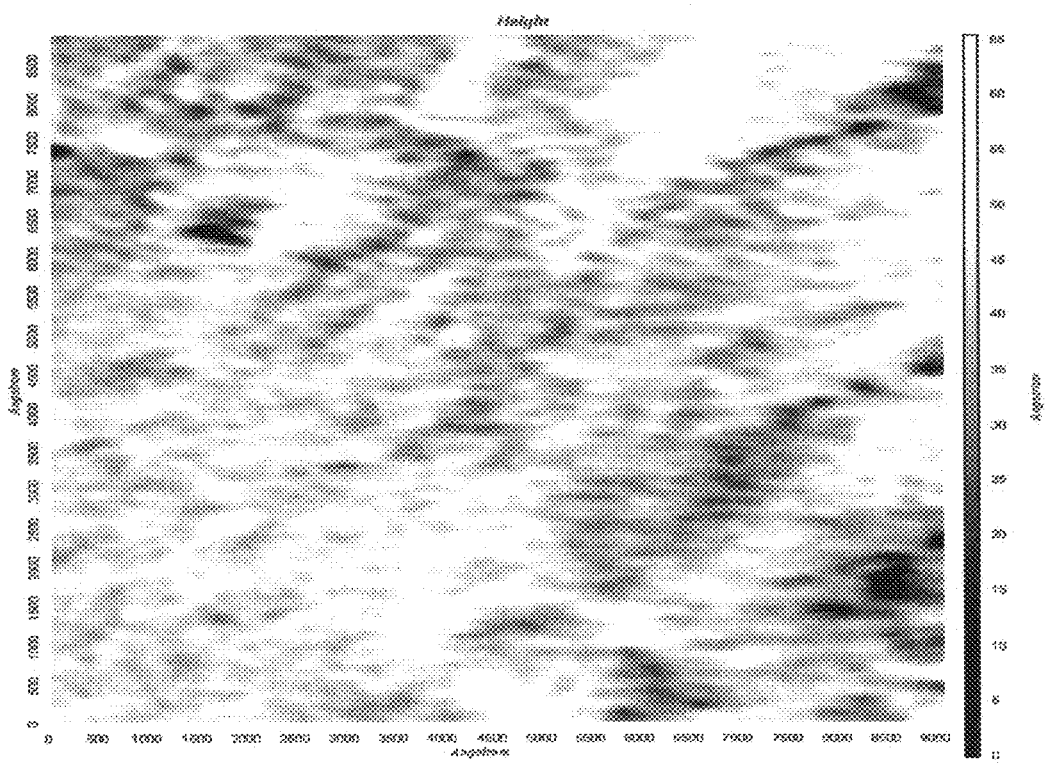
FIG. 2. A, C-AFM characterizes topographic structure of a self-assembled redox nanomedicine quantum dot room temperature superconductor qubit network onto the 0.01-0.05 $\Omega\cdot$cm n-doped silicon chip, according to a molar ratio of 1:1:1:1 in the $L_{16}(2)^{15}$ orthogonal design model, wherein its 3D hexahedral size is stacked as a length 9000 Å, a width 9000 Å and a height 65 Å. B, The average double-peaked PL spectrum of FIG. 2$a$ reveals an optical quantum property, wherein photon-electron-magnetic external field-toned symmetry and atomic scale non-symmetry photoelectron coupling effects are profiled in the average laser micro-PL spectra of 99 optical quantum feature measurements with s.d. under toned spinning magnetic fields of respectively using either 70D, 70D150t, 98D, 101D, 104D, 109D, 113D, 117D, RTD10t, RTD50t or RTD110t. Statistical significance P<0.01 are showed by error bars thereof. C, A paradigm of spinning magnetic field-toned redox nano-medicine quantum dot room temperature superconductor qubit networks associate non-symmetry spin-down QCVs in the $\hbar$-related energy-frequency-phase spectrum that corresponds to FIG. 2b. D, A paradigm of spinning magnetic field-toned redox nano-medicine quantum dot room temperature superconductor qubit networks associate non-symmetry spin-up QCVs in the $\hbar$-related energy-time-phase spectrum that corresponds to FIG. 2b. C and D, The average room temperature qubit operators of FIG. 2b are achieved at symmetry spin-down and spin-up ±4302 phase transition degrees, wherein spin-down and spin-up qubit operator networks satisfy the binary code matrix of room temperature superconductor qubit operator network Hamiltonian as follows. $H=\Sigma\{(2^{n+1}), n=0, 1, 2, 3, 4\}$(1) for 3 one-level symmetry spin-down and spin-up $\pm\frac{1}{2}\pi N$ Hadamard and/or Pauli Z-gated qubit operator networks and 2 two-level symmetry spin-down and spin-up XOR-gated qubit operator networks with an initially unitary qubit operator $|0\rangle$, carries 64 operators for 4 two-level XOR-gated qubit operator permutations and carries 8 operators for 2 one-level Hadamard and/or Pauli Z-gated qubit operator permutations with $\pm\frac{1}{2}\pi N$ angular momentum. The following binary code matrix Hamiltonians respectively correspond to 11 different types of symmetry and non-symmetry qubit operator networks within a range of about 0 Hz/s-$10^{-19}$ Hz/s frequency/time domains and an energy flipping range of 5.441E-36 eV-631,00065 eV as profiled in FIG. 2b. /1] $H=\Sigma\{(2''), n= \ldots 3, 4 \ldots\}$ for 2 one-level symmetry spin-down and spin-up $\pm\frac{1}{2}\pi N$ Hadamard and/or Pauli Z-gated qubit operator networks and 1 two-level symmetry spin-down and spin-up XOR-gated qubit operators with initial unitary qubit operators $|0\rangle$ and $|1\rangle$, and 1 spin-down and spin-up qubit operator carry $|0\rangle$ in a sum of ±1, ±2, ±8, ±16 qubit operators with ±1 carry with $\pm\frac{1}{2}\pi N$ angular momentum, which corresponds to the 70D toned PL spectrum with phase transition degrees of (0, ±2440). [2] $H=\Sigma\{(2''), n= \ldots 3, 4 \ldots\}$ for 2 one-level symmetry spin-down $\frac{1}{2}\pi N$ Hadamard and/or Pauli Z-gated qubit operator networks and 1 two-level symmetry spin-down XOR-gated qubit operators with initial unitary qubit operators $|0\rangle$, and 4 carries for 1 one-level qubit operator permutations with $\frac{1}{2}\pi N$ angular momentum; and 2 one-level symmetry spin-up-$\frac{1}{2}\pi N$ Hadamard and/or Pauli Z-gated qubit operator networks and 1 two-level symmetry spin-up XOR-gated qubit operators with initial unitary qubit operators $|0\rangle$, and spin echo ($\pi$) for qubit networks, which corresponds to 70D150t toned PL spectrum with phase transition degrees of (180, +2254, -2250) with -$\frac{1}{2}\pi N$ angular momentum. [3] $H=\Sigma\{(2''), n= \ldots 3, 4 \ldots\}$ for 2 one-level symmetry spin-down and spin-up $\pm\frac{1}{2}\pi N$ Hadamard and/or Pauli Z-gated qubit operator networks and 1 two-level symmetry spin-down and spin-up XOR-gated qubit operators with an initial qubit operator $|1\rangle$, and 6 carries for permutations of one-level and/or two-level qubit operators with $\pm\frac{1}{2}\pi N$ angular momentum, which corresponds to 98D toned PL spectrum with phase transition degrees of (0, ±2400). [4] $H=\Sigma\{(2''), n=1, 2, 3, 4, \ldots 9\}$ for 3 one-level spin-down $\frac{1}{2}\pi N$ Hadamard and/or Pauli Z-gated qubit operator networks and 17 two-level spin-down XOR-gated qubit operator networks with a unitary qubit $|1\rangle$, and 7 carries for permutations of one-level and/or one-level qubit operators in a sum of 48787 phase transition degrees with $\frac{1}{2}\pi N$ angular momentum; for 17 two-level spin-down XOR-gate qubit operator networks with a unitary qubit $|1\rangle$, and 18 carries for permutations of one-level and/or two-level qubit operations in a sum of 21798 phase transition degrees; $H=\Sigma\{(2''), n=1, 2, \ldots 5, 6, \ldots 12\}$ for 1 one-level spin-down $\frac{1}{2}\pi N$ Hadamard and/or Pauli Z-gated qubit operators and 262 two-level XOR-gate qubit operator networks with a unitary qubit $|1\rangle$, and 1 carry, as well as double spin echo ($\pi$) at initial and end of spin-down qubit operators in a sum of (180, 48787, 21798, 387173, 180) operators with $\frac{1}{2}\pi N$ angular momentum; $H=\Sigma\{(2''), n=1, \ldots 3, 4, \ldots 9\}$ for 2 one-level spin-up -$\frac{1}{2}\pi N$ Hadamard and/or Pauli Z-gated qubit operator networks and 33 two-level spin-up XOR-gated qubit operator networks with a unitary qubit $|1\rangle$, and 7 carries for permutations of one-level and/or two-level qubit operators in a sum of -48427 phase transition degrees with -$\frac{1}{2}\pi N$ angular momentum; $H=\Sigma\{(2''), n=1, \ldots 4, 5, 6, \ldots 8, \ldots 11\}$ for 151 two-level spin-up XOR-gated qubit operator networks with a unitary qubit $|1\rangle$ in a sum of -217620 phase transition degrees; $H=\Sigma\{(2''), n=1, 2, \ldots 7, \ldots 11\}$ for 1 one-level spin-up -$\frac{1}{2}\pi N$ Hadamard and/or Pauli Z-gated qubit operators and 264 two-level spin-up XOR-gated qubit operator networks with unitary qubit operators $|1\rangle$ and $|0\rangle$, and 23 carries for permutations of two-level and/or one-level qubit operators in a sum of -380813 phase transition degrees, as well as double spin echo ($\pi$) at spin-up initial and end qubit operators with -$\frac{1}{2}\pi N$ angular momentum, which corresponds to 101D toned PL spectrum with a total sum of (180, -48427, -217620, -380813, 180) phase transition degrees. [5] $H=\Sigma\{(2''), n= \ldots 3, 4\}$ for 2 one-level spin-down $\frac{1}{2}\pi N$ Hadamard and/or Pauli Z-gated qubit operator networks and 1 two-level spin-down XOR-gated qubit operators with unitary qubit operators $|1\rangle$ and $|0\rangle$, and 44 carries for permutations of 2 two-level and 2 one-level spin-down qubit operations plus double spin echo ($\pi$) at initial and end spin-down qubit operators in a sum of (180, 2474, 180) phase transition degrees with $\frac{1}{2}\pi N$ angular momentum; $H=\Sigma\{(2''), n=1\}$ for a unitary qubit operator $|1\rangle$ with 67 carries for permutations of 8 two-level and/or one-level spin-up qubit operators, and double spin echo ($\pi$) at initial and end spin-up qubit operators in a sum of (180, -247, 180) phase transition degrees; all of the non-symmetry spin-down and spin-up qubits and quaternary spin echo corresponds to 104D toned PL spectrum with a total sum of (180, 2474, 180, 180, -247, 180) phase transition degrees. [6] $H=\Sigma\{(2''), n= \ldots 3, 4, \ldots 11\}$ for 2 one-level symmetry spin-down and spin-up $\pm\frac{1}{2}\pi N$ Hadamard and/or Pauli Z-gated qubit operator networks and 257 two-level symmetry spin-down and spin-up XOR-gated qubit operator networks with $\pm\frac{1}{2}\pi N$ angular momentum, which corresponds to 109D toned PL spectrum with a sum of (0, ±186480) phase transition degrees. [7] $H=\Sigma\{(2''), n= \ldots 3, \ldots 5, 6, \ldots 8\}$ for 2 one-level symmetry spin-down and spin-up $\pm\frac{1}{2}\pi N$ Hadamard and/or Pauli Z-gated qubit operator networks and 42 two-level symmetry spin-down and spin-up XOR-gated qubit operator networks with $\pm\frac{1}{2}\pi N$ angular momentum, which corresponds to 113D toned PL spectrum with a sum of (0, ±32400) phase transition degrees. [8] $H=\Sigma\{(2''), n=1, 2, 3, \ldots 5, 6, \ldots 10\}$ for 3 one-level spin-down $\frac{1}{2}\pi N$ Hadamard and/or Pauli Z-gated qubit operator networks and 70 two-level spin-down XOR-gated qubit operator networks with a unitary qubit operator $|1\rangle$, and double spin echo ($\pi$) at an initial and end of spin-down qubit operations with $\frac{1}{2}\pi N$ angular momentum; and $H=\Sigma\{(2''), n=1, \ldots 3, \ldots 5, 6, \ldots 10\}$ for 2 one-level spin-up -$\frac{1}{2}\pi N$ Hadamard and/or Pauli Z-gated qubit operator networks and 70 two-level spin-down XOR-gated qubit operator networks with a unitary qubit operator $|1\rangle$, and double spin echo ($\pi$) at an initial and end of spin-up qubit operations with -$\frac{1}{2}\pi N$ angular momentum, all of them corresponds to 117D toned PL spectrum with the non-symmetry spin-down and spin-up qubit operator networks in a sum of (180, 102060, 180, 180, −101700, 180) phase transition degrees. [9] $H=\Sigma\{(2^n), n=\ldots 2, 3, 4, 5, \ldots 7\}$ for 3 one-level symmetry spin-down and spin-up $\pm\frac{1}{2}\pi N$ Hadamard and/or Pauli Z-gated qubit operator networks and 11 two-level symmetry spin-down and spin-up XOR-gated qubit operator networks with $\pm\frac{1}{2}\pi N$ angular momentum, which corresponds to RTD10t toned PL spectrum with a sum of (0, ±16965) phase transition degrees. [10] $H=\Sigma\{(2^n), n=1, \ldots 3, 4, \ldots 6, \ldots 11\}$ for 2 one-level spin-down $\frac{1}{2}\pi N$ Hadamard and/or Pauli Z-gated qubit operator networks and 133 two-level spin-down XOR-gated qubit operator networks with a unitary qubit operator $|1\rangle$, and double spin echo ($\pi$) at an initial and end of spin-down qubit operators with $\frac{1}{2}\pi N$ angular momentum; and $H=\Sigma\{(2^n), n=\ldots 2, \ldots 4, \ldots 6, \ldots 11\}$ for 1 one-level spin-up $-\frac{1}{2}\pi N$ Hadamard and/or Pauli Z-gated qubit operators and 137 two-level spin-up XOR-gated qubit operator networks with a unitary qubit operator $|1\rangle$, and double spin echo ($\pi$) at an initial and end of spin-up qubit operators, all of them corresponds to RTD50t toned PL spectrum with a sum of (180, 192420, 180, 180, −192060, 180) phase transition degrees for the non-symmetry spin-down and spin-up qubit operators and quaternary spin echoes for networks with $-\frac{1}{2}\pi N$ angular momentum; [11] $H=\Sigma\{(2^n), n=\ldots 3, \ldots 6, 7, \ldots 11\}$ for 2 one-level symmetry spin-down and spin-up $\pm\frac{1}{2}\pi N$ Hadamard and/or Pauli Z-gated qubit operator networks and 140 two-level symmetry spin-down and spin-up XOR-gated qubit operator networks with $\pm\frac{1}{2}\pi N$ angular momentum, which corresponds to RTD110t toned PL spectrum with a sum of (0, ±202320) phase transition degrees.
Figure 2B:
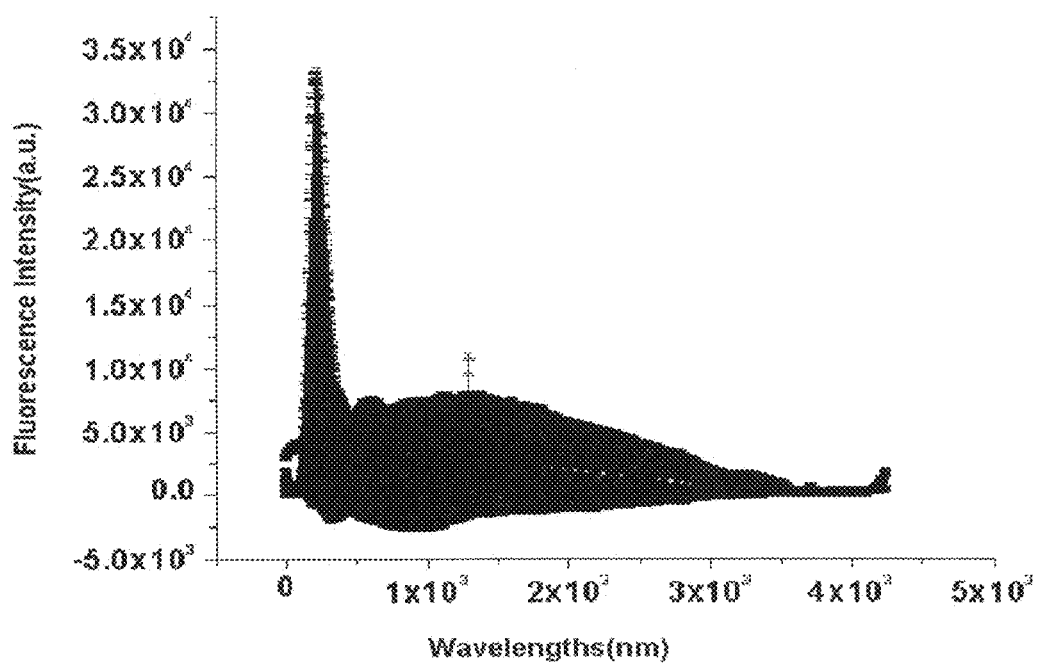
Figure 2C:
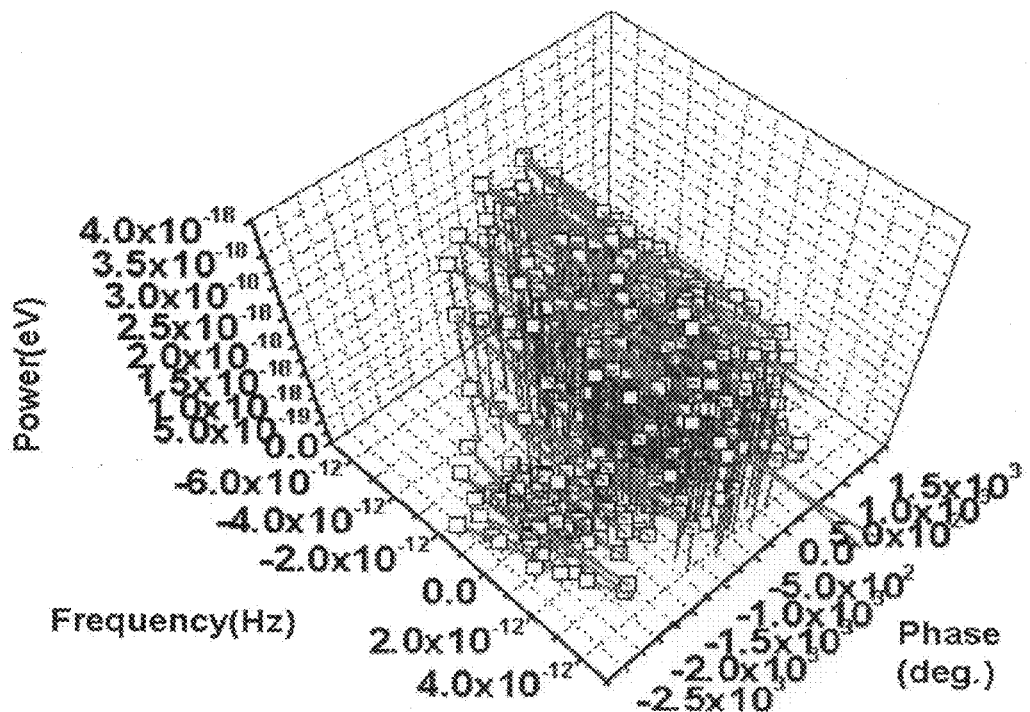
Figure 2D:
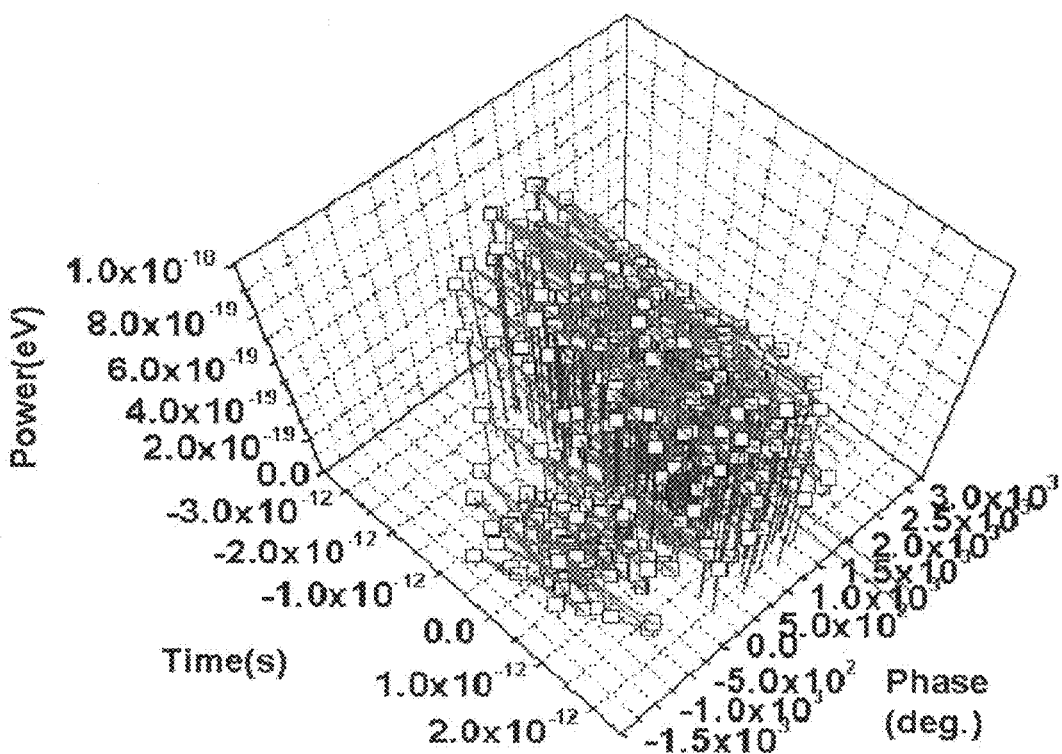

Pharmaceutical liquids are prepared according to the pharmaceutical standards, which may refer to the SFDA issued by the Ministry of Health in China. FIG. 2a-d is drawings of a C-AFM topographic structure image, average laser micro-PL spectra and $\hbar$-related symmetry and/or non-symmetry spin-down and spin-up qubit network features obtained from the 1:1:1:1 product of Example 2 according to the $L_{16}(2)^{15}$ orthogonal design protocol under a 10 class clean environment.
  i. A verapamil hydrochloride pharmaceutical liquid is prepared at a concentration of 2.5 mg/5 mL.
  ii. An isoprenaline hydrochloride pharmaceutical liquid is prepared at a concentration of 2 mg/100 mL.
  iii. A physiological buffer solution of superoxide dismutase is prepared at a concentration of 1 mg/2 mL.
  iv. A physiological buffer solution of adenosine triphosphate is prepared at a concentration of 20 mg/3.3 mL.
  v. A verapamil hydrochloride pharmaceutical droplet may comprise the molecular number of about $10^{12}$ verapamil hydrochloride molecules to about $10^{14}$ verapamil hydrochloride molecules.
  vi. An isoprenaline hydrochloride pharmaceutical droplet may comprise the molecular number of about $10^{14}$ isoprenaline hydrochloride molecules to about $10^{15}$ isoprenaline hydrochloride molecules.
  vii. A superoxide dismutase buffer droplet may consist of about $10^{11}$ superoxide dismutase molecules to about $10^{13}$ superoxide dismutase molecules.
  viii. An adenosine triphosphate buffer droplet may be made up of about $10^{11}$ adenosine triphosphate molecules to about $10^{19}$ adenosine triphosphate molecules.
  ix. A bio-redox single electron system is made in physiological buffer solution of xanthine oxidase (XO) and xanthine (X) according to a 1:20 molecular mixture ratio, and the desired molecular xanthine number may be in a range of about $3\times10^{16}$ X molecules to about $3\times10^{19}$ X molecules.
  x. A hexa-redox-pharmaceutical droplet hybrid is made by mixing v, vi, vii, viii and ix according to a desired molecular mixture ratio of 1:1:1:1 in the $L_{16}(2)^{15}$ orthogonal design protocol.
  vii. A hybrid droplet of x is prepared onto a 0.01-0.05 $\Omega \cdot$cm n-doped silicon substrate surface by controlling the spatial distance of 0.1 Å-200 Å at −20° C. for 8-12 hours, up to forming to a redox nano-drug quantum dot network lattice through a droplet crystal lattice hetero-epitaxy bottom-up self-assembly approach.
  xi. At a room temperature and in air, C-AFM is used for imaging the topographic structure of a self-assembled redox nano-drug quantum dot network lattice, as shown in FIG. 2a.
  viii. At a room temperature and in air, laser micro-PL spectrum tool is used for characterizing 70D-, 70D150t-, 98D-, 101D-, 104D-, 109D-, 113D-, 117D-, RTD10t-, RTD50t-, RTD110t-tuned an average laser micro-PL spectrum plus s.d., which is obtained from 99 measurements to acquire $\hbar$-related symmetry and non-symmetry spin-down and spin-up qubit network and its operator permutations in $\hbar$-related power-frequency-phase and power-time-phase spectra, as revealed in FIG. 2b-d.

Example 3

Figure 3A:
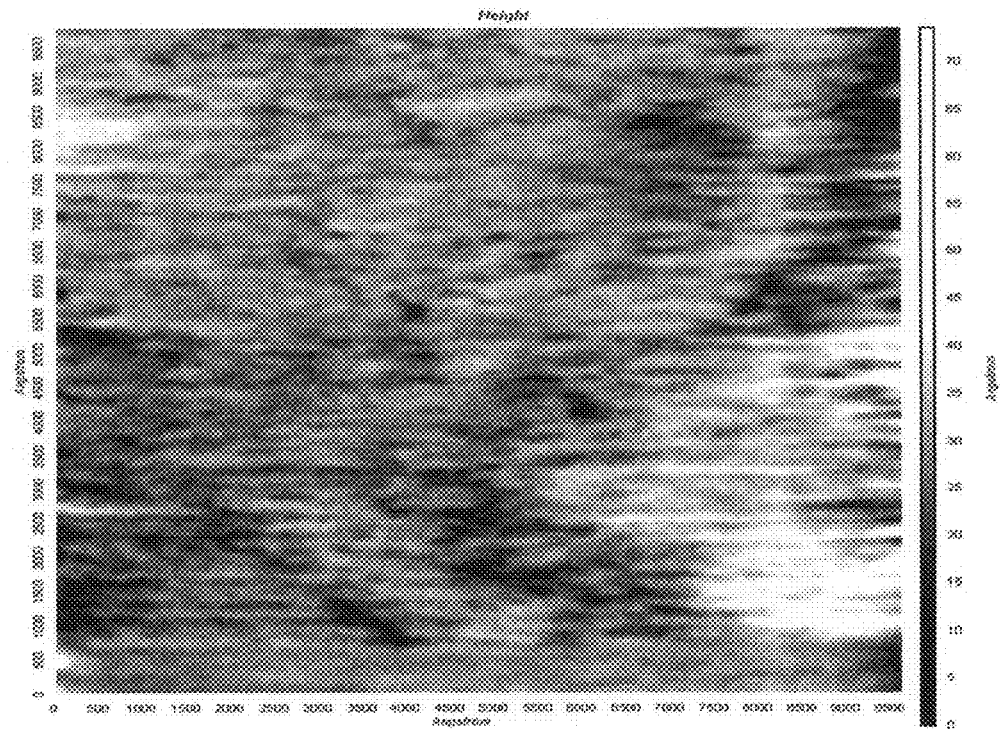
FIG. 3. A, C-AFM characterizes topographic structure of self-assembled single molecular level redox nano-medicine quantum dot room temperature superconductor qubit network onto the 0.01-0.05 Ω·cm n-doped silicon chip, according to a molecular mixture ratio of 1:1:1:1 in the $L_9(3)^4$ orthogonal design model, wherein its 3D cross-bar architecture size is stacked as a length 9500 Å, a width 9500 Å and a height 70 Å. B, 70D spinning magnetic field-toned symmetry single electron and single photon coupling effect of self-assembled single molecular level redox nano-medicine quantum dot room temperature superconductor qubit network onto the 0.01-0.05 Ω·cm n-doped silicon chip, wherein data are profiled as an average double-peaked PL spectra of 14 measurements with s.d. C and D, Single molecular level redox nano-medicine quantum dot room temperature superconductor qubit networks onto the 0.01-0.05 Ω·cm n-doped silicon chip of FIG. 3b, wherein a $\hbar$-related non-symmetry spin-up (−1884) and spin-down (+2, +2224, +2230, +2439, +2) QCVs associate with dynamics of power, frequency, time and phase transitions. The spin-up (−1884) phase transition degrees satisfy the room temperature superconductor qubit operator network Hamiltonian as follow. $H=\Sigma\{(2^2 \cdot 2^n), n=1, 2\}$ for 1 one-level spin-up $-\frac{1}{2}\pi N$ Hadamard and/or Pauli Z-gated qubit operators and 1 two-level spin-up XOR-gated qubit operators with $-\frac{1}{2}\pi N$ angular momentum. The spin-down (+2, +2224, +2230, +2439, +2) phase transition degrees satisfy the room temperature superconductor qubit operator network Hamiltonian as follow. $H=\{(2^n, n=1\}$ (1) for a unitary qubit operator $|1\rangle$ in a sum of 2 phase transition degrees. $H=\Sigma\{(2^n \cdot 2^n), n=1, 2\}$ (2) for 1 one-level spin-down $\frac{1}{2}\pi N$ Hadamard and/or Pauli Z-gated qubit operators and 1 two-level spin-down XOR-gated qubit operators with unitary qubit operators $|1\rangle$ and $|0\rangle$, and 64 carries for permutations of two-level and/or one-level spin-down qubit operators in a sum of 2224 phase transition degrees with $\frac{1}{2}\pi N$ angular momentum. $H=\Sigma\{(2^n), n=\ldots 3, 4\}$ (3) for 2 one-level spin-down $\frac{1}{2}\pi N$ Hadamard and/or Pauli Z-gated qubit operator networks and 1 two-level spin-down XOR-gated qubit operators with 7 carries for permutations of one-level and/or two-level qubit operators in a sum of 2230 phase transition degrees with $\frac{1}{2}\pi N$ phase transition degrees. $H=\Sigma\{(2^n), n=\ldots 3, 4\}$ (4) for 2 one-level spin-down $\frac{1}{2}\pi N$ Hadamard and/or Pauli Z-gated qubit operator networks and 1 two-level spin-down XOR-gated qubit operators with unitary qubit operators $|1\rangle$ and $|0\rangle$, and 9 carries for permutations of one-level and/or two-level qubit operators with $\frac{1}{2}\pi N$ phase transition degrees.
Figure 3B:
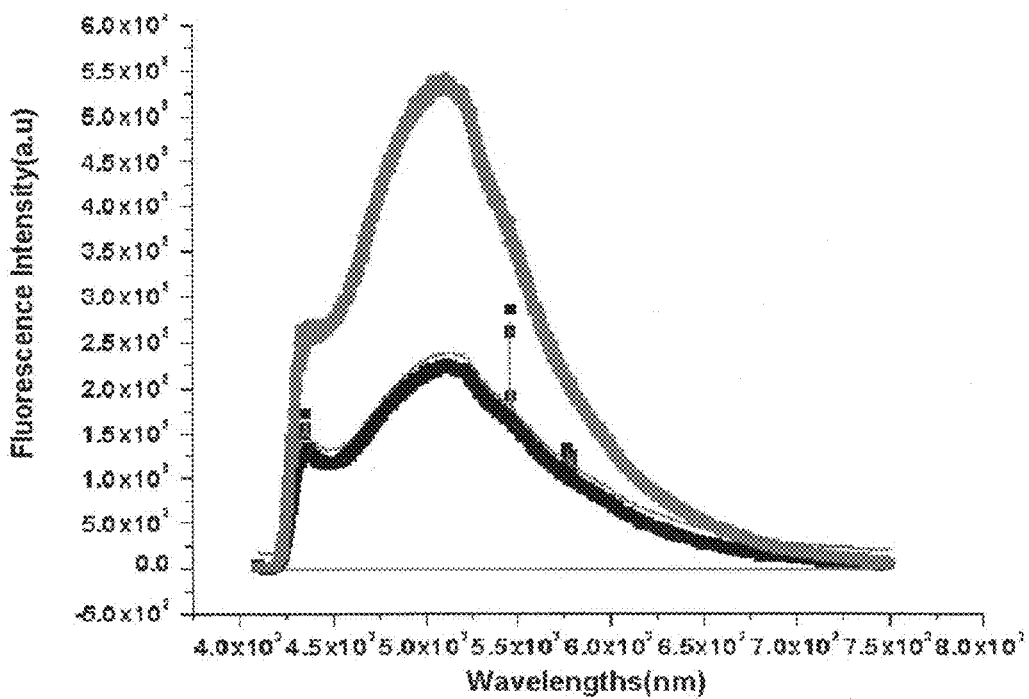
Figure 3C:
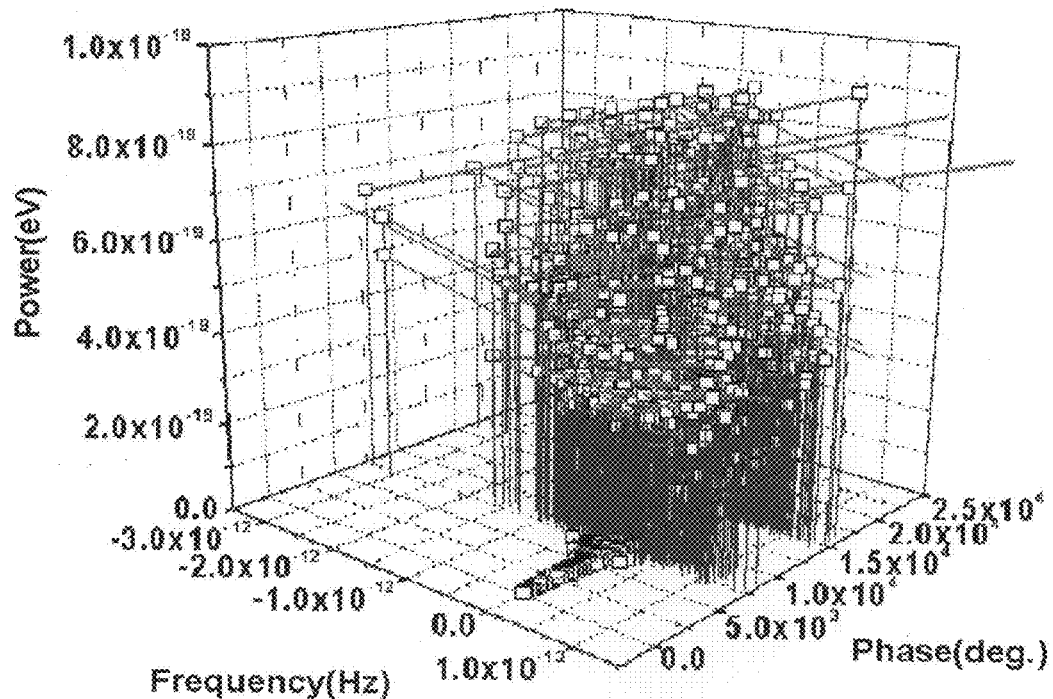
Figure 3D:
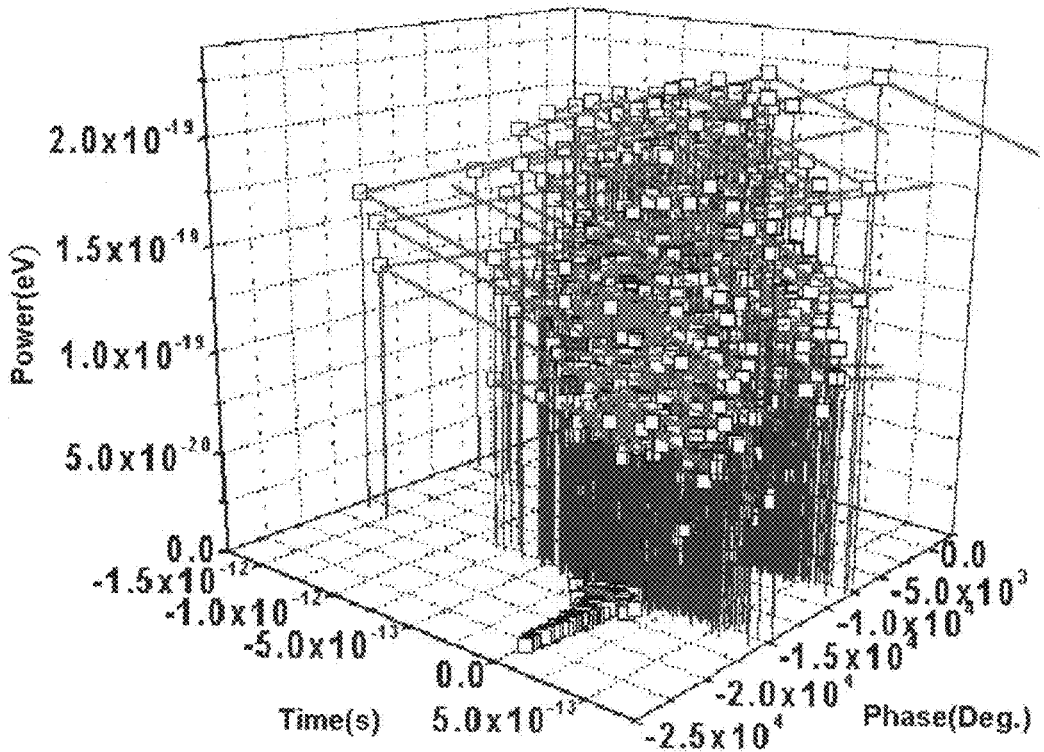

Pharmaceutical liquids are prepared according to the pharmaceutical standards, which may refer to the SFDA issued by the Ministry of Health in China. FIG. 3a-d is drawings of a C-AFM image, an average laser micro-PL spectra of 99 measurements, and $\hbar$-related non-symmetry spin-down and spin-up qubit network features obtained from the 1:1:1:1 product of Example 3 according to the $L_9(3)^4$ orthogonal design protocol under a 10 class clean environment.
  i. A verapamil hydrochloride pharmaceutical liquid is prepared at a concentration of 2.5 mg/5 mL.
  ii. An isoprenaline hydrochloride pharmaceutical liquid is prepared at a concentration of 2 mg/100 mL.
  iii. A physiological buffer solution of superoxide dismutase is prepared at a concentration of 1 mg/2 mL.
  iv. A physiological buffer solution of adenosine triphosphate is prepared at a concentration of 20 mg/3.3 mL.
  v. A verapamil hydrochloride pharmaceutical droplet may comprise the molecular number of about $10^{12}$ verapamil hydrochloride molecules to about $10^{14}$ verapamil hydrochloride molecules.
  vi. An isoprenaline hydrochloride pharmaceutical droplet may comprise the molecular number of about $10^{14}$ isoprenaline hydrochloride molecules to about $10^{15}$ isoprenaline hydrochloride molecules.
  vii. A superoxide dismutase buffer droplet may consist of about $10^{11}$ superoxide dismutase molecules to about $10^{13}$ superoxide dismutase molecules.
  viii. An adenosine triphosphate buffer droplet may be made up of about $10^{11}$ adenosine triphosphate molecules to about $10^{19}$ adenosine triphosphate molecules.
  ix. A bio-redox single electron system is made in physiological buffer solution of xanthine oxidase (XO) and xanthine (X) according to a 1:20 molecular mixture ratio, and the desired molecular xanthine number may be in a range of about $3\times10^{16}$ X molecules to about $3\times10^{19}$ X molecules.
  x. A hexa-redox-pharmaceutical droplet hybrid is made by mixing v, vi, vii, viii and ix according to a desired molecular mixture ratio of 1:1:1:1 in the $L_9(3)^4$ orthogonal design protocol.
  xi. A hybrid droplet of x is prepared onto a 0.01-0.05 $\Omega \cdot$cm n-doped silicon substrate surface by controlling the spatial distance of 0.1 Å-200 Å at −20° C. for 8-12 hours, up to forming to a redox nano-drug quantum dot network lattice through a droplet crystal lattice hetero-epitaxy bottom-up self-assembly approach.
  xii. At a room temperature and in air, C-AFM is used for imaging the topographic structure of a self-assembled redox nano-drug quantum dot network lattice, as shown in FIG. 3a.
  xiii. At a room temperature and in air, a laser micro-PL spectrum system tool characterizes an average PL spectrum with s.d., and $\hbar$-related non-symmetry spin-down and spin-up qubit network and its operator permutations in $\hbar$-related power-frequency-phase and power-time-phase spectra, as indicated in FIG. 3b-d.

Example 4

Pharmaceutical liquids are prepared according to the pharmaceutical standards, which may refer to the SFDA issued by the Ministry of Health in China. FIG. 4a-f depicts three C-AFM images (a diameter 26 Å core-shell structure single molecular scale quantum dot; a spatial size 26 Å three-particle transistor with a source, a drain and a gate made by 3 spatial size 26 Å redox nanomedicine quantum dots in a triangle pattern; and a spatial size 26 Å qubit CPU made by redox nanomedicine quantum dot networks), an average I-V curve with s.d., and $\hbar$-related electronic and qubit operator processing features obtained from the 1:3:3:3 product of Example 4 according to the $L_9(3)^4$ orthogonal design protocol under a 10 class clean environment.

i. A verapamil hydrochloride pharmaceutical liquid is prepared at a concentration of 2.5 mg/5 mL.
ii. An isoprenaline hydrochloride pharmaceutical liquid is prepared at a concentration of 2 mg/100 mL.
iii. A physiological buffer solution of superoxide dismutase is prepared at a concentration of 1 mg/2 mL.
iv. A physiological buffer solution of adenosine triphosphate is prepared at a concentration of 20 mg/3.3 mL.
v. A verapamil hydrochloride pharmaceutical droplet may comprise the molecular number of about 1 verapamil hydrochloride molecule to about 9 verapamil hydrochloride molecules.
vi. An isoprenaline hydrochloride pharmaceutical droplet may comprise the molecular number of about 1 isoprenaline hydrochloride molecule to about 9 isoprenaline hydrochloride molecules.
vii. A superoxide dismutase buffer droplet may consist of about 1 superoxide dismutase molecules to about 9 superoxide dismutase molecules.
viii. An adenosine triphosphate buffer droplet may be made up of about 1 adenosine triphosphate molecules to about 9 adenosine triphosphate molecules.
ix. A bio-redox single electron system is made in physiological buffer solution of xanthine (X) in a range of about 1 single X molecule to about 9 single X molecules.
x. A hybrid droplet of v, vi, vii, viii and ix is prepared onto a 8-12 Ω·cm p-doped silicon substrate surface by controlling the spatial distance of 0.1 Å-200 Å at −4° C. for 96 hours, up to forming to a redox nano-drug quantum dot network lattice through a droplet crystal lattice hetero-epitaxy bottom-up self-assembly approach.
xi. Washing the silicon substrate surface three times with clean de-ionized water and keeping a dry surface for measurements.
xii. At a room temperature and in air, C-AFM is used for imaging the topographic structure of a self-assembled redox nano-drug quantum dot network lattice, as shown in FIG. 4a-c, and probing an average I-V curve obtained from 6 measurements with s.d., as profiled in FIG. 4d, as well as analyzing $\hbar$-related symmetry spin-down and spin-up qubit network and its operator permutations in $\hbar$-related power-frequency-phase and power-time-phase spectra, as revealed in FIG. 4e-f.

Example 5

Figure 5A:
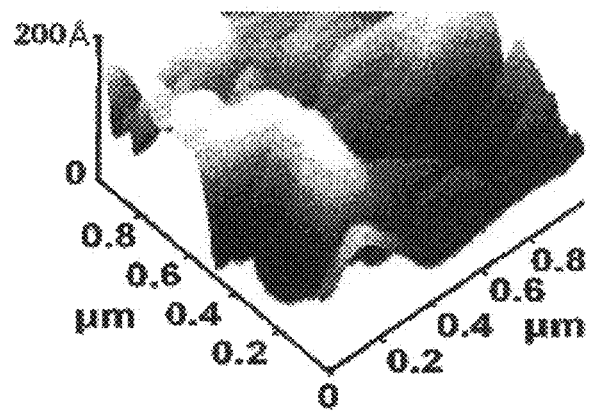
FIG. 5. A, C-AFM characterizes the topographic structure of hexa-ingredient redox nano-medicine quantum dot room temperature superconductivity network onto the graphic substrate according to the molar ratio of 1:1:1:1 in the $L_{16}(2)^{15}$ orthogonal design protocol plus the molar ratio of 1:20 bio-redox single electron system (XO:X) at room temperature and in air, wherein the cross-bar hexahedral stacked size of molecular scale quantum dot networks is a length 8000 Å, a width 8000 Å and a height 200 Å. B, C-AFM characterizes an average I-V curve of 5 measurements plus s.d. that corresponds to FIG. 5a, wherein the bi-stable quantum tunneling currents of the maximum value at about 0.65 pA that results from bio-redox single electron spin-up tunneling transport into the upper layer of stacked redox nanomedicine quantum dots and the minimum value at about −065 pA that results from tunneling of bio-redox single electron tunneling transport into the lower layer of stacked redox nanomedicine quantum dots within ±10V bias potentials and an electron spin-up and spin-down hysteresis loop of the single bio-redox electron spin transport with a spin-up current about 0.1 pA and a spin-down current about −0.05 pA within ±7.5V bias potentials are clearly shown for memory of qubits. C, The room temperature bi-stable spin-up and spin-down quantum resonance superconductivity properties of FIG. 5b are visible by a feature of superconductivity (insulator plus conductor property) with 9 spin-down and spin-up quantum resonance tunneling peaks of about 0.05 pA/V-0.2 pA/V within 0V-10V bias potentials to about 0.45 pA-0.7 pA/V within ±10V bias potentials for 9 spin-down and spin-up superconductor qubit memories at room temperature. D, The spin-down room temperature superconductivity qubit networks of FIG. 5c associate with $\hbar$-related amplitudes and angular velocities of quantum waves in frequency domain. E, The spin-up room temperature superconductivity qubit networks of FIG. 5c associate with $\hbar$-related amplitudes and angular velocities of quantum waves in time domain. F, The spin-down room temperature superconductivity qubit networks of FIG. 5d associate with $\hbar$-related QCVs in power-frequency-phase spectrum. G, The spin-up room temperature superconductivity qubit networks of FIG. 5e associate with $\hbar$-related QCVs in power-time-phase spectrum. H, The spin-down room temperature superconductivity qubit networks of FIG. 5f associate with $\hbar$-related phase transitions in frequency domain. I, The spin-up room temperature superconductivity qubit networks of FIG. 5g amplitudes associate with $\hbar$-related phase transitions in time domain.
FIG. 5e, FIG. 5g, FIG. 5h and FIG. 5i reveal single-level and two-level symmetry spin-down and spin-up room temperature superconductor qubit operator networks and operator permutations at 9 different frequency and time domains in a range of about 0.1 nHz and about 0.5 pico seconds with about $10^{-16}$ eV-$10^{-17}$ eV power fluctuations. All above operators satisfy a binary code matrix of redox nano-medicine quantum dot room temperature superconductor qubit network Hamiltonians as follows. [1] H=$\Sigma\{(2^n \cdot 2^n)$, n=1, 2 for 1 one-level symmetry spin-down and spin-up $\pm \frac{1}{2}\pi N$ Hadamard and/or Pauli Z-gated qubit operators and 1 two-level symmetry spin-down and spin-up XOR-gated qubit operators in a sum of ($\pm 4$, $\pm 16$) operators with $\pm \frac{1}{2}\pi N$ phase transition degrees. [2] H=$\Sigma\{(2^n)$, n=5, 6$\}$ for 6 two-level symmetry spin-down and spin-up XOR-gated qubit operator networks in a sum of ($\pm 32$, $\pm 64$) operators with $\pm \frac{1}{2}\pi N$ phase transition degrees. [3-4] H=$\Sigma\{(2^n)$, n=1, 2$\}$ for 2 one-level symmetry spin-down and spin-up $\pm \frac{1}{2}\pi N$ Hadamard and/or Pauli Z-gated qubit operator networks and 2 two-level symmetry spin-down and spin-up XOR-gated qubit operator networks in a sum of double ($\pm 4$, $\pm 16$) operators at two discrete frequency and time domains respectively with $\pm \frac{1}{2}\pi N$ phase transition degrees. [5] H=$\Sigma\{(2^n)$, n=7 for 8 two-level symmetry spin-down and spin-up XOR-gated qubit operator networks in a sum of ($\pm 128$) operators with $\pm \frac{1}{2}\pi N$ phase transition degrees. [6-7] H=$\Sigma\{(2^{2n+1})$, n=1, 2, 3 for 4 one-level symmetry spin-down and spin-up $\pm \frac{1}{2}\pi N$ Hadamard and/or Pauli Z-gated qubit operator networks and 20 two-level symmetry spin-down and spin-up XOR-gated qubit operator networks in a sum of double ($\pm 8$, $\pm 32$, $\pm 128$) operators at two discrete frequency and time domains respectively with $\pm \frac{1}{2}\pi N$ phase transition degrees. [8] H=$\Sigma\{(2^{2n+1})$, n=1, 2, 3 for 2 one-level one level symmetry spin-down and spin-up $\pm \frac{1}{2}\pi N$ Hadamard and/or Pauli Z-gated qubit operator networks and 10 two-level symmetry spin-down and spin-up XOR-gated qubit operator networks in a sum of ($\pm 8$, $\pm 32$, $\pm 128$) operators with $\pm \frac{1}{2}\pi N$ phase transition degrees. [9] $\{(2^n)$, n=6, 7 for 12 two-level symmetry spin-down and spin-up XOR-gated qubit operator networks in a sum of ($\pm 64$, $\pm 128$) operators with $\pm \frac{1}{2}\pi N$ phase transition degrees. Owning to $\pm \frac{1}{2}\pi N$ and $\pm \frac{1}{2}\pi N$ phase transitions in [1-4] and [6-9] equations, bio-redox single electron spins can achieve room temperature single-level symmetry spin-down and spin-up and two-level symmetry spin-down and spin-up superconductor qubit operator networks and their permutations.
Figure 5B:
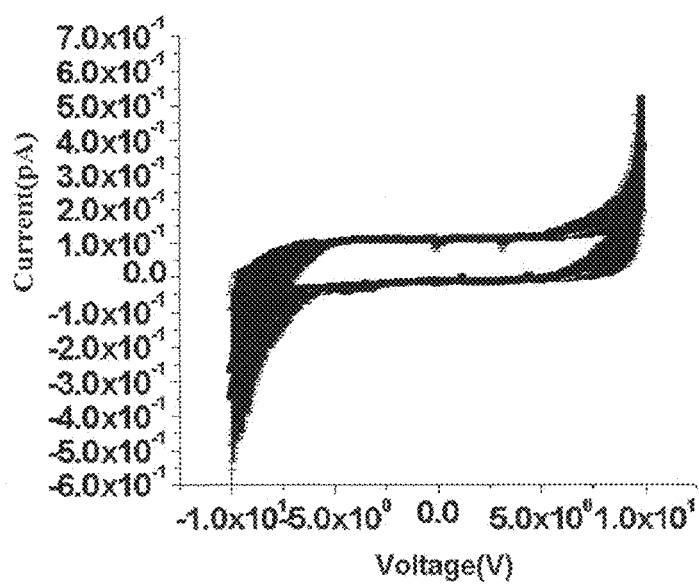
Figure 5C:
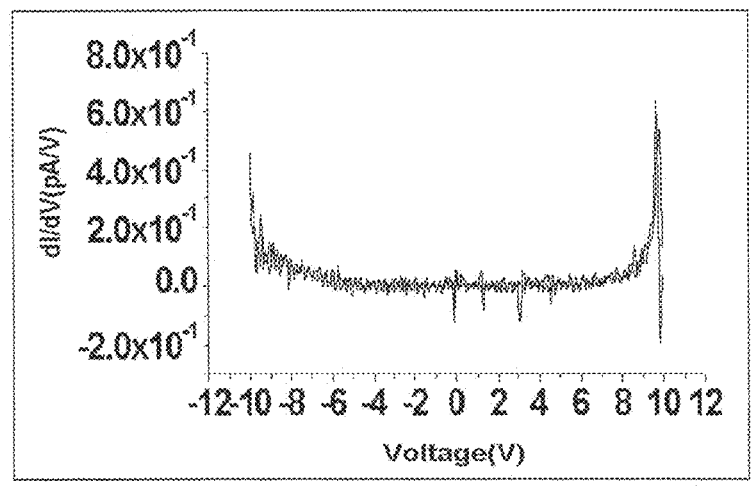
Figure 5D:
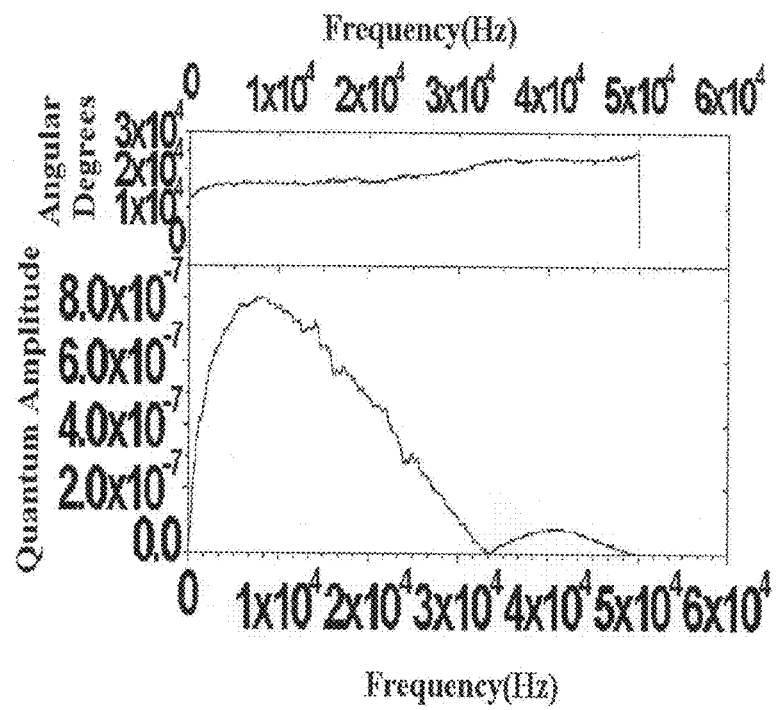
Figure 5E:
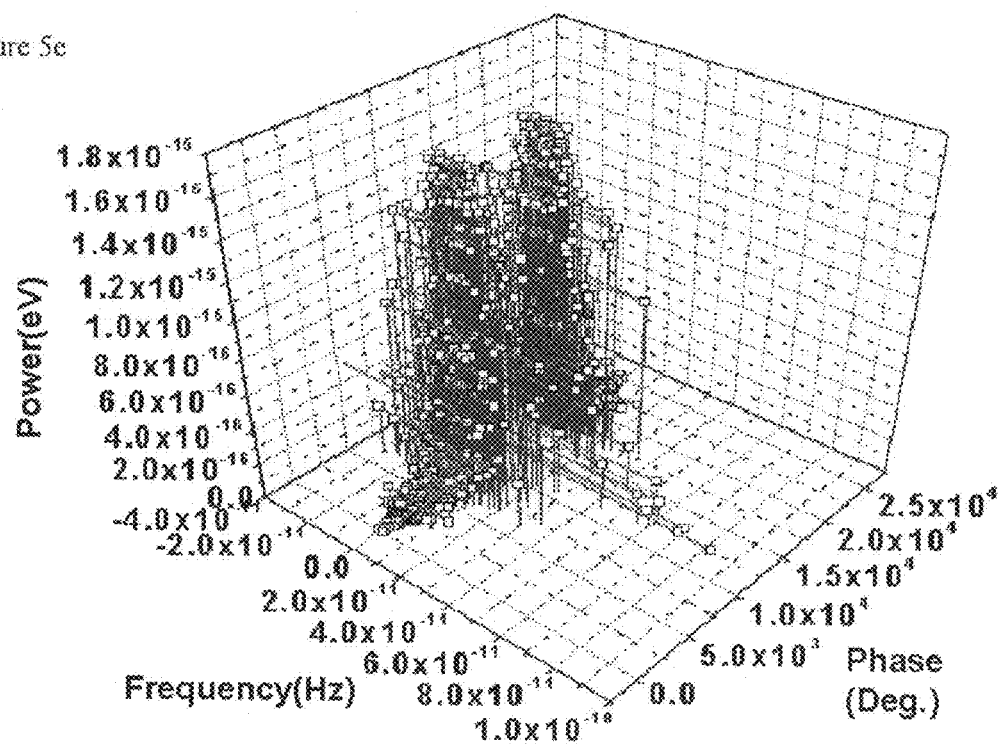
Figure 5F:
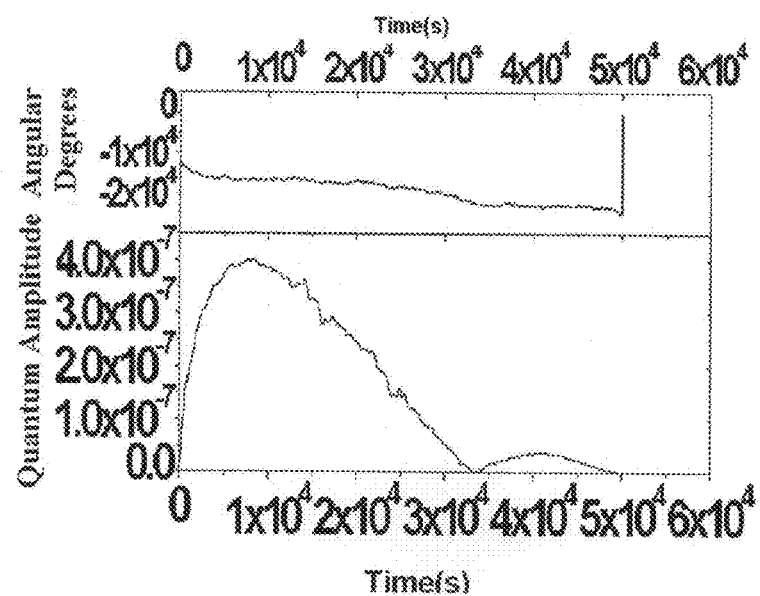
Figure 5G:
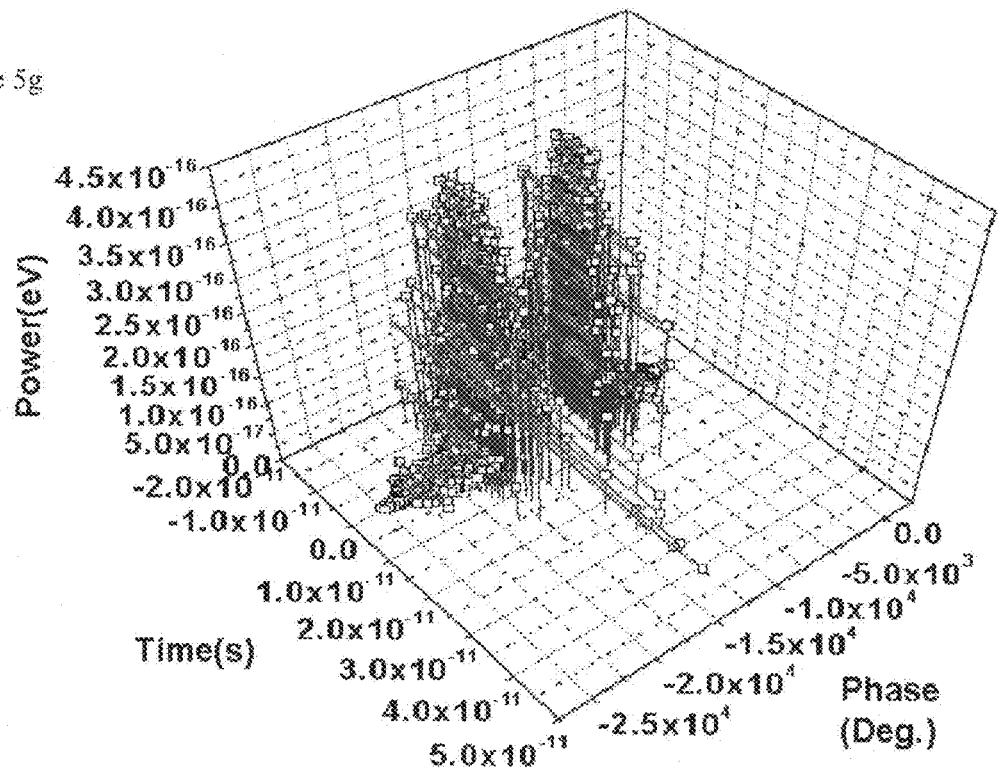
Figure 5H:
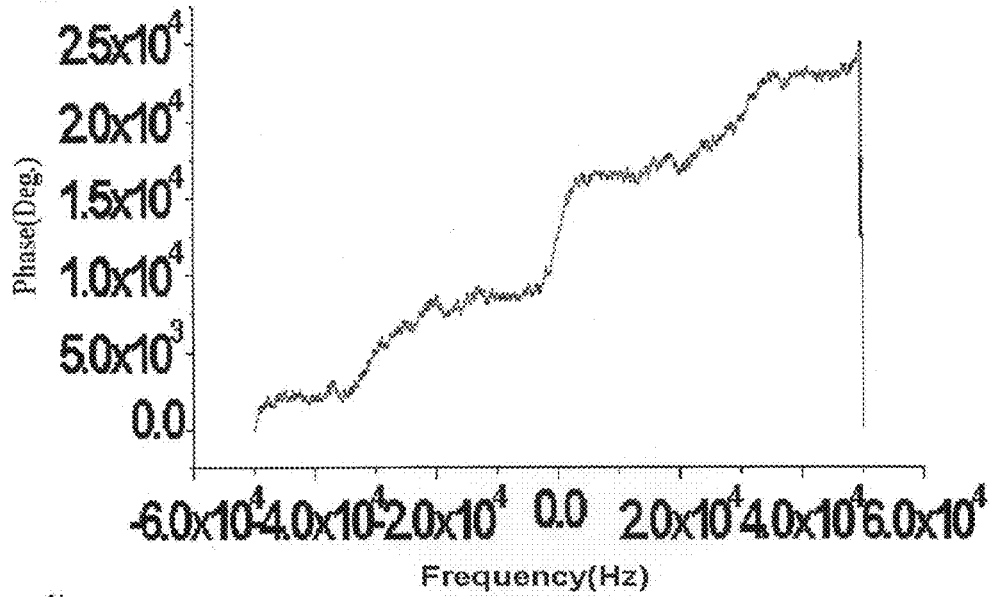
Figure 5I:
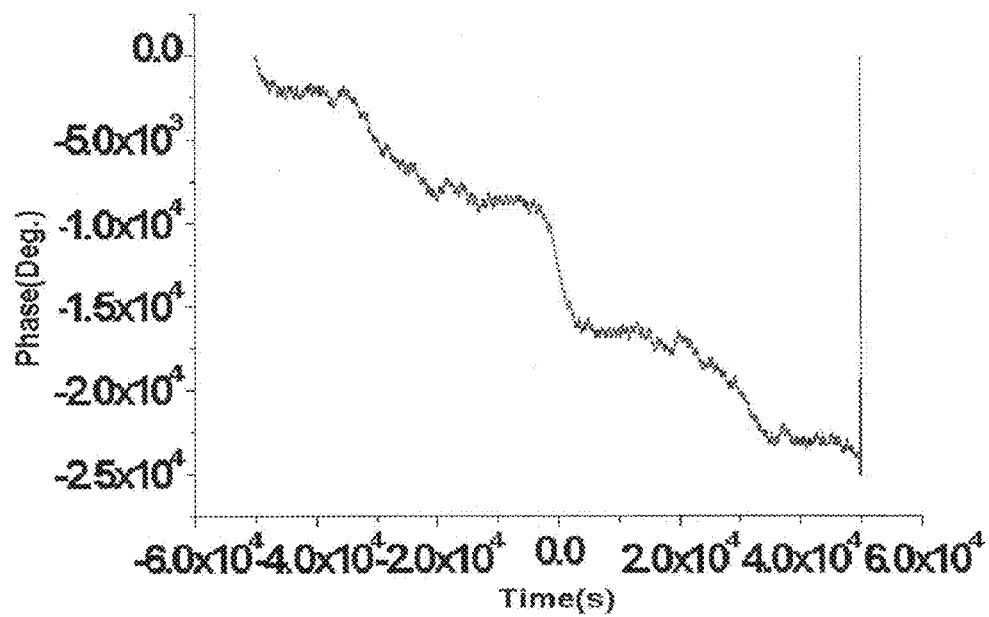

Pharmaceutical liquids are prepared according to the pharmaceutical standards, which may refer to the SFDA issued by the Ministry of Health in China. FIG. 5a-i depicts a C-AFM image and an average I-V curve with s.d., a quantum Hall effect, $\hbar$-related quantum wave amplitudes and angular momentum dynamics in frequency and time domains and symmetry spin-down and spin-up room temperature superconductor qubit network features obtained from the 1:1:1:1 of Example 5 according to the $L_{16}(2)^{15}$ orthogonal design protocol under a 10 class clean environment.

i. A verapamil hydrochloride pharmaceutical liquid is prepared at a concentration of 2.5 mg/5 mL.
ii. An isoprenaline hydrochloride pharmaceutical liquid is prepared at a concentration of 2 mg/100 mL.
iii. A physiological buffer solution of superoxide dismutase is prepared at a concentration of 1 mg/2 mL.
iv. A physiological buffer solution of adenosine triphosphate is prepared at a concentration of 20 mg/3.3 mL.
v. A verapamil hydrochloride pharmaceutical droplet may comprise the molecular number of about $10^{12}$ verapamil hydrochloride molecules to about $10^{14}$ verapamil hydrochloride molecules.
vi. An isoprenaline hydrochloride pharmaceutical droplet may comprise the molecular number of about $10^{14}$ isoprenaline hydrochloride molecules to about $10^{15}$ isoprenaline hydrochloride molecules.
vii. A superoxide dismutase buffer droplet may consist of about $10^{11}$ superoxide dismutase molecules to about $10^{13}$ superoxide dismutase molecules.
viii. An adenosine triphosphate buffer droplet may be made up of about $10^{11}$ adenosine triphosphate molecules to about $10^{19}$ adenosine triphosphate molecules.
ix. A bio-redox single electron system is made in physiological buffer solution of xanthine oxidase (XO) and xanthine (X) according to a 1:20 molecular mixture ratio, and the desired molecular xanthine number may be in a range of about $3 \times 10^{16}$ X molecules to about $3 \times 10^{19}$ X molecules.
x. A hexa-redox-pharmaceutical droplet hybrid is made by mixing v, vi, vii, viii and ix according to a desired molecular mixture ratio of 1:1:1:1 in the $L_{16}(2)^{15}$ orthogonal design protocol.
xi. A hybrid droplet of x is prepared onto a clean graphite substrate surface by controlling the spatial distance of 0 Å-200 Å at room temperature for 30-60 minutes, up to forming to a redox nano-drug quantum dot network lattice through a droplet crystal lattice hetero-epitaxy bottom-up self-assembly approach.
xii. At a room temperature and in air, C-AFM is used for imaging the topographic structure of a self-assembled redox nano-drug quantum dot network lattice, as shown in FIG. 5a, probing an average I-V curves of 5 measurements with s.d. in FIG. 5b, analyzing quantum resonance effect in dI-dV conductance spectrum (FIG. 5c), and $\hbar$-related quantum wave amplitudes and angular momentum dynamics in frequency and time domains and symmetry spin-down and spin-up room temperature superconductor qubit network features, as revealed in FIG. 5d-i.

Example 6

Figures 6A, 6B:
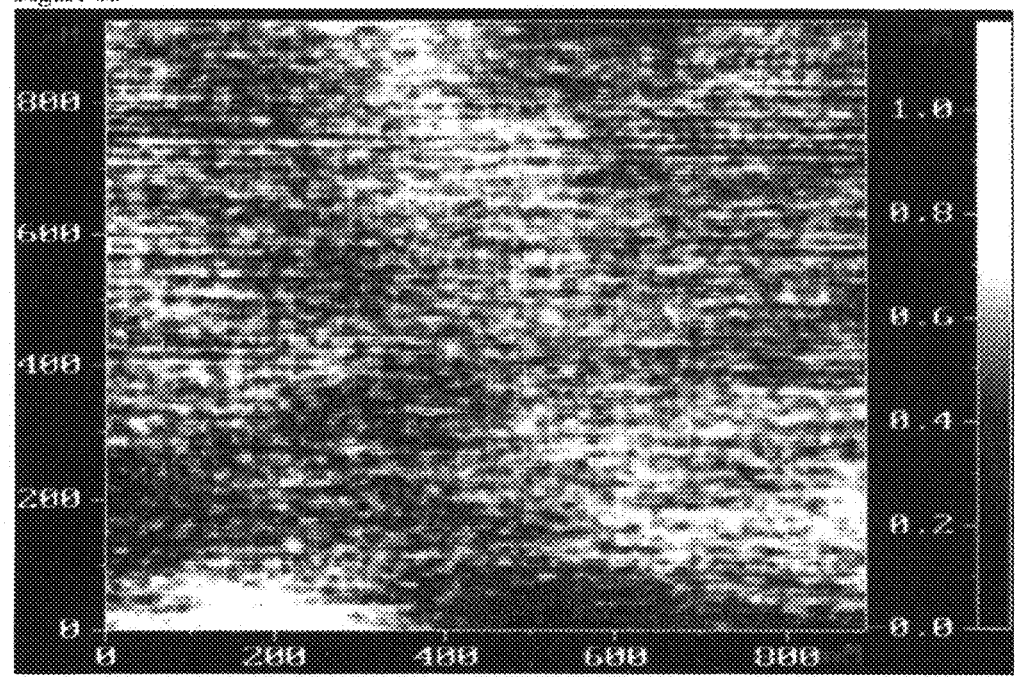
FIG. 6. a, C-AFM characterizes the quantum cellular automate (QCA) topographic structure of hexa-ingredient redox nano-medicine quantum dot room temperature superconductivity network onto the 0.01-0.05$\Omega$·cm n-doped silicon chip substrate according to the molar ratio of 2:3:1:2 in the $L_9(3)^4$ orthogonal design model plus the molar ratio of 1:20 bio-redox single electron system (XO:X) made at $-18°$ C.--$20°$ C. for 8-12 hours, wherein hexa-ingredient redox nano-medicine quantum dots and quantum wires are regularly stacked in a cubic box of about 200 Å QCA arrays with cross-bar molecular junctions and upper planes and lower planes as well as molecular numbers in a range of about $10^{19}$ to about $10^{22}$, its size of QCA arrays (a typically smaller selected region of QCA arrays are shown in a red line box) is a length of 800 nm, a width of 800 nm and an a height of an atomic layer (~0.33 nm) stacking after deducing the height of a substrate about 0.67 nm (white vs. black). b, C-AFM probes the I-V curves of FIG. 6a (data are expressed as an average curve of 6 measurements with s.d.), wherein spin-down and spin-up quantum tunneling currents may achieve the maximum of 10 pA and the minimum of $-25$ pA within $\pm 5$V bias potentials and there are two electron hysteresis loops within 1.5V-2V bias potentials and 0V-1.5V bias potentials. c, The average dI-dV differential conductance spectra of FIG. 6b, wherein room temperature spin-up and spin-down superconductor quantum resonance tunneling peaks and kondo peaks around 0V bias voltage are clearly revealed for room temperature superconductor qubit memory. d, $\hbar$-related amplitude and angular momentum of quantum wave of FIG. 6c in frequency domains, wherein the amplitudes of double-peaked quantum wave respectively locate 7.5E-7 and 9.5E-4 within 0 Hz-5E+4 Hz. e, $\hbar$-related amplitude and angular momentum of quantum wave of FIG. 6c in time domains, wherein the amplitudes of double-peaked quantum wave respectively locate 3.5E-5 and 4.75E-5 within 0 s-5E+4 s, revealing a feature of non-volatile qubits. f, Single electron tunneling-driven 11 two-level and 3 one-level room temperature spin-down superconductor qubit operator network around 0 Hz with a unitary qubit operator |1> and double spin echo, wherein the $\hbar$-related non-symmetry spin-down qubit operators satisfy the binary code matrix of Hamiltonian H=$\{\Sigma (2^n)$, n=1, 2, 3, 4, 5, 7$\}$ in frequency domains. g, Single electron tunneling-driven 11 two-level and 2 one-level room temperature non-symmetry spin-up superconductor qubit operator network around 0 s with a unitary qubit operator |1> and double spin echo, wherein the $\hbar$-related spin-up qubit operators satisfy the binary code matrix of Hamiltonian H=$\{\Sigma (2^n)$, n=1, 3, 4, 5, 7$\}$ in time domains. h, The average laser micro-PL spectrum of 6 measurements with s.d. for the FIG. 6a, wherein doubled PL peaks are respectively revealed around 550 nm and 575 nm wavelength with fluorescence intensity from about 4500 a.u. to about 1750 a.u. after smooth processing, suggesting photoelectron couplings to form polaritons (quantum states obtained from laser-evoked a hybrid photon-exciton pairs) within about 2500 QCA architectures. i, $\hbar$-related amplitude and angular momentum of quantum wave of FIG. 6h in frequency domains, wherein the amplitude of polaritons is around 1.8E-7 within 0 Hz-1.6E-7 Hz. j, $\hbar$-related amplitude and angular momentum of quantum wave of FIG. 6h in time domains, wherein the amplitude of polaritons is around 9.0E-8 within 0 s-1.6E-7 s. k, Polaritons-driven 180 two-level and 87 one-level symmetry spin-down qubit operator networks with 120 unitary |0> and/or |1> qubit operators in frequency domains, suggesting 3348 spin-down qubit operators to lay out 36 two-level qubit-based Majority QCA and 17 one-level spin-down qubit operators-based Majority QCA with a |1> carry. l, Polaritons-driven 180 two-level and 87 one-level symmetry spin-up qubit operator networks with 120 unitary |0> and/or |1> qubit operators, indicating 3348 spin-up qubit operator to lay out 36 two-level spin-up qubit operators-based Majority QCA and 17 one-level qubit-based Majority QCA with a |1> carry. m, The average laser micro-PL spectrum of 2 measurements with s.d. for the FIG. 6a after adding an external spinning magnetic field of RTD10T, wherein doubled PL peaks are respectively revealed around 550 nm and 575 nm wavelength with fluorescence intensity from about 3000 a.u. and 1750 a.u. after smooth processing, suggesting RTD10T-tuned photoelectron couplings to form polaritons (quantum states obtained from laser-evoked a hybrid photon-exciton pairs) within about 2500 QCA architectures, and a reduced fluorescent intensity about 1000 a.u. n, $\hbar$-related amplitude and angular momentum of quantum wave of FIG. 6m in frequency domains, wherein the RTD10T tuned amplitude of polaritons is around 1.0E-7 within 0 Hz-1.6E-7 Hz. o, RTD10T tuned polaritons-driven non-symmetry 180 two-level spin-up and 37 one-level spin-up qubit operator networks with 66 unitary spin-up |0> and/or |1> qubit operators, and 1 two-level spin-down and 8 one-level spin-down qubit operator network with 23 unitary spin-down |0> and/or |1> qubit operators, as well as double spin echo in frequency domains, suggesting 2888 two-level spin-up qubit operators to lay out 240 controlled NOT (CNOT) QCAs and 148 one-level spin-up qubit operators to lay out 24 CNOT QCAs, and 16 two-level spin-down qubit operators to lay out 1 CNOT QCA with 4 carries for 4 carries and 32 one-level spin-down qubit operators to lay out 2 CNOT QCAs with 8 carries for permutations of one-level and two-level qubit operators, as well as 66 spin-up unitary qubit operators and 23 spin-down unitary qubit operators and double spin echo for one-level and two-level qubit operator networks and qubit operator permutations in frequency domains. p, $\hbar$-related amplitude and angular momentum of quantum wave of FIG. 6m in time domains, wherein the RTD10T tuned amplitude of polaritons is around 5.0E-8 within 0 s-1.6E-7 s. q, RTD10T tuned polaritons-driven non-symmetry 3 one-level spin-up qubit operator networks and 1 two-level spin-up qubit operators with 14 unitary spin-up qubit operators, and 202 two-level spin-down qubit operator networks and 41 one-level spin-down qubit operator networks with 91 unitary spin-down qubit operators, suggesting 12 one-level spin-up qubit operator networks to be built as 1 CNOT QCA and 16 two-level spin-up qubit operators to be constructed as 1 CNOT QCA with 4 carries for permutations of one-level and two-level qubit operator networks, and 3232 two-level spin-down qubit operator networks to generate 269 CNOT QCAs with 4 carries for permutations of one-level and two-level qubit operators and 164 one-level spin-down qubit operator networks to form 13 CNOT QCAs with 8 carries for permutations of one-level and two-level qubit operators. r, The average laser micro-PL spectrum of 9 measurements with s.d. for the FIG. 6a after adding an external spinning magnetic field of RTD50T, wherein doubled PL peaks are respectively revealed around 550 nm and 575 nm wavelength with fluorescence intensity from about 4750 a.u. and 3250 a.u. after smooth processing, suggesting RTD50T-tuned photoelectron couplings to form polaritons (quantum states obtained from laser-evoked a hybrid photon-exciton pairs) within about 2500 QCA architectures, and a rise of fluorescent intensity from about 250 a.u. at 550 nm to about 1500 a.u. at 575 nm. s, $\hbar$-related amplitude and angular momentum of quantum wave of FIG. 6m in frequency domains, wherein the RTD50T tuned amplitude of polaritons is around 4.0E-7 within 0 Hz-1.6E-7 Hz. t, RTD50T tuned polaritons-driven symmetry 615 two-level and 237 one-level spin-down qubit operator networks with 44 unitary spin-down |0> and/or |1> qubit operators, suggesting 9840 two-level spin-down qubit operators to lay out 820 (CNOT) QCAs and 237 one-level spin-down qubit operators to lay out 79 CNOT QCAs in frequency domains. u, $\hbar$-related amplitude and angular momentum of quantum wave of FIG. 6m in time domains, wherein the RTD50T tuned amplitude of polaritons is around 2.0E-7 within 0 s-1.6E-7 s. v, RTD50T tuned polaritons-driven symmetry 615 two-level and 237 one-level spin-up qubit operator networks with 44 unitary spin—|0> and/or |1> qubit operators, suggesting 9840 two-level spin-up qubit operators to lay out 820 (CNOT) QCAs and 237 one-level spin-up qubit operators to lay out 79 CNOT QCAs in time domains. w, The average laser micro-PL spectrum of 3 measurements with s.d. for the FIG. 6a after adding an external spinning magnetic field of RTD110T, wherein the PL peak is visible around 500 nm wavelength with fluorescence intensity from about 600 a.u. through smooth processing. x, $\hbar$-related amplitude and angular momentum of quantum wave of FIG. 6w in frequency domains, wherein the RTD110T tuned amplitude of polaritons is around 2.75E-8 within 0 Hz-2.0E-7 Hz. y, Polaritons-driven 2 one-level non-symmetry spin-up qubit operator networks with double spin echo and unitary qubit operator |0>, suggesting 8 spin-up qubit operators to form 1 QCA with 3 carries for permutations of |0> and/or |1>. z, $\hbar$-related amplitude and angular momentum of quantum wave of FIG. 6w in time domains, wherein the RTD110T tuned amplitude of polaritons is around 1.375E-8 within 0 s-2.0E-7 s. I, Polaritons-driven 2 one-level non-symmetry spin-down qubit operator networks with double spin echo and unitary qubit operator |1>, suggesting 8 spin-up qubit operators to form 1 QCA with 3 carries for permutations of |0> and/or |1>. 120 unitary |0> and/or |1> qubit operators in time domains. II, The average laser micro-PL spectrum of 14 measurements with s.d. for the FIG. 6a after adding an external spinning magnetic field of 70D, wherein the double-peaked PL spectrum is visible around 250 nm, 1250 nm and 1750 nm wavelengths with fluorescence intensity from about 1400 a.u., 3000 a.u. and 1000 a.u. through smooth processing. III, $\hbar$-related amplitude and angular momentum of quantum wave of FIG. 6lI in frequency domains, wherein the 70D tuned amplitude of polaritons is around 1.5E-7 within 0 Hz-1.5E-7 Hz. IV, Polaritons-driven 413 two-level spin-down qubit operator networks and 106 one-level qubit operator networks with 183 unitary spin-down |0> and/or |1> qubit operators, suggesting 6608 two-level spin-down qubit operators to form 1521 majority QCAs with 3 carries for permutations, and 424 one-level spin-down qubit operators to form 84 majority QCAs with 4 carries for permutations, and as well as double spin echo for non-symmetry one-level and two-level spin-down qubit operator networks. V, $\hbar$-related amplitude and angular momentum of quantum wave of FIG. 6lI in time domains, wherein the 70D tuned amplitude of polaritons is around 7.5E-8 within 0 Hz-1.5E-7 Hz. VI, Polaritons-driven 387 two-level spin-up qubit operator networks and 125 one-level qubit operator networks with 163 unitary spin-up |0> and/or |1> qubit operators, suggesting 7392 two-level spin-up qubit operators to form 1478 majority QCAs with 2 carries for permutations, and 500 one-level spin-up qubit operators to form 100 majority QCAs, and as well as double spin echo for non-symmetry one-level and two-level spin-down qubit operator networks. VII, The average laser micro-PL spectrum of 6 measurements with s.d. for the FIG. 6a after adding an external spinning magnetic field of 104D, wherein the double-peaked PL spectrum is visible around 475 nm, 550 nm and 575 nm wavelengths with fluorescence intensity from about 2750 a.u., 3000 a.u. and 1250 a.u. through smooth processing. VIII, $\hbar$-related amplitude and angular momentum of quantum wave of FIG. 6VII in frequency domains, wherein the 104D tuned amplitude of polaritons is around 1.25E-7 within 0 Hz-1.65E-7 Hz. IX, Polaritons-driven 151 two-level spin-down qubit operator networks and 74 one-level spin-down qubit operator networks with 98 unitary spin-down |0> and/or |1> qubit operators, suggesting 2416 two-level spin-down qubit operators to form 485 majority QCAs with 1 carry for operator permutation, and 296 one-level spin-down qubit operators to form 58 majority QCAs with 6 carries for operator permutations, and as well as double spin echo for non-symmetry one-level and two-level spin-down qubit operator networks. X, $\hbar$-related amplitude and angular momentum of quantum wave of FIG. 6VII in time domains, wherein the 104D tuned amplitude of polaritons is around 6.0E-8 within 0 s-1.65E-7 s. XI, Polaritons-driven 635 two-level spin-up qubit operator networks and 78 one-level spin-up qubit operator networks with 81 unitary spin-up |0> and/or |1> qubit operators, suggesting 10160 two-level spin-up qubit operators to form 2032 majority QCAs, and 312 one-level spin-up qubit operators to form 62 majority QCAs with 2 carries for operator permutations, and as well as double spin echo for non-symmetry one-level and two-level spin-up qubit operator networks and permutations. The spin-down and spin-up qubit operator networks in FIGS. 6k, 6l, 6o, 6q, 6t, 6v, 6y, 6I, 6IV, 6VI, 6IX and 6XI satisfy the $\Sigma(2^n)$ binary code matrix.
Figure 6C:
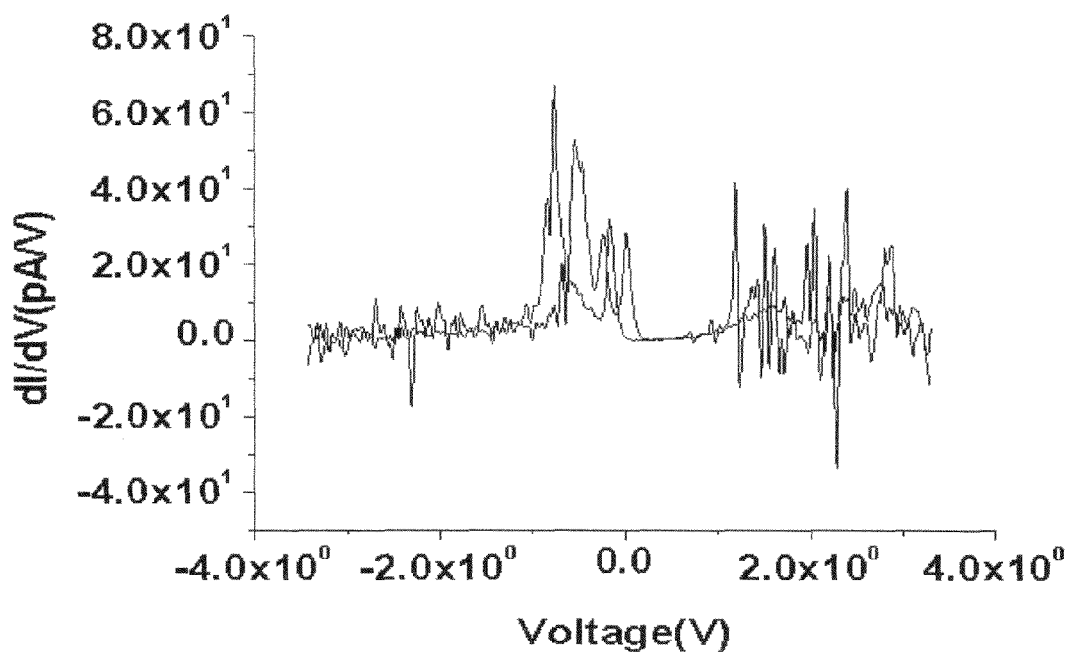
Figure 6D:
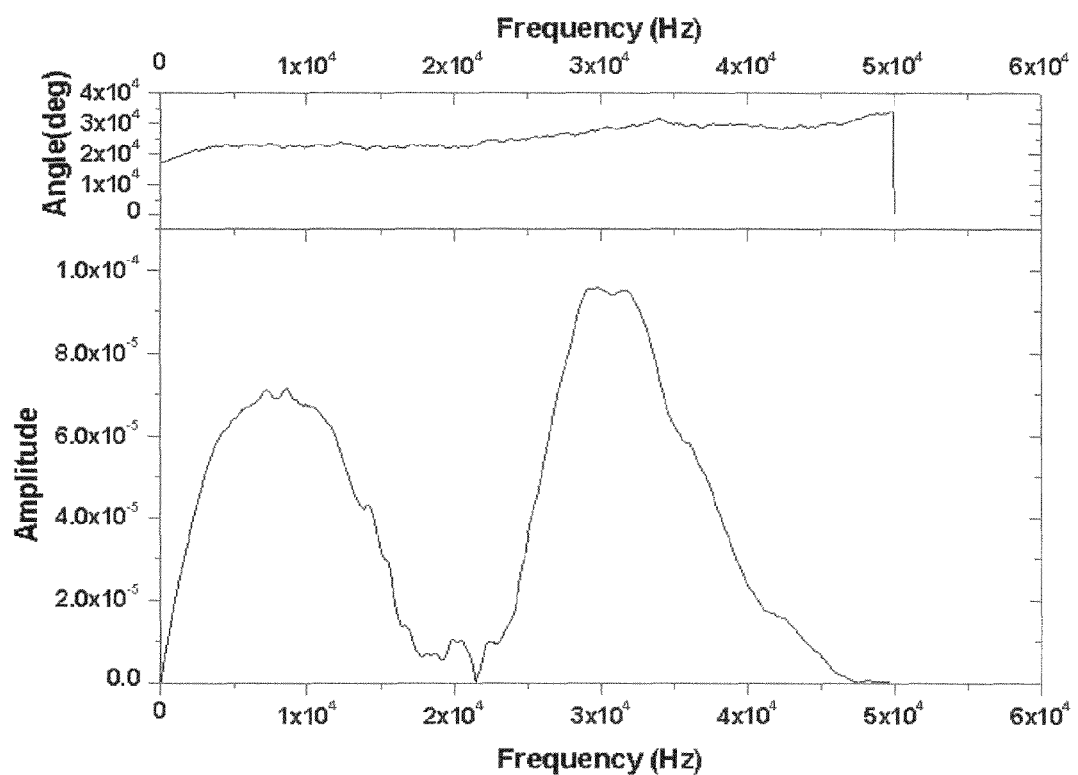
Figure 6E:
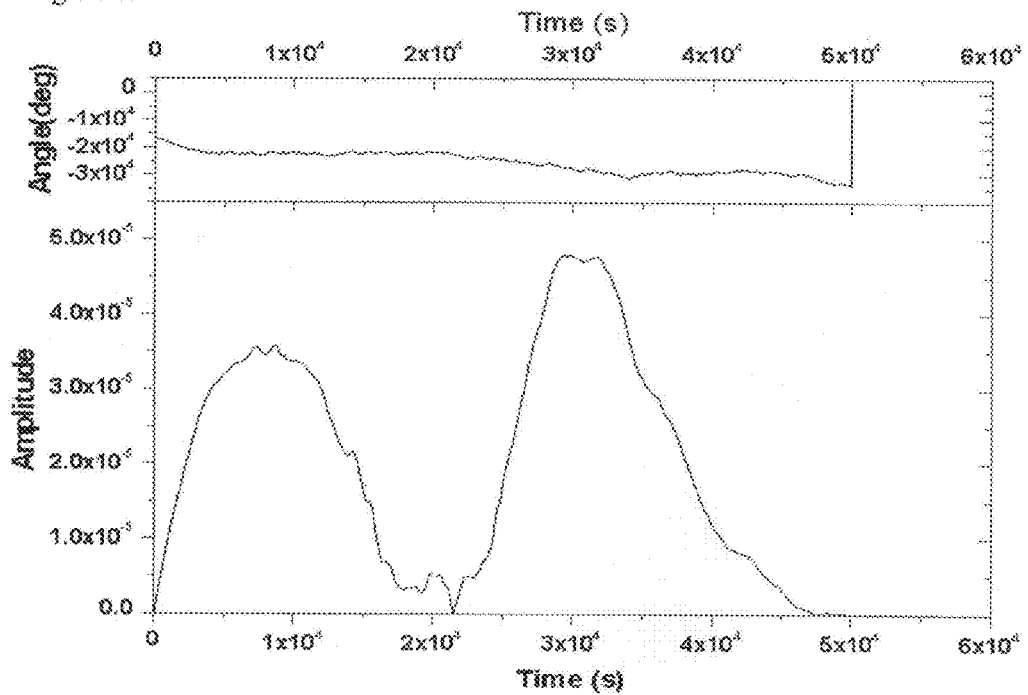
Figure 6F:
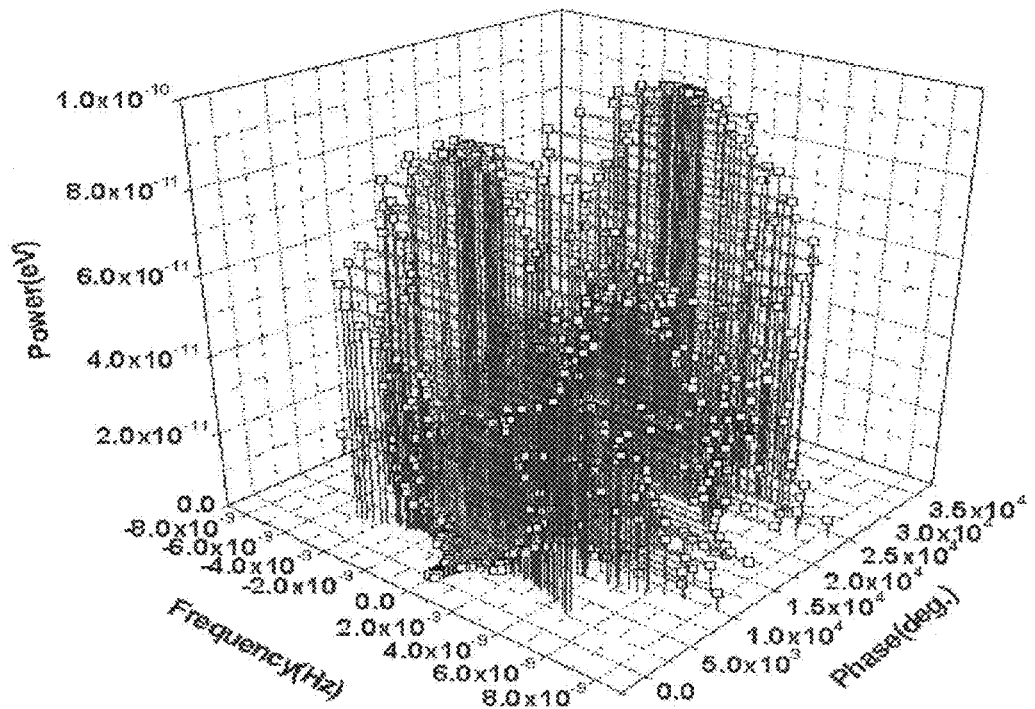
Figure 6G:
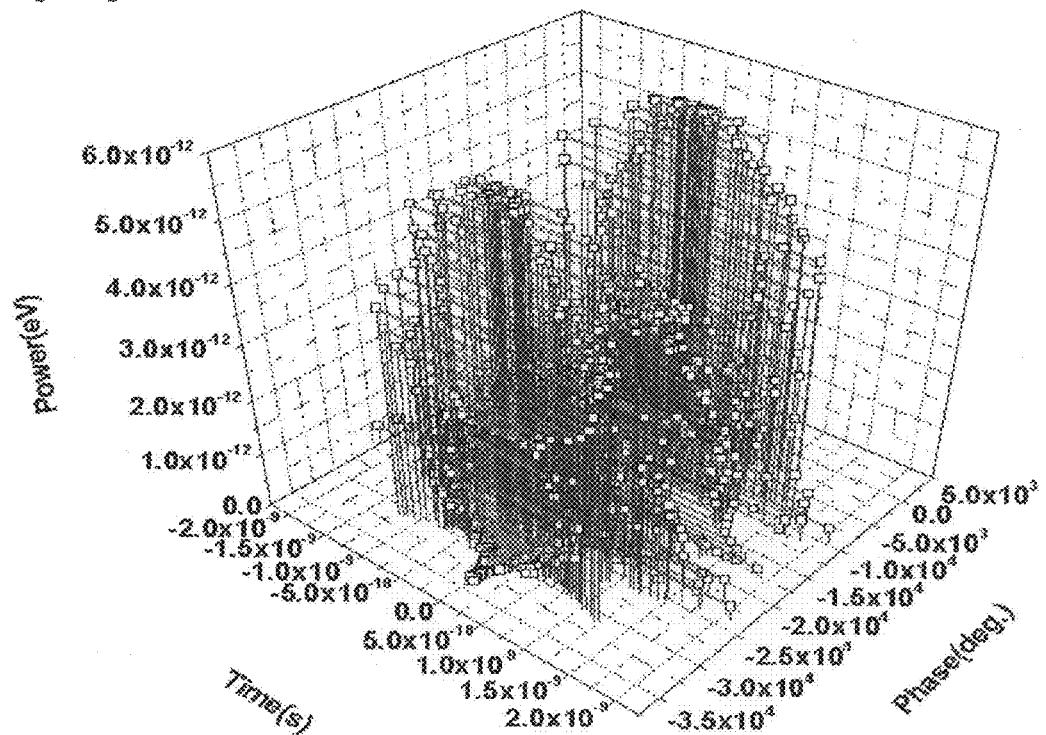
Figure 6H:
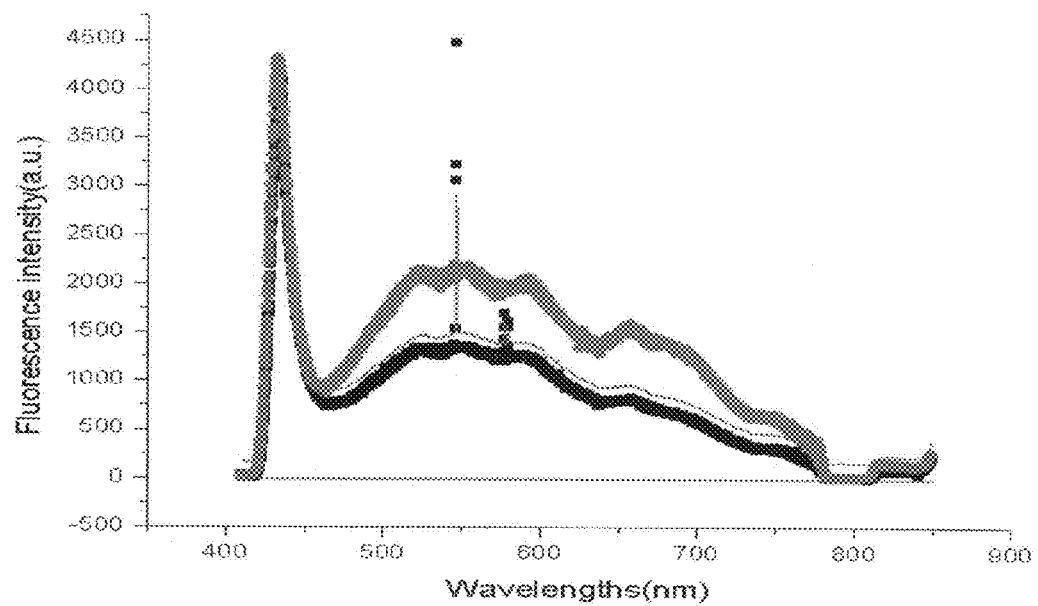
Figure 6I:
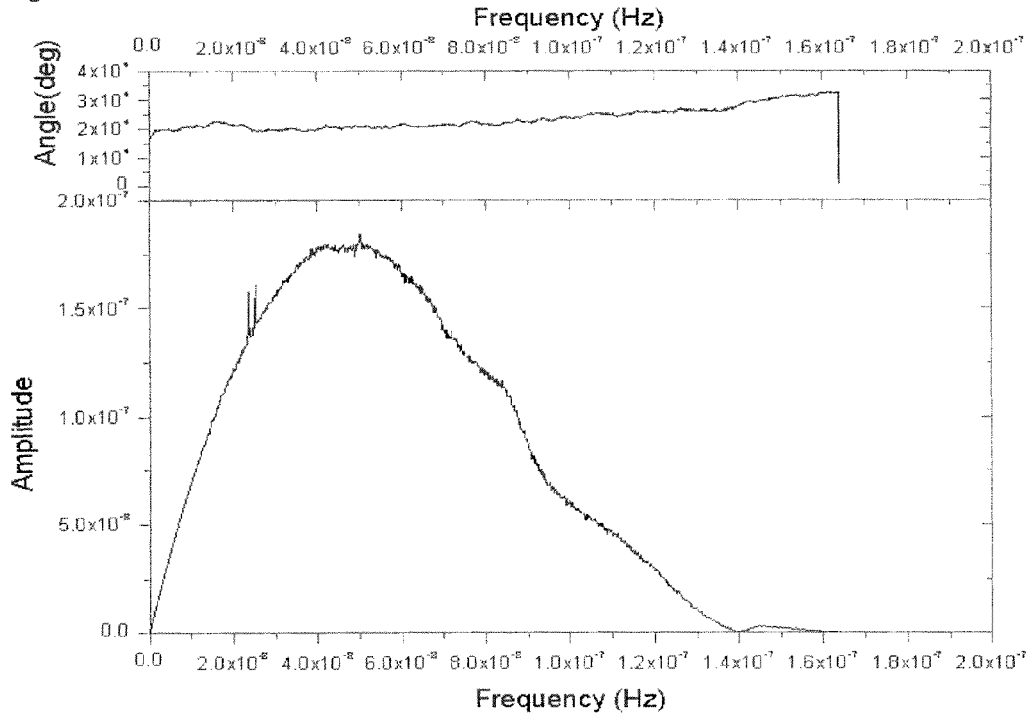
Figure 6J:
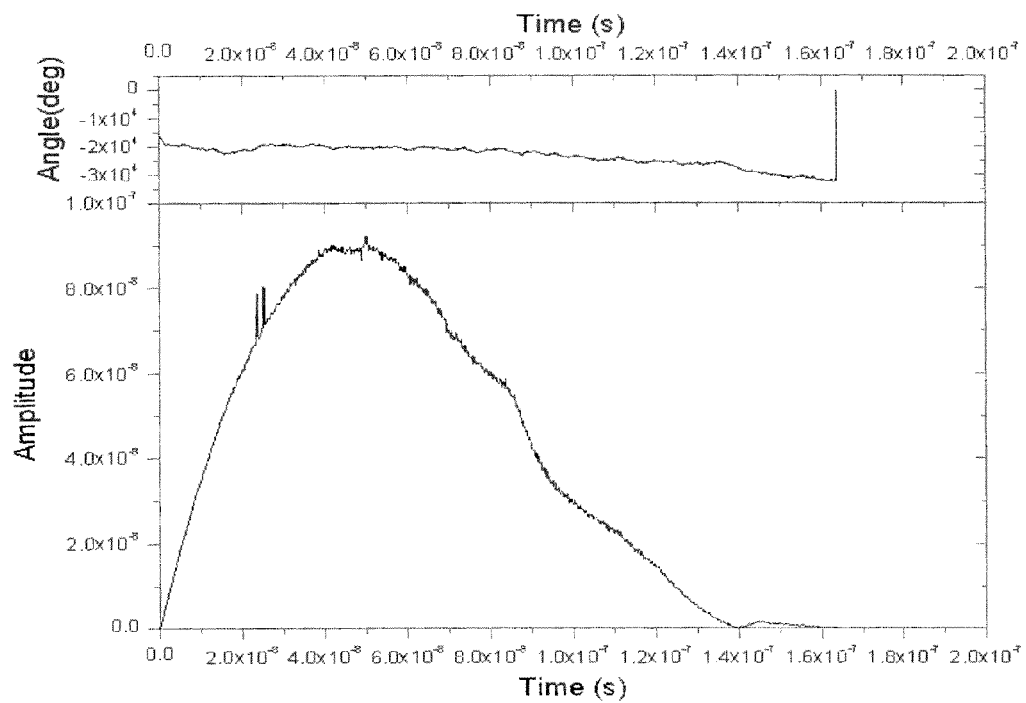
Figure 6K:
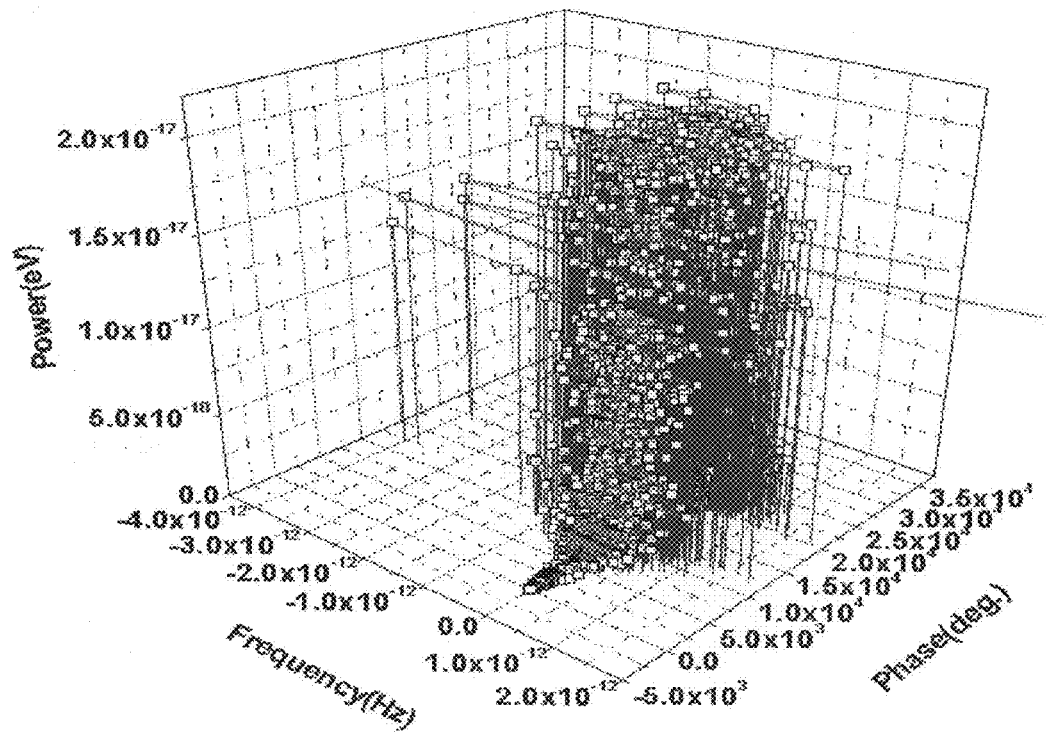
Figure 6L:
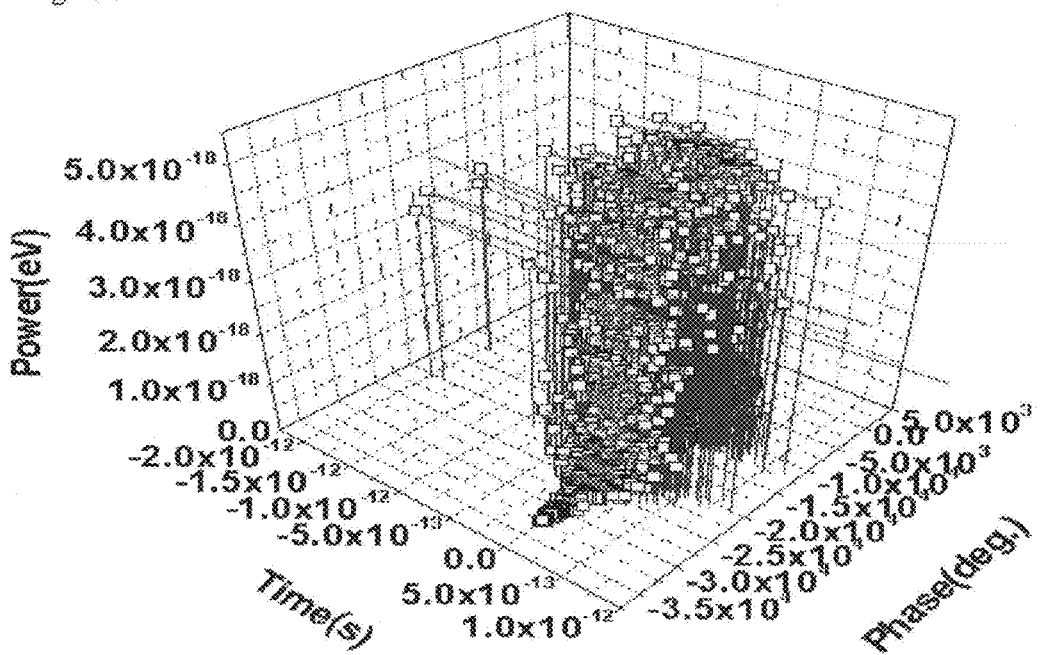
Figure 6M:
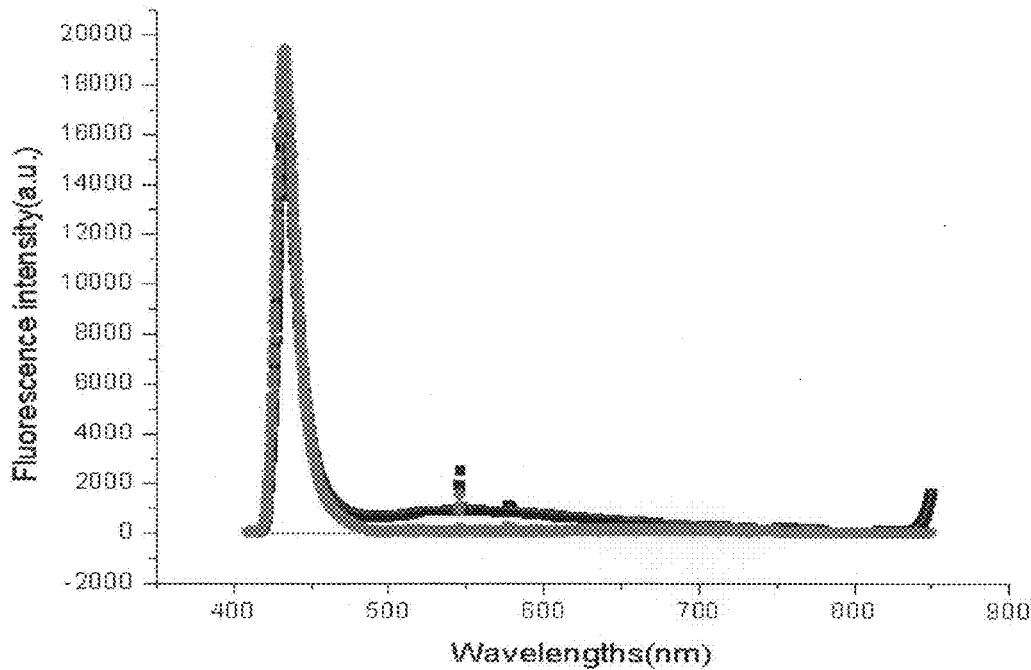
Figure 6N:
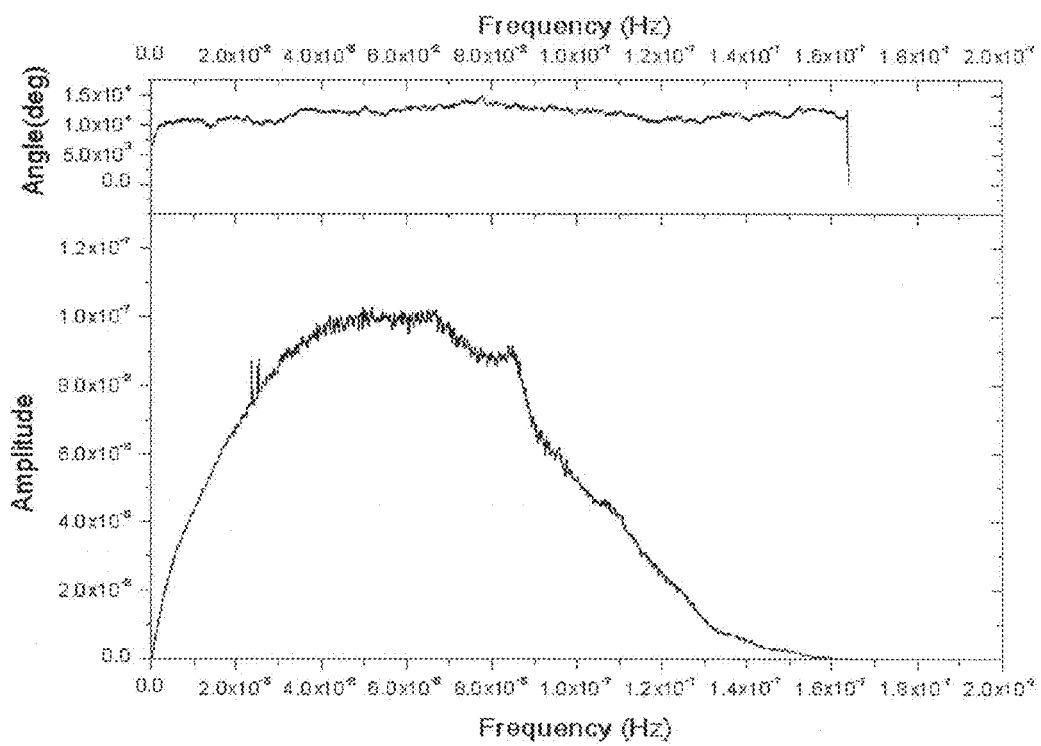
Figure 6O:
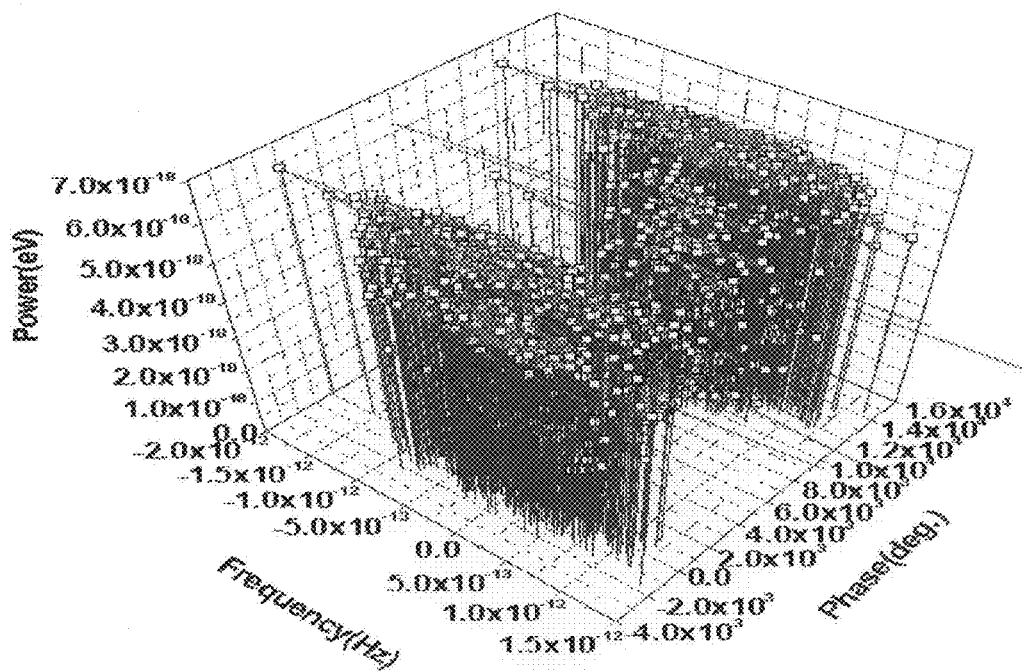
Figure 6P:
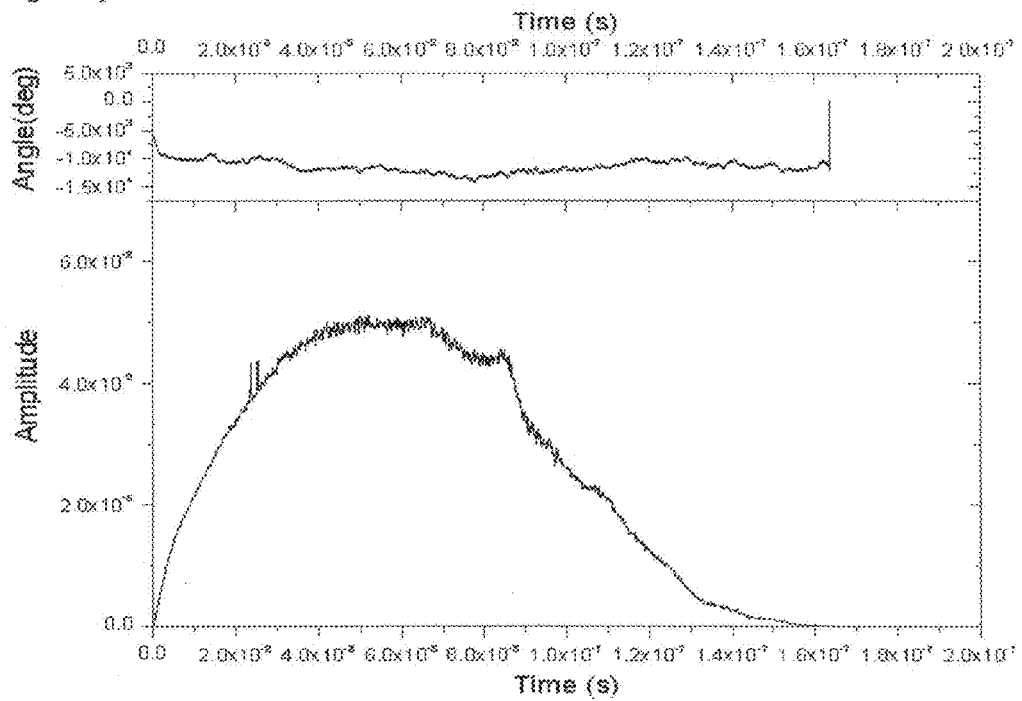
Figure 6Q:
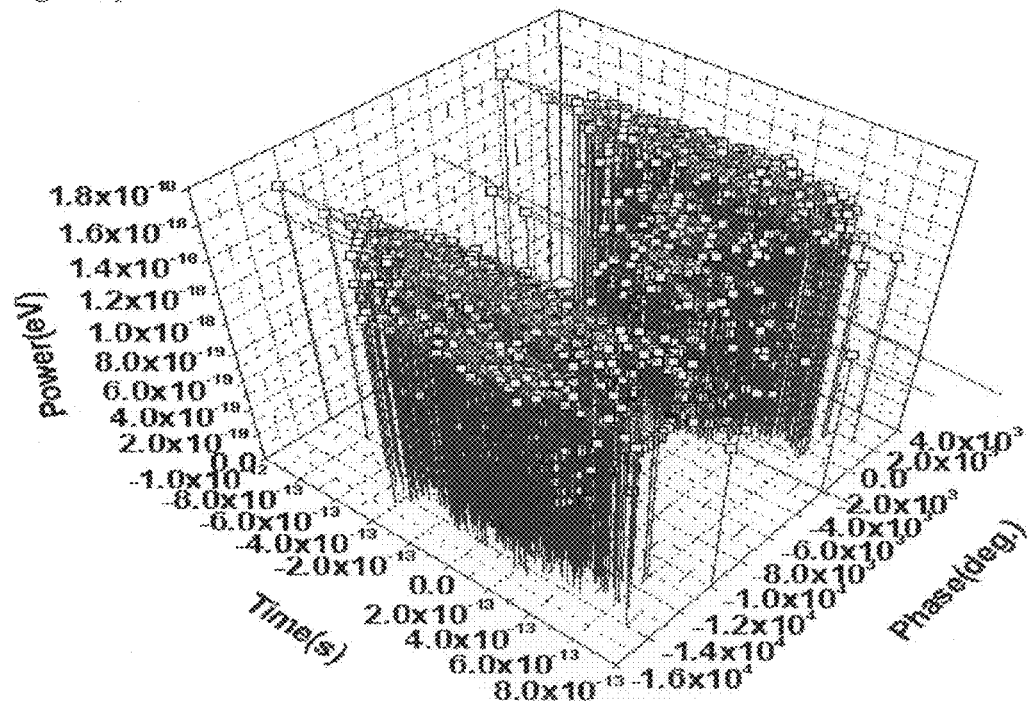
Figure 6R:
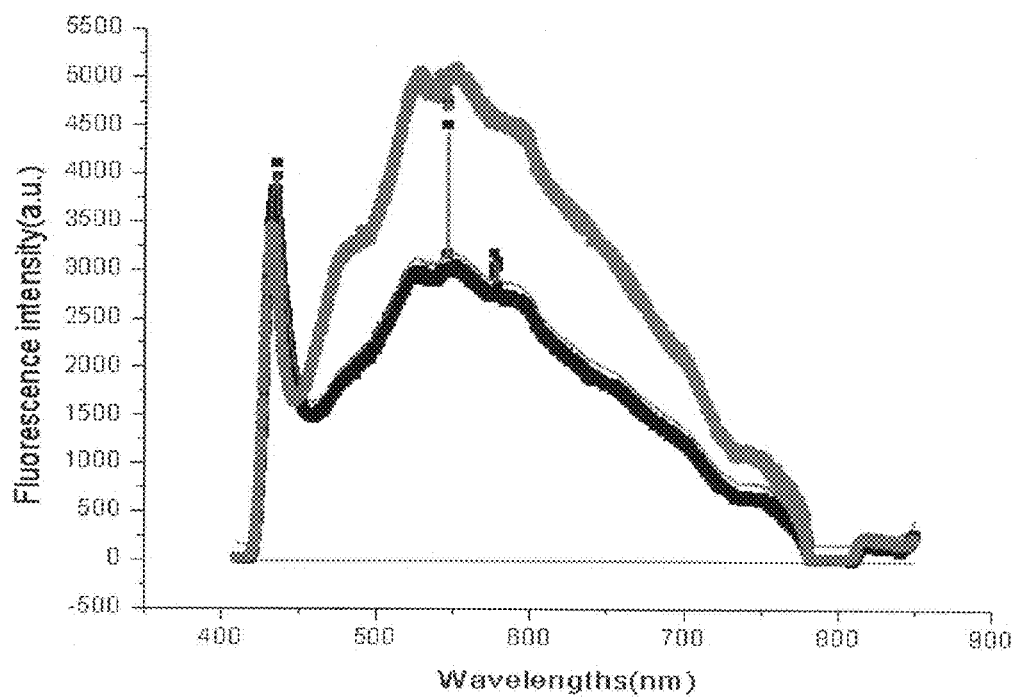
Figure 6S:
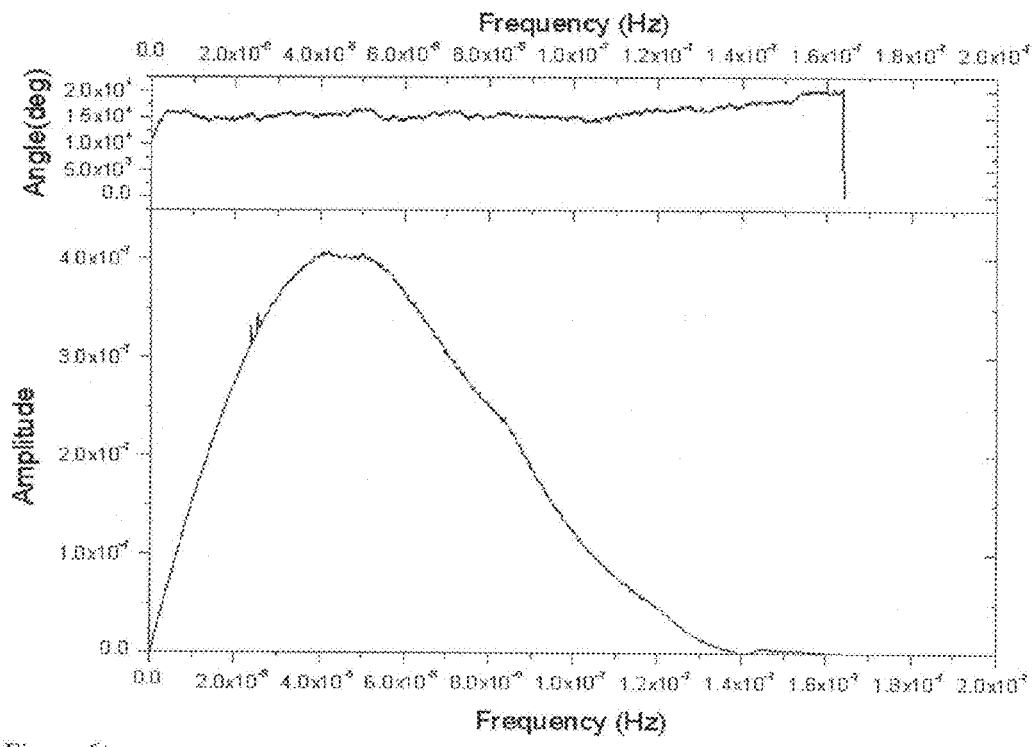
Figure 6T:
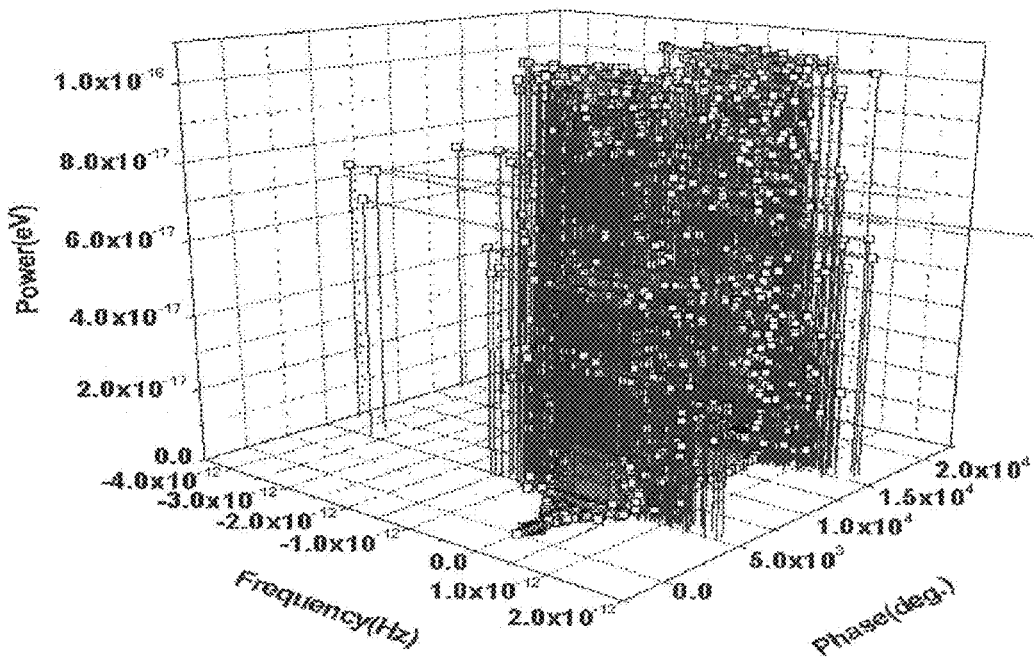
Figure 6U:
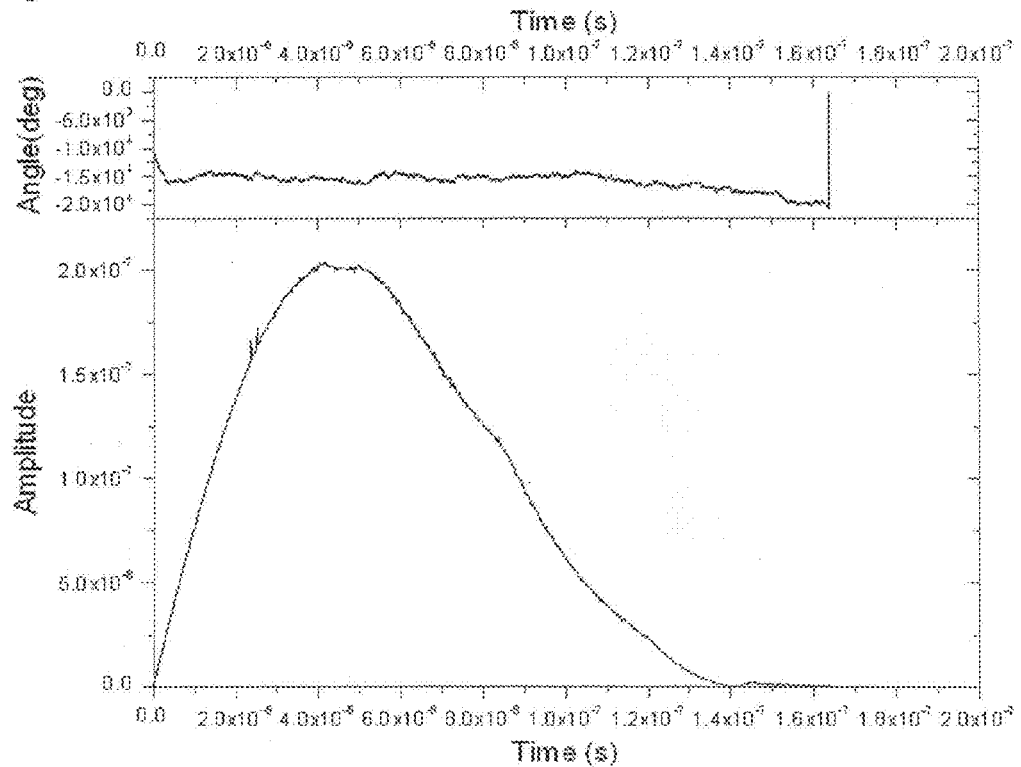
Figure 6V:
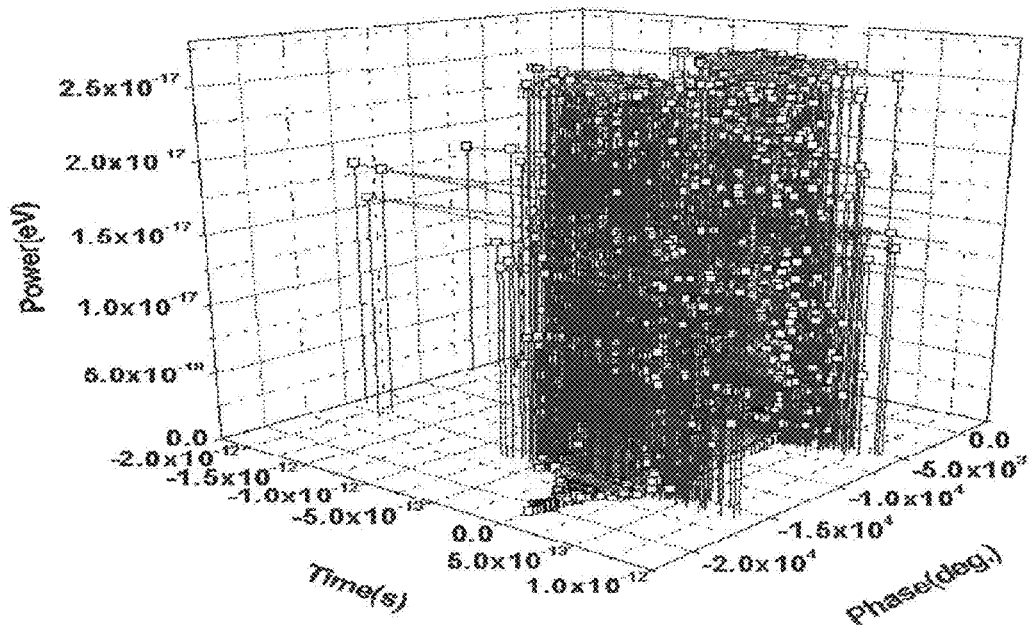
Figure 6W:
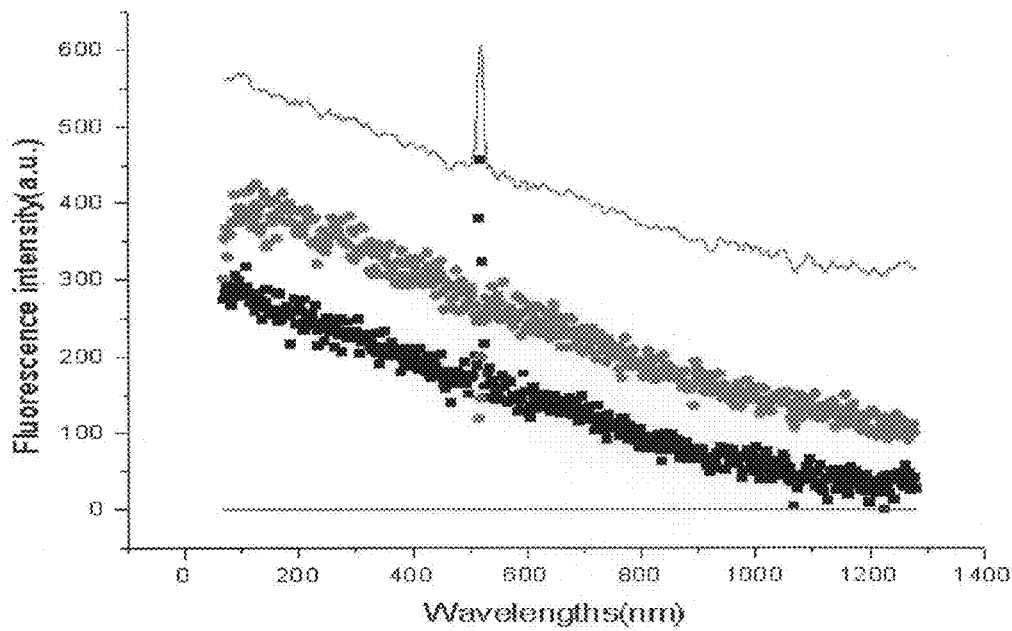
Figure 6X:
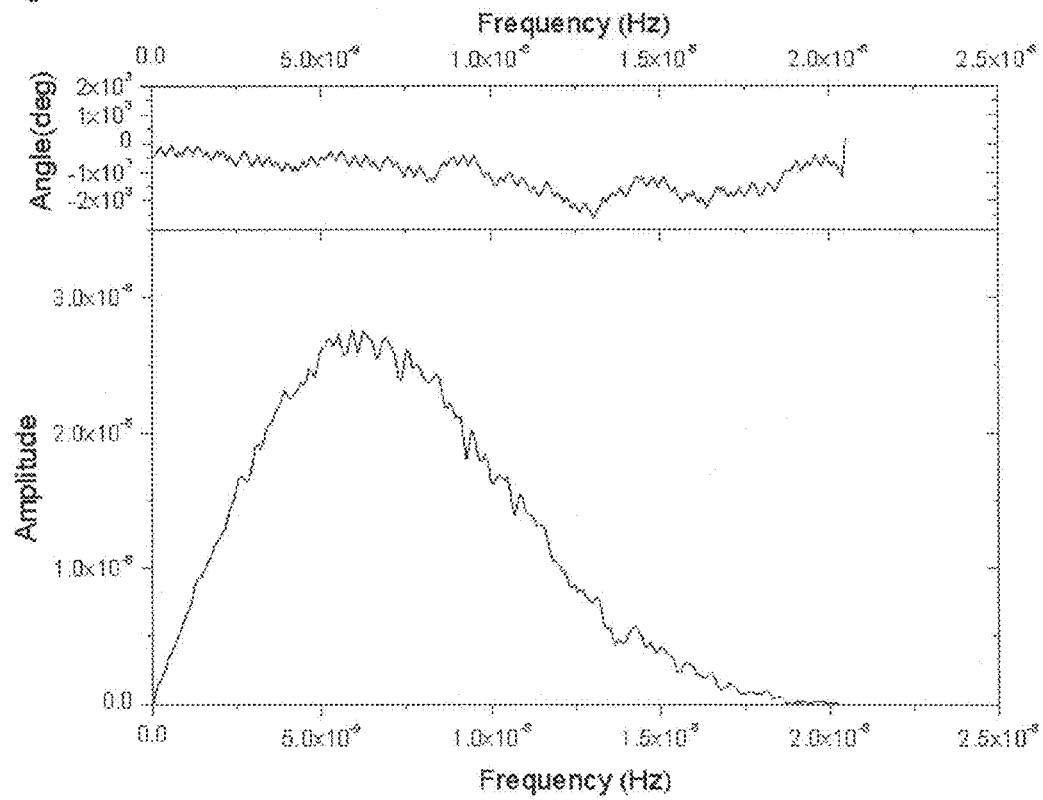
Figure 6Y:
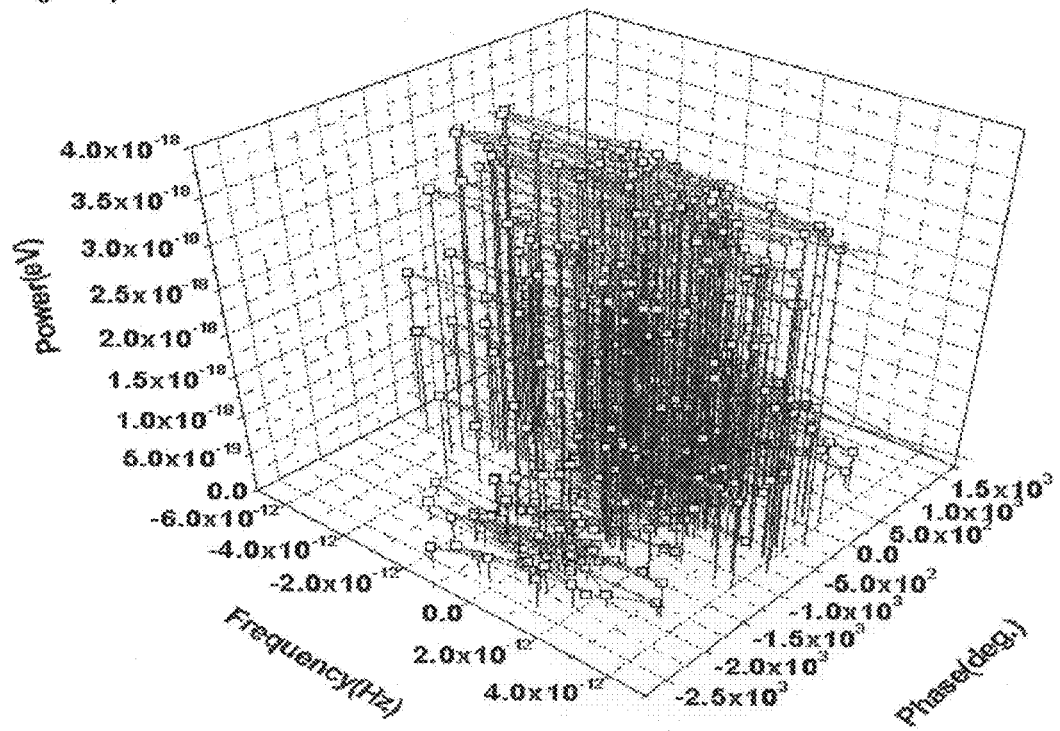
Figure 6Z:
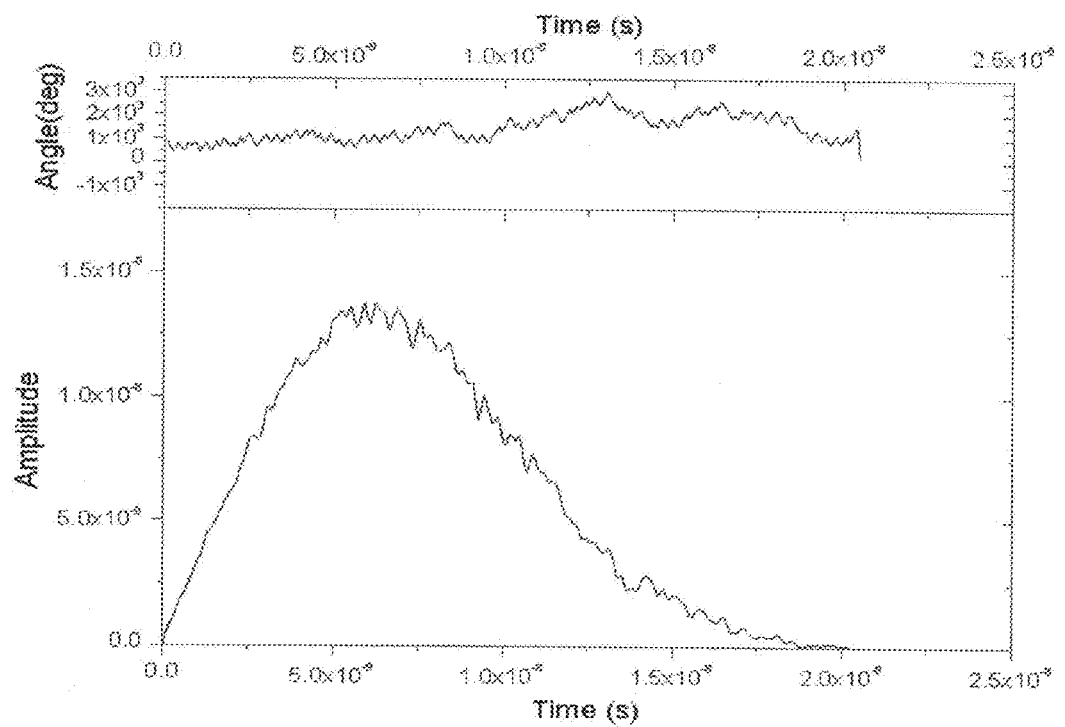
Figure 6I:
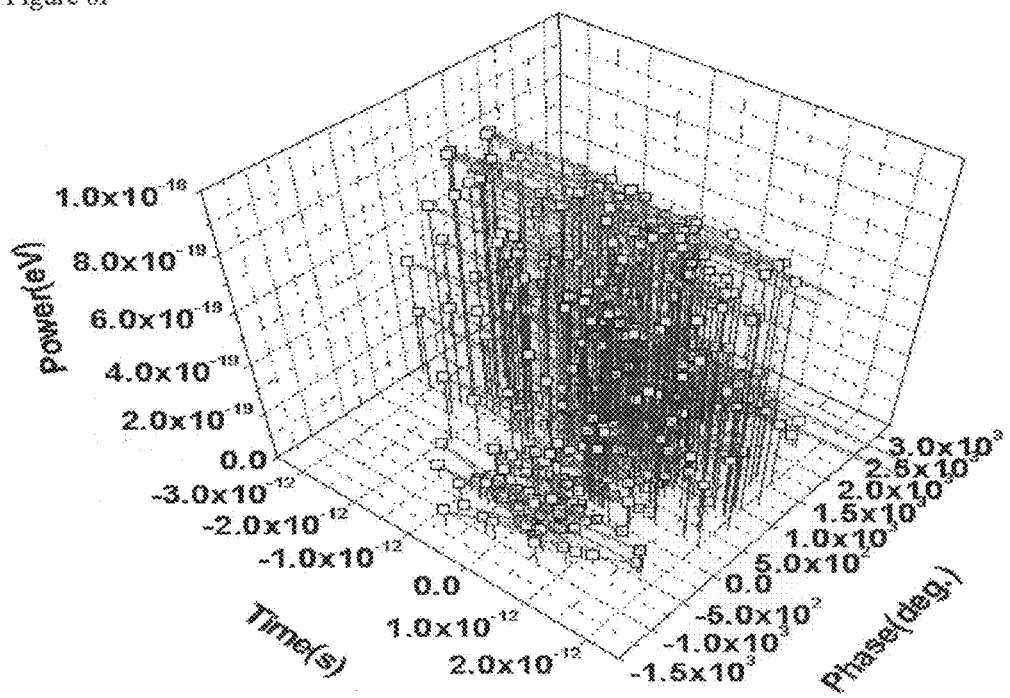
Figure 6I:
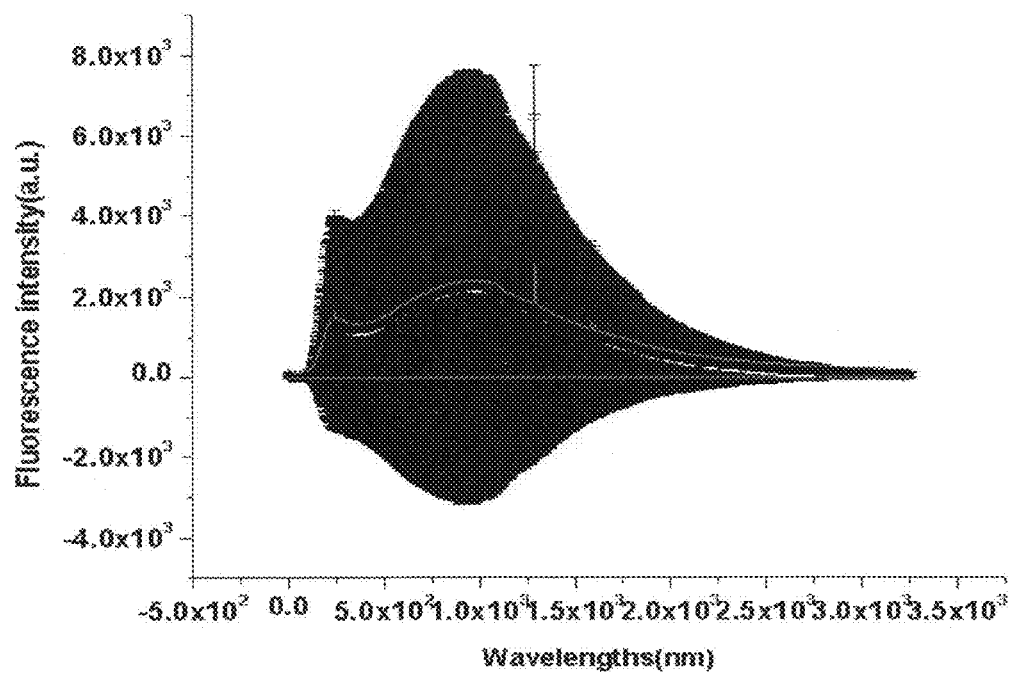
Figure 6V:
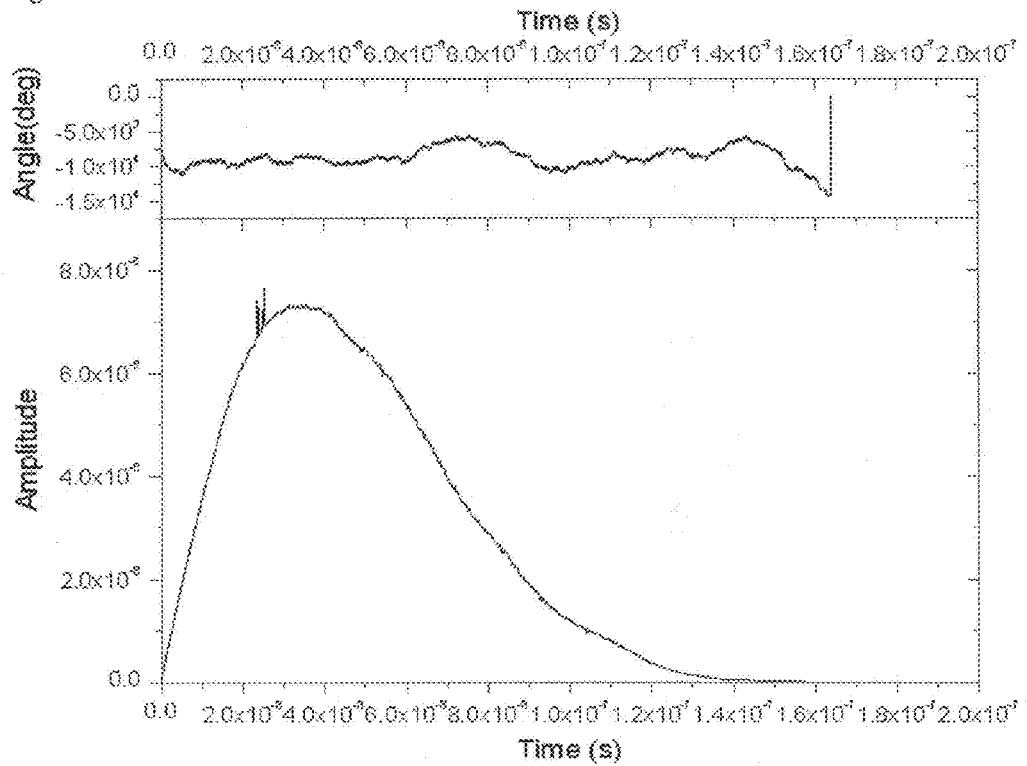
Figure 6V:
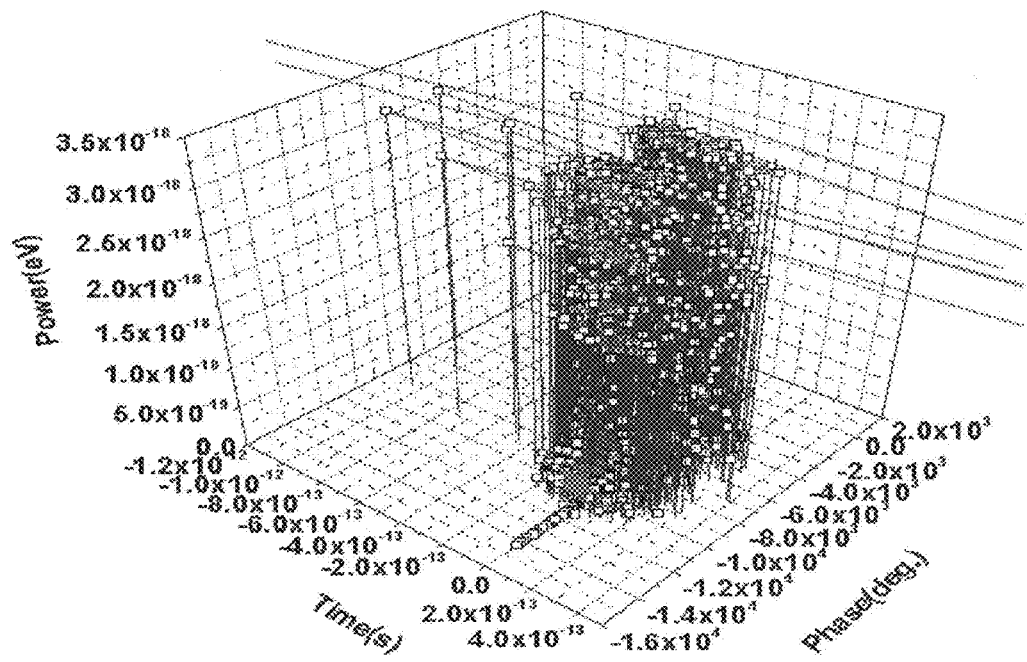
Figure 6I:
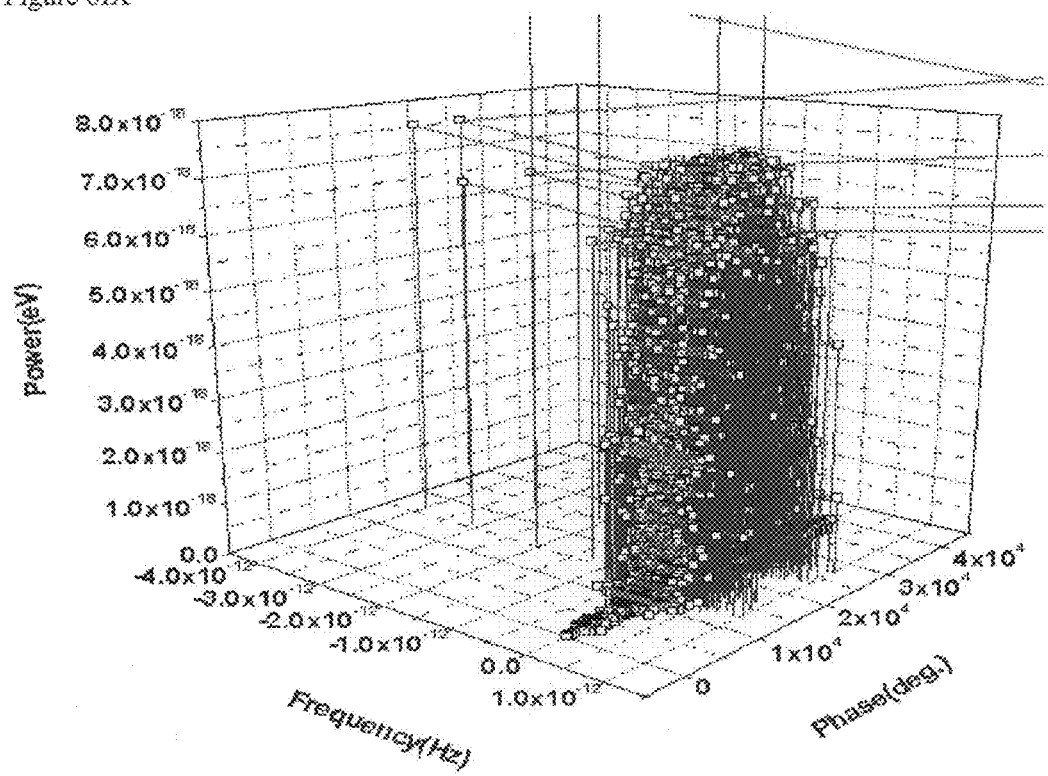
Figure 6X:
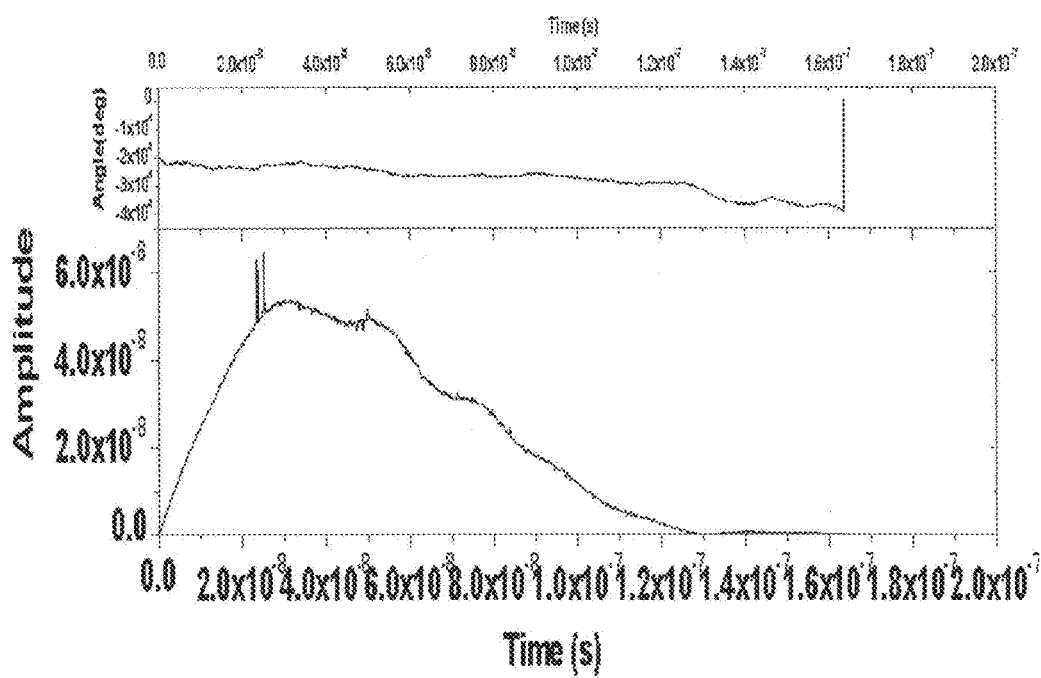
Figure 6X:
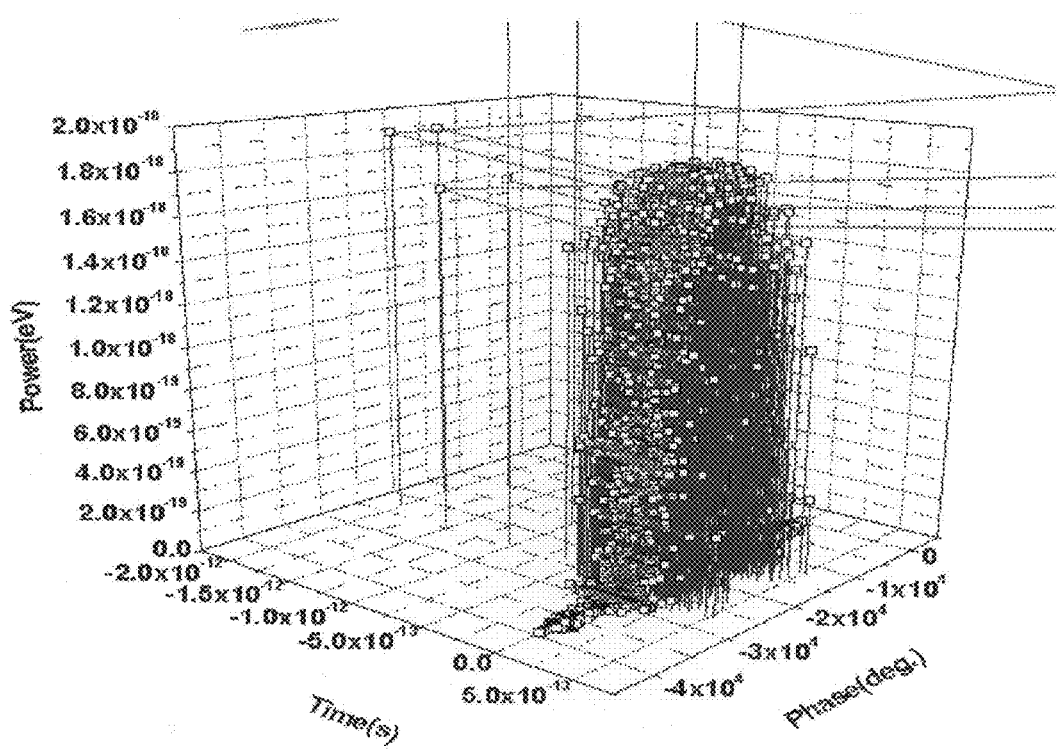

Pharmaceutical liquids are prepared according to the pharmaceutical standards, which may refer to the SFDA issued by the Ministry of Health in China. FIG. 6a-z and I-XI depict a C-AFM image of self-assembled QCA arrays and its single-electron-driven and photoelectron co-tunneling-driven room temperature superconductor qubit operator network features as well as spinning magnetic field-tuned symmetry and non-symmetry CNOT and Majority QCA arrays in the room temperature superconductor qubit operator networks obtained form the 2:3:1:2 product of Example 6.

i. A verapamil hydrochloride pharmaceutical liquid is prepared at a concentration of 2.5 mg/5 mL.
ii. An isoprenaline hydrochloride pharmaceutical liquid is prepared at a concentration of 2 mg/100 mL.
iii. A physiological buffer solution of superoxide dismutase is prepared at a concentration of 1 mg/2 mL.
iv. A physiological buffer solution of adenosine triphosphate is prepared at a concentration of 20 mg/3.3 mL.
v. A verapamil hydrochloride pharmaceutical droplet may comprise the molecular number of about $10^{12}$ verapamil hydrochloride molecules to about $10^{14}$ verapamil hydrochloride molecules.
vi. An isoprenaline hydrochloride pharmaceutical droplet may comprise the molecular number of about $10^{14}$ isoprenaline hydrochloride molecules to about $10^{15}$ isoprenaline hydrochloride molecules.
vii. A superoxide dismutase buffer droplet may consist of about $10^{11}$ superoxide dismutase molecules to about $10^{13}$ superoxide dismutase molecules.
viii. An adenosine triphosphate buffer droplet may be made up of about $10^{11}$ adenosine triphosphate molecules to about $10^{19}$ adenosine triphosphate molecules.
ix. A bio-redox single electron system is made in physiological buffer solution of xanthine oxidase (XO) and xanthine (X) according to a 1:20 molecular mixture ratio, and the desired molecular xanthine number may be in a range of about $3\times10^{16}$ X molecules to about $3\times10^{19}$ X molecules.
x. A hexa-redox-pharmaceutical droplet hybrid is made by mixing v, vi, vii, viii and ix according to a desired molecular mixture ratio of 2:3:1:2 in the $L_9(3)^4$ orthogonal design protocol.
xi. A hybrid droplet of x is prepared onto a 0.01-0.05 Ω·cm n-doped silicon substrate surface by controlling the spatial distance of 0 Å-200 Å at −20° C. for 8-12 hours, up to forming to a redox nano-drug quantum dot network lattice through a droplet crystal lattice hetero-epitaxy bottom-up self-assembly approach.
xii. At a room temperature and in air, C-AFM is used for imaging the topographic structure of a self-assembled redox nano-drug quantum dot room temperature superconductor QCA network lattice, as shown in FIG. 6*a*.
xiii. At a room temperature and in air, a laser micro-PL spectrum system tool characterizes an average PL spectrum with s.d., and polariton-driven room temperature superconductor symmetry spin-down and spin-up qubit QCA networks and its operator permutations in $\hbar$-related power-frequency-phase and power-time-phase spectra, as well as external spinning magnetic fields (RTD10t, RTD50t, RTD110t, 70D, 104D)—tuned symmetry to non-symmetry QCA networks and operator permutations, as profiled in FIG. 3*b-z* and I-XI.

What is claimed is:
1. A process for constructing a room temperature qubit network on a surface of a substrate, comprising:
preparing at least one of
a first droplet having $10^{11}$ to $10^{19}$ molecules of 1:20 ratio of xanthine oxidase (XO):xanthine (X)-based redox building blocks of a uni-hybrid of verapamil hydrochloride:isoproterenol hydrochloride:superoxide dismutase:adenosine triphosphate;
a second droplet having $10^{11}$ to $10^{19}$ molecules of 1:20 ratio of xanthine oxidase (XO):xanthine (X)-based redox building blocks of a bi-hybrid of verapamil hydrochloride:isoproterenol hydrochloride:superoxide dismutase:adenosine triphosphate;
a third droplet having $10^{11}$ to $10^{19}$ molecules of 1:20 ratio of xanthine oxidase (XO):xanthine (X)-based redox building blocks of a tri-hybrid of verapamil hydrochloride:isoproterenol hydrochloride:superoxide dismutase:adenosine triphosphate; and
a fourth droplet having $10^{11}$ to $10^{19}$ molecules of 1:20 ratio of xanthine oxidase (XO):xanthine (X)-based redox building blocks of a tetra-hybrid of verapamil hydrochloride:isoproterenol hydrochloride:superoxide dismutase:adenosine triphosphate;
forming a liquid layer that bonds to the surface of the substrate by placing at least one of the first droplet, the second droplet, the third droplet, and the fourth droplet on the surface of the substrate, the substrate being a 0.01 Ω·cm~0.05 Ω·cm N-doped silicon or graphite;
forming a room temperature qubit network by self-assembly on the substrate by subjecting the liquid layer to −4° C.~−20° C. for 8~12 hours when the substrate is the 0.01 Ω·cm~0.05 Ω·cm N-doped silicon, or 4° C.~18° C. for 30~60 minutes when the substrate is graphite.
2. The process of claim 1, wherein each of the first droplet, the second droplet, the third droplet, and the fourth droplet includes:
$10^{12}$ to $10^{14}$ molecules of verapamil hydrochloride;
$10^{14}$ to $10^{15}$ molecules of isoprenaline hydrochloride;
$10^{11}$ to $10^{13}$ molecules of superoxide dimutase;
$10^{11}$ to $10^{19}$ molecules of adenosine triphosphate.
3. The process according to claim 1, wherein the room temperature qubit network is a 2D qubit network of 5000 Å×5000 Å on the surface of the substrate.
4. The process according to claim 1, wherein the room temperature qubit network is a 3D qubit network of 8000 Å×8000 Å×200 Å on the surface of the substrate.
5. The process according to claim 1, wherein the room temperature qubit network is a 3D qubit network of 9000 Å×9000 Å×85 Å on the surface of the substrate.
6. The process according to claim 1, wherein the room temperature qubit network is a 3D qubit network of 9500 Å×9500 Å×70 Å on the surface of the substrate.

* * * * *